(12) United States Patent
McCurdy et al.

(10) Patent No.: US 9,604,926 B2
(45) Date of Patent: Mar. 28, 2017

(54) HIGHLY SELECTIVE SIGMA RECEPTOR RADIOLIGANDS

(75) Inventors: Christopher R. McCurdy, Oxford, MS (US); Christophe Mesangeau, Oxford, MS (US); Frederick T. Chin, Sunnyvale, CA (US); Michelle L. James, Menlo Park, CA (US); Bin Shen, Mountain View, CA (US); Sanjiv Gambhir, Portola Valley, CA (US)

(73) Assignee: THE UNIVERSITY OF MISSISSIPPI, University, MS (US)

(*) Notice: Subject to any disclaimer, the term of this patent is extended or adjusted under 35 U.S.C. 154(b) by 164 days.

(21) Appl. No.: 13/151,084

(22) Filed: Jun. 1, 2011

(65) Prior Publication Data

US 2011/0280804 A1    Nov. 17, 2011

Related U.S. Application Data

(63) Continuation-in-part of application No. 12/785,217, filed on May 21, 2010, now Pat. No. 8,686,008,
(Continued)

(51) Int. Cl.
C07D 277/62 (2006.01)
C07D 277/68 (2006.01)
(Continued)

(52) U.S. Cl.
CPC ........ *C07D 209/08* (2013.01); *A61K 51/0453* (2013.01); *A61K 51/0455* (2013.01); *A61K 51/0459* (2013.01); *A61K 51/0468* (2013.01); *C07D 209/10* (2013.01); *C07D 209/48* (2013.01); *C07D 235/26* (2013.01); *C07D 263/58* (2013.01); *C07D 265/36* (2013.01); *C07D 277/68* (2013.01); *C07D 277/70* (2013.01); *C07D 279/16* (2013.01); *C07D 295/13* (2013.01); *C07D 403/06* (2013.01); *C07D 405/04* (2013.01);
(Continued)

(58) Field of Classification Search
CPC .......................... C07D 277/62; C07D 277/68
USPC .................... 548/153, 165; 514/367
See application file for complete search history.

(56) References Cited

U.S. PATENT DOCUMENTS 4,215,119 A    7/1980  Mentrup et al.
4,371,388 A *  2/1983  D'Amico ............... 504/267
(Continued)

FOREIGN PATENT DOCUMENTS

EP     1043319 A1     10/2000
WO     WO 87-02359 A1  4/1987

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784.*
(Continued)

*Primary Examiner* — Kendra D Carter
(74) *Attorney, Agent, or Firm* — Hershkovitz & Associates, PLLC; Abraham Hershkovitz; Eugene Rzucidlo

(57) ABSTRACT

Compounds having the general formula III', or IV'

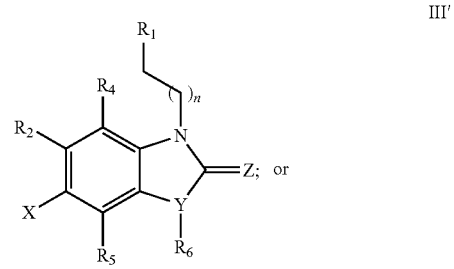

III'

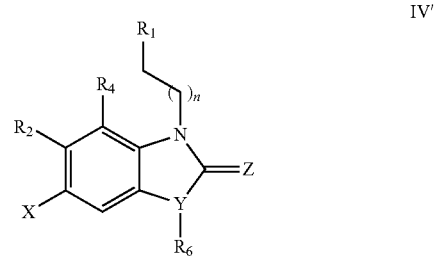

IV' wherein $R_1$ can be a radical of an optionally substituted C-4 to C-7 N-containing heterocycle or a radical of an optionally substituted cyclic or acyclic tertiary amine or isoindoline-1,3-dione; $R_{2,4,5,6}$ can each independently be any one or combinations of the following moieties, cyano, nitro, acyl, alkyl, amido, azido, isothiocyanate, isocyanate, optionally substituted anilino, halogens, ethers, sulfonamides, thioacyl, nitro, aromatic, heterocyclic, olefinic, acetylene, deuterium, or tritium; Y is S; Z can be either H, O, S, S—R or NR where R groups can be either H, aryls, alkyls, or cycloalkyls; "n" can be 1 to 5 carbons in length and stereoisomers, functional analogs, and pharmaceutically acceptable salts thereof and wherein the moiety bridging $R_1$ and N can be a substituted alkylene, optionally substituted alkenylene or optionally substituted alkynylene and where the alkylene group can include an inserted $C_3$-$C_5$ cycloalkyl group, aromatic, and heterocyclic group; and wherein X is $C_1$-$C_4$ radiohaloalkyl.

8 Claims, 11 Drawing Sheets

Related U.S. Application Data which is a continuation-in-part of application No. 12/673,486, filed as application No. PCT/US2008/073478 on Aug. 18, 2008, now Pat. No. 8,809,381.

(60) Provisional application No. 60/956,249, filed on Aug. 16, 2007.

(51) Int. Cl.

| | |
|---|---|
| *C07D 209/08* | (2006.01) |
| *A61K 51/04* | (2006.01) |
| *C07D 209/10* | (2006.01) |
| *C07D 209/48* | (2006.01) |
| *C07D 235/26* | (2006.01) |
| *C07D 263/58* | (2006.01) |
| *C07D 265/36* | (2006.01) |
| *C07D 277/70* | (2006.01) |
| *C07D 279/16* | (2006.01) |
| *C07D 295/13* | (2006.01) |
| *C07D 403/06* | (2006.01) |
| *C07D 405/04* | (2006.01) |
| *C07D 413/06* | (2006.01) |
| *C07D 413/12* | (2006.01) |
| *C07D 417/06* | (2006.01) |
| *C07D 491/107* | (2006.01) |
| *C07D 491/20* | (2006.01) |

(52) U.S. Cl.
CPC ......... *C07D 413/06* (2013.01); *C07D 413/12* (2013.01); *C07D 417/06* (2013.01); *C07D 491/107* (2013.01); *C07D 491/20* (2013.01)

(56) References Cited

U.S. PATENT DOCUMENTS

| | | | |
|---|---|---|---|
| 4,791,104 A | 12/1988 | Picciola et al. | |
| 5,473,066 A * | 12/1995 | Yamamori ............ | C07C 319/14 540/491 |

OTHER PUBLICATIONS

Bars, D.L. "Fluorine-18 and medical imaging: Radiopharmaceuticals for positron emission tomography" Journal of Florine Chemistry, 2006, vol. 127, pp. 1488-1493.*
Sheridan, R.P. "The Most Common Chemical Replacements in Drug-like Compounds", J. Chem. Inf. Comput. Sci., 2002, vol. 42, pp. 103-108.*
Costa et al. "Synthesis and Receptor Binding Properties of Fluoro—and Iodo-Substituted High Affinity Sigma Receptor Ligands: Identification of Potential PET and SPECT sigma Receptor Imaging Agents" .Journal of Medicinal Chemistry, 1992, vol. 35, No. 12, pp. 2221-2230.*
Matsumoto, R. R.; McCracken, K. A.; Pouw, B.; Miller, J.; Bowen, W. D.; Williams, W.; De Costa, B. R. *N*-alkyl substitute analogs of the σ receptor ligand BD1008 and traditional σ receptor ligands affect cocaine-induced convulsions and lethality in mice. *Eur. J. Pharmacol.* 2001, 411, 261-273.
Maurice, T.; Lockhart, B. P. Neuroprotective and anti-amnesic prtentials of sigma (σ) receptor ligands. *Prog. Neuropsychopharmacol. Biol. Psychiatry* 1997, 21, 69-102.
Matsumoto, R. R.; Bowen, W. D.; Su, T. P., eds. *Sigma receptors: chemistry, cell biology and clinical implications.* New York: Springer, 2007.
Hanner, M.; Moebus, F. F.; Flandorfer, A.; Knaus, H-G.; Striessing, J.; Kempner, E.; Glossmann, H. Purification, molecular cloning, and expression of the mammalian sigma$_1$—binding site. *Proc. Natl. Acad. Sci. USA*, 1996, 93, 8072-8077.
Kekuda, R.; Prasad, P. D.; Fei, Y-J.; Leibach, F. H.; Ganapathy, V. Cloning and functional expression of the human type 1 sigma receptor (hSigmaR1). *Biochem. Biophys. Res. Commun.* 1996, 229, 553-558.
Seth, P.; Leibach, F. H.; Ganapathy, V. Cloning and structural analysis of the cDNA and the gene encoding the murine type 1 sigma receptor. *Biochem. Biophys. Res. Commun.* 1997, 241, 535-540.
Seth, P.; Fei, Y-J.; Li, H. W.; Huang, W.; Leibach, F. H.; Ganapathy, V. Cloning and functional characterization of a σ receptor from rat brain. *J. Neurochem.* 1998, 70, 922-931.
Mei, J.; Pasternak, G. W. Molecular cloning and pharmaceutical characterization of the rat sigma$_1$ receptor. *Biochem. Pharmacol.* 2001, 62, 349-355.
Perrine, D. M. *The Chemistry of Mind-Altering Drugs.* Washington, D.C.: American Chemical Society, 1996.
Carroll, F.I.; Howell, L.L.; Kuhar, M.J. Pharmacotherapies for treatment of cocaine abuse: preclinical aspects. *J. Med. Chem.* 1999, 42, 2721-2736.
Sharkey, J.; Glen, K. A.; Wolfe, S.; Kuhar, M.J. Cocaine binding at sigma receptors. *Eur. J. Pharmacol.* 1988, 149, 171-174.
Mittleman, R.; Wetli, C.V. Death caused by recreational cocaine use: an update. *JAMA* 1984, 252, 1889-1893.
Martin, W. R.; Eades, C. G.; Thompson, J. A.; Huppler, R. E.; Gilbert, P. E. The effects of morphine—and nalorphine—like drugs in the nondependent and morphine—dependent chronic spinal dog. *J Pharmacol Exp Ther.* 1976, 197, 517-32.
Martin, W. R. A steric theory of opioid agonists, antagonists, agonist-antagonists, and partial agonists. *NIDA Res Monogr.* 1984, 49, 16-23.
Hellewell, S. B.; Bruce, A.; Feinstein, G.; Orringer, J.; Williams, W.; Bowen, W. D. Rat liver and kidney contain high densities of sigma 1 and sigma 2 receptors: characterization by ligand binding and photoaffinity labeling. *Eur J Pharmacol.* 1994, 268, 9-18.
Maurice, T.; Su, T. P. The pharmacology of sigma-1 receptors. *Pharmacol Ther.* 2009, 124, 195-206.
Quirion, R.; Bowen, W. D.; Itzhak, Y.; Junien, J. L.; Musacchio, J. M.; Rothman, R. B.; Su, T. P.; Tam, S. W.; Taylor, D. P. A proposal for the classification of sigma binding sites. *Trends Pharmacol Sci.* 1992, 13, 85-6.
Guitart, X.; Codony, X.; Monroy, X. Sigma receptors: biology and therapeutic potential. *Psychopharmacology (Berl).* 2004, 174, 301-19.
Maurice, T.; Phan, V. L.; Privat, A. The anti-amnesic effects of sigmal (sigma1) receptor agonists confirmed by in vivo antisense strategy in the mouse. *Brain Res.* 2001, 898, 113-21.
Su, T. P. Delineating biochemical and functional properties of sigma receptors: emerging concepts. *Crit Rev Neurobiol.* 1993, 7, 187-203.
Vilner, B. J.; John, C. S.; Bowen, W. D. Sigma-1 and sigma-2 receptors are expressed in a wide variety of human and rodent tumor cell lines. *Cancer Res.* 1995, 55, 408-13.
Wang, B.; Rouzier, R.; Albarracin, C. T.; Sabin, A.; Wagner, P.; Yang, Y.; Smith, T. L.; Meric-Bernstam, F.; Marcelo Aldaz, C.; Hortobagyi, G. N.; Pusztai, L. Expression of sigma 1 receptor in human breast cancer. *Breast Cancer Res Treat.* 2004, 87, 205-14.
Gonzalez, G. M.; Werling, L. L. Release of [3H]dopamine from guinea pig striatal slices is modulated by sigmal receptor agonists. *Naunyn Schmiedebergs Arch Pharmacol.* 1997, 356, 455-61.
Kobayashi, T.; Matsuno, K.; Nakata, K.; Mita, S. Enhancement of acetylcholine release by SA4503, a novel sigma 1 receptor agonist, in the rat brain. *J Pharmacol Exp Ther.* 1996, 279, 106-13.
Collier, T. L.; Waterhouse, R. N.; Kassiou, M. Imaging sigma receptors: applications in drug development. *Curr Pharm Des.* 2007, 13, 51-72.
Senda, T.; Matsuno, K.; Kobayashi, T.; Nakazawa, M.; Nakata, K.; Mita, S. Ameliorative effect of SA4503, a novel cognitive enhancer, on the basal forebrain lesion-induced impairment of the spatial learning performance in rats. *Pharmacol Biochem Behav.* 1998, 59, 129-34.
Harukuni, I.; Bhardwaj, A.; Shaivitz, A. B.; DeVries, A. C.; London, E. D.; Hurn, P. D.; Traystman, R. J.; Kirsch, J. R.; Faraci, F. M. sigma(1)-receptor ligand 4-phenyl-1-(4-phenylbutyl)-piperidine affords neuroprotection from focal ischemia with prolonged reperfusion. *Stroke.* 2000, 31, 976-82.

(56) References Cited

OTHER PUBLICATIONS

Volz, H. P.; Stoll, K. D. Clinical trials with sigma ligands. *Pharmacopsychiatry.* 2004, 37 Suppl 3, S214-20.
Xu, Y. T.; Kaushal, N.; Shaikh, J.; Wilson, L. L.; Mesangeau, C.; McCurdy, C. R.; Matsumoto, R. R. A novel substituted piperazine, CM156, attenuates the stimulant and toxic effects of cocaine in mice. *J Pharmacol Exp Ther.* 2010, 333, 491-500.
Ucar, H.; Cacciaguerra, S.; Spampinato, S.; Van derpoorten, K.; Isa, M.; Kanyonyo, M.; Poupaert, J. H. 2(3H)-benzoxazolone and 2(3H)-benzothiazolone derivatives: novel, potent and selective sigmal receptor ligands. *Eur J Pharmacol.* 1997, 335, 267-73.
Berardi, F.; Ferorelli, S.; Abate, C.; Pedone, M. P.; Colabufo, N. A.; Contino, M.; Perrone, R. Methyl substitution on the piperidine ring of N-[omega-(6-methoxynaphthalen-1-yl)alkyl] derivatives as a probe for selective binding and activity at the sigma(1) receptor. *J Med Chem.* 2005, 48, 8237-44.
Hudkins, R. L.; Mailman, R. B.; DeHaven-Hudkins, D. L. RLH-033, a novel, potent and selective ligand for the sigma 1 recognition site. *Eur J Pharmacol.* 1994, 271, 235-6.
Maestrup, E. G.; Fischer, S.; Wiese, C.; Schepmann, D.; Hiller, A.; Deuther-Conrad, W.; Steinbach, J.; Wunsch, B.; Brust, P. Evaluation of spirocyclic 3-(3-fluoropropyl)-2-benzofurans as sigmal receptor ligands for neuroimaging with positron emission tomography. *J Med Chem.* 2009, 52, 6062-72.
Matsuno, K.; Nakazawa, M.; Okamoto, K.; Kawashima, Y.; Mita, S. Binding properties of SA4503, a novel and selective sigma 1 receptor agonist. *Eur J Pharmacol.* 1996, 306, 271-9.
Moussa, I. A.; Banister, S. D.; Beinat, C.; Giboureau, N.; Reynolds, A. J.; Kassiou, M. Design, synthesis, and structure-affinity relationships of regioisomeric N-benzyl alkyl ether piperazine derivatives as sigma-1 receptor ligands. *J Med Chem.* 2010, 53, 6228-39.
Piergentili, A.; Amantini, C.; Del Bello, F.; Giannella, M.; Mattioli, L.; Palmery, M.; Perfumi, M.; Pigini, M.; Santoni, G.; Tucci, P.; Zotti, M.; Quaglia, W. Novel highly potent and selective sigma 1 receptor antagonists related to spipethiane. *J Med Chem.* 2010, 53, 1261-9.
Quaglia, W.; Giannella, M.; Piergentili, A.; Pigini, M.; Brasili, L.; Di Toro, R.; Rossetti, L.; Spampinato, S.; Melchiorre, C. 1'-Benzyl-3,4-dihydrospiro[2H-1-benzothiopyran-2,4'-piperidine] (spipethiane), a potent and highly selective sigmal ligand. *J Med Chem.* 1998, 41, 1557-60.
Yous, S.; Wallez, V.; Belloir, M.; Caignard, D. H.; McCurdy, C. R. Novel 2(3H)-Benzothiazolones as Highly Potent and Selective Sigma-1 Receptor Ligands. *Med Chem Res.* 2005, 14, 158-168.
Kawamura, K.; Ishiwata, K.; Tajima, H.; Ishii, S.; Matsuno, K.; Homma, Y.; Senda, M. In vivo evaluation of [$^{11}$C]SA4503 as a PET ligand for mapping CNS sigma(1) receptors. *Nucl Med Biol.* 2000, 27, 255-61.
Kawamura, K.; Tsukada, H.; Shiba, K.; Tsuji, C.; Harada, N.; Kimura, Y.; Ishiwata, K. Synthesis and evaluation of fluorine-18-labeled SA4503 as a selective sigmal receptor ligand for positron emission tomography. *Nucl Med Biol.* 2007, 34,571-7.
Waterhouse, R. N.; Collier, T. L. In vivo evaluation of [$^{18}$F]1-(3-fluoropropyl)-4-(4-cyanophenoxymethyl)piperidine: a selective sigma-1 receptor radioligand for PET. *Nucl Med Biol.* 1997, 24, 127-34.
Waterhouse, R. N.; Chang, R. C.; Zhao, J.; Carambot, P. E. In vivo evaluation in rats of [$^{18}$F]1-(2-fluoroethyl)-4-[(4-cyanophenoxy)methyl]piperidine as a potential radiotracer for PET assessment of CNS sigma-1 receptors. *Nucl Med Biol.* 2006, 33, 211-5.
Waterhouse, R. N.; Zhao, J.; Stabin, M. G.; Ng, H.; Schindler-Horvat, J.; Chang, R. C.; Mirsalis, J. C. Preclinical acute toxicity studies and dosimetry estimates of the novel sigma-1 receptor radiotracer, [$^{18}$F]SFE. *Mol Imaging Biol.* 2006, 8, 284-91.
Mach, R. H.; Gage, H. D.; Buchheimer, N.; Huang, Y.; Kuhner, R.; Wu, L.; Morton, T. E.; Ehrenkaufer, R. L. N-[$^{18}$F]4'-fluorobenzylpiperidin-4yl-(2-fluorophenyl) acetamide ([18F]FBFPA): a potential fluorine-18 labeled PET radiotracer for imaging sigma-1 receptors in the CNS. *Synapse.* 2005, 58, 267-74.

Fischer, S.; Wiese, C.; Grosse Maestrup, E.; Hiller, A.; Deuther-Conrad, W.; Scheunemann, M.; Schepmann, D.; Steinbach, J.; Wunsch, B.; Brust, P. Molecular imaging of sigma receptors: synthesis and evaluation of the potent sigma(1) selective radioligand [$^{18}$F]fluspidine. *Eur J Nucl Med Mol Imaging.* 2010.
Fishback, J. A.; Mesangeau, C.; Poupaert, J. H.; McCurdy, C. R.; Matsumoto, R. R. Synthesis and characterization of [$^3$H]-SN56, a novel radioligand for the σ1 receptor. *European Journal of Pharmacology.* In Press.
Bowen, W. D.; Tolentino, P. J.; Kirschner, B. N.; Varghese, P.; de Costa, B. R.; Rice, K. C. Sigma receptors and signal transduction: negative modulation of signaling through phosphoinositide-linked receptor systems. *NIDA Res Monogr.* 1993, 133, 69-93.
Loening, A. M.; Gambhir, S. S. AMIDE: a free software tool for multimodality medical image analysis. *Mol Imaging.* 2003, 2, 131-7.
Kronauge, J. F.; Noska, M. A.; Davison, A.; Holman, B. L.; Jones, A. G. Interspecies variation in biodistribution of technetium (2-carbomethoxy-2-isocyanopropane)6+. *J Nucl Med.* 1992, 33, 1357-65.
Rodvelt, K. R.; Lever, S. Z.; Lever, J. R.; Blount, L. R.; Fan, K.-H.; Miller, D. K. SA 4503 attenuates cocaine-induced hyperactivity and enhances methamphetamine substitution for a cocaine discriminative stimulus. *Pharmacology, Biochemistry and Behavior.* 2011, 97, 676-682.
Matsumoto, R. R.; Liu, Y.; Lerner, M.; Howard, E. W.; Brackett, D. J. Sigma receptors: potential medications development target for anti-cocaine agents. *Eur. J. Phamracol.,* 2003, 469,1-12.
Su, T.-P.; Hayashi, T.; Maurice, T.; Buch, S.; Ruoho, A. E. The sigma-1 receptor chaperone as an inter-organelle signaling modulator. *Trends in Pharmacological Sciences.* 2010, 31, 557-566.
Roh, D.-H.; Kim, H.-W.; Yoon, S.-Y.; Seo, H.-S.; Kwon, Y.-B.; Kim, K.-W.; Han, H.-J.; Beitz, A. J.; Lee, J.-H. Intrathecal Administration of Sigma-1 Receptor Agonists Facilitates Nociception: Involvement of a Protein Kinase C-development Pathway. *Journal of Neuroscience Research.* 2008, 86, 3644-3654.
Roh, D.-H.; Kim, H.-W.; Yoon, S.-Y.; Seo, H.-S.; Kwon, Y.-B.; Kim, K.-W.; Han, H.-J.; Beitz, A. J.; Na, H.-S.; Lee, J.-H. Intrathecal injection of the σ1 receptor antagonist BD1047 blocks both mechanical allodynia and increases in spinal NR1 expression during the induction phase of rodent neuropathic pain. *Anesthesiology.* 2008, 109, 879-889.
Kibaly, C.; Meyer, L.; Patte-Mensah, C.; Mensah-Nyagan, A. G. Biochemical and functional evidence for the control of pain mechanisms by dehydroepiandrosterone endogenously synthesized in the spinal cord. *The FASEB Journal.* 2008, 22, 93-104.
De la Puente, B.; Nadal, X.; Portillo-Salido, E.; Sanchez-Arroyos, R.; Ovalle, S.; Palacios, G.; Num, A.; Romero, L.; Entrena, J. M.; Baeyens, J. M.; Lopez-Garcia, J. A.; Maldonado, R.; Zamanillo, D.; Vela, J. M. Sigma-1 receptors regulate activity-induced spinal sensitization and neuropathic pain after peripheral nerve injury. *Pain.* 2009, 145, 294-303.
Rybczynska, A. A.; Elisinga, P. H.; Sijbesma, J. W.; Ishiwata, K.; de Jong, J. R.; de Vries, E. F.; Dierckx, R. A.; van Waarde, A. Steroid hormones affect binding of the sigma ligand $^{11}$C-SA4503 in tumour cells and tumour-bearing rats. *Eur. J. Nucl Med Mol Imaging.* 2009, 36, 1167-1175.
van Waarde, A.; Rybczynska, A. A.; Ramakrishnan, N.; Ishiwata, K.; Elsinga, P. H.; Dierckx, R. A. Sigma receptors in oncology: therapeutic and diagnostic applications of sigma ligands. *Curr Pharm Des.* 2010, 16, 3519-1537.
Jansen, K. L. R.; Faull, R. L. M.; Storey, P.; Leslie, R. A. Loss of sigma binding sites in the CA1 area of the anterior hippocampus in Alzheimer's disease correlates with CA1 pyramidal cell loss. *Brain Research.* 1993, 623, 299-302.
Mishina, M.; Ohyama, M.; Ishii, K.; Kitamura, S.; Kimura, Y.; Oda, K.-i.; Kawamura, K.; Sasaki, T.; Kobayashi, S.; Katayama, Y.; Ishiwata, K. Low density of sigmas receptors in early Alzheimer's disease. *Ann. Nucl. Med.* 2008, 22, 151-156.
Mishina, M.; Ishiwata, K.; Ishii, K.; Kitamura, S.; Kimura, Y.; Kawamura, K.; Oda, K.; Sasaki, T.; Sakayori, O.; Hamamoto, M.; Kobayashi, S.; Katayama, Y. Function of sigma$_1$ receptors in Parkinsons's disease. *Acta Neurol Scand.* 2005, 112, 103-107.

(56) References Cited

OTHER PUBLICATIONS

Weissman, A. D.; Casanova, M. F.; Kleinman, J. E.; London, E. D.; de Souza, E. B. Selective loss of cerebral cortical *Sigma*, but not PCP binding sites in schizophrenia. *Biol Psychiatry.* 1991, 29, 41-54.

Shibuya, H.; Mori, H.; Toru, M. Sigma receptors in schizophrenic cerebral cortices. *Neurochem Res.* 1992, 17, 983-990.

Silver, H.; Barash, I.; Aharon, N.; Kaplan, A.; Poyurovsky, M. Fluvoxamine augmentation of antipsychotics improves negative symptoms in psychotic chronic schizophrenic patients: a placebo-controlled study. *Int. Clin. Psychopharmacol.* 2000, 15, 257-261.

Iyo, M.; Shirayama, Y.; Watanabe, H.; Fujisaki, M.; Miyatake, R.; Fukami, G.; Shiina, A.; Nakazato, M.; Shiraishi, T. Letter to the Editor (Case Report): Fluvoxamine as a sigma-1 receptor agonist improved cognitive impairments in a patient with schizophrenia. *Prog. Neuropsych. Biol. Psych.* 2008, 32, 1072-1073.

Gatti, F.; Bellini, L.; Gasperini, M.; Perez, J.; Zanardi, R.; Smeraldi, E. Fluvoxamine alone in the treatment of delusional depression. *Am. J. Psychiatry,* 1996, 153, 414-416.

Narita, N.; Hashimoto, K.; Tomitaka, S.-i.; Minabe, Y. Interactions of selective serotonin reuptake inhibitors with subtypes of σ receptors in rat brain. *Eur. J. Pharmacol.* 1996, 307, 117-119.

Zanardi, R.; Franchini, L.; Gasperini, M.; Lucca, A.; Smeraldi, E.; Perez, J. Faster Onset of Action of Fluvoxamine in Combination with Pindolol in the Treatment of Delusional Depression: A controlled study. *J. Clin. Psychopharmacol.* 1998, 18, 441-446.

Haiman, G.; Pratt, H.; Miller, A. Effects of dextromethorphan/quinidine on auditory event-related potentials in multiple sclerosis patients with pseudobulbar affect. *J. Clin. Psychopharmacol.* 2009, 29, 444-452.

Cottraux, J.; Mollard, E.; Bouvard, M.; Marks, I. Exposure therapy, fluvoxamine, or combination treatment in obsessive-compulsive disorder: one-year followup. *Psychiatry Research.* 1993, 49, 63-75.

Hohagen, F.; Berger, M. New perspectives in research and treatment of obsessive-compulsive disorder. *Br. J. Psychiatry Suppl.* 1998, 35, 1.

Dell'Osso, B.; Allen, A.; Hollander, E. Fluvoxamine: a selective serotonin re-uptake inhibitor for the treatment of obsessive-compulsive disorder. *Expert Opinion on Pharmacotherapy.* 2005, 6, 2727-2740.

Yous, Said et al., "Novel 2(3H)-benzothiazolones as highly potent and selective sigma-1 receptor ligands" Medicinal Chemistry Research, 2005, vol. 14, No. 3, pp. 158-1683.

Ucar, Huseyin et al., "Synthesis and Anticonvulsant Activity of 2(3H)-benzoxazolone and 2(3H)-benzothiazolone derivatives" Journal of Medicinal Chemistry, 1998, vol. 41, No. 7, pp. 1138-1145.

Ucar, Huseyin et al., "2(3H)-benzoxazolone and 2(3H)-benzothiazolone derivatives: Novel, potent and selective sigma 1 receptor ligands" European Journal of Pharmacology, 1997, vol. 335, No. 2/3, pp. 267-273.

International Search Report issued Feb. 9, 2009 corresponding to PCT/US2008/073478.

\* cited by examiner

Figure 1. Selected sigma-1 receptor (σ-1 receptor) ligands and radioligands.
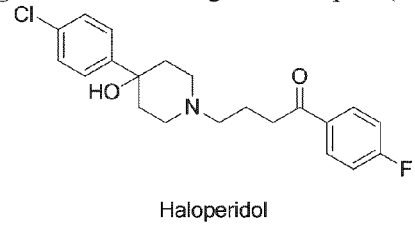
Haloperidol
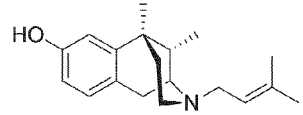
(+)-Pentazocine
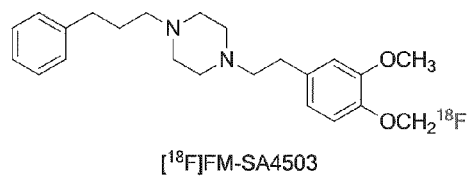
[$^{18}$F]FM-SA4503
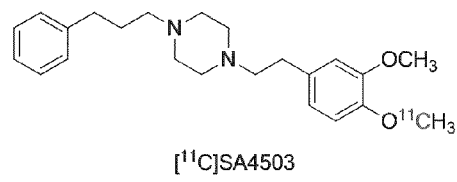
[$^{11}$C]SA4503
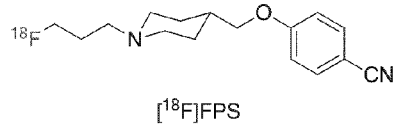
[$^{18}$F]FPS
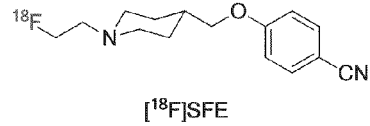
[$^{18}$F]SFE
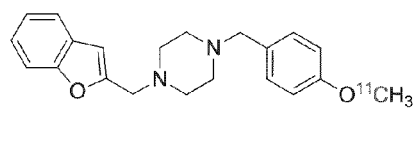
[$^{11}$C]13
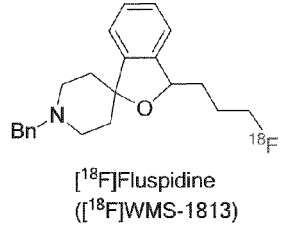
[$^{18}$F]Fluspidine
([$^{18}$F]WMS-1813)
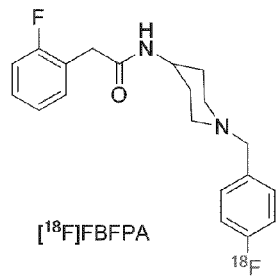
[$^{18}$F]FBFPA
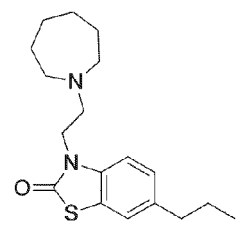
SN56
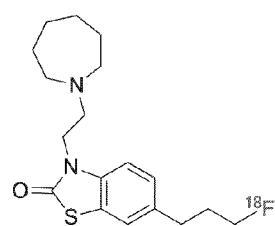
[$^{18}$F]FTC-146
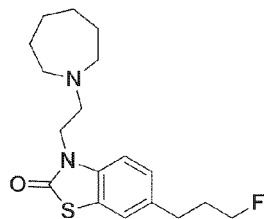
CM304

Metabolic stability of AZ_66 by Rat liver microsomes (1mg/ml)

| Time(min) | Percent Remaining | Percent Loss |
|---|---|---|
| 0 | 100 | 0 |
| 5 | 95.51694 | 4.48306 |
| 15 | 88.64231 | 11.35845 |
| 30 | 82.70131 | 17.29879 |
| 60 | 75.09347 | 24.3653 |

*In vitro* Half-life and Intrinsic clearance

| k(min⁻¹) | t₁/₂(min) | CLint(ml/min/mg) | CLint (whole liver) (L/min) |
|---|---|---|---|
| 0.006 | 115.56±15 | 0.006 | 0.002434 |

Incubation of CM_156 (10μM) with rat liver microsomes (1mg/ml)

| Time (min) | Percent Remaining |
|---|---|
| 0 | 100 |
| 15 | 16.4605 |
| 30 | 9.2356 |

Figure 17. Images from a selected baseline mouse PET study summed over different times. Dynamic imaging was commenced 1 minute prior to i.v. administration of [$^{18}$F]FTC-146 (102 µCi) and continued for a total of 62 minutes.

HIGHLY SELECTIVE SIGMA RECEPTOR RADIOLIGANDS

CROSS-REFERENCE TO RELATED APPLICATIONS

This is a Continuation-in-Part Application of U.S. application Ser. No. 12/785,217, filed on May 21, 2010 now U.S. Pat. No. 8,686,008 entitled "HIGHLY SELECTIVE SIGMA RECEPTOR LIGANDS," which is a Continuation-in-part application of U.S. application Ser. No. 12/673,486, filed on May 12, 2010, now U.S. Pat. No. 8,809,381 entitled "HIGHLY SELECTIVE SIGMA RECEPTOR LIGANDS," which claims priority of PCT/US08/73478 filed Aug. 18, 2008 which claims priority to U.S. Provisional Application No. 60/956,249 filed Aug. 16, 2007, the disclosure of all of which is expressly incorporated by reference herein in its entirety.

The subject invention was made with government support under a research project supported by the United States Government in NIDA Grant Number DA023205 and NCI ICMIC P50 CA114747 and the government has certain rights in this invention.

FIELD OF INVENTION

The present invention relates to the field of compounds which are sigma receptor ligands and methods of use thereof as sigma receptor ligands as well as radioligands and the use of radioligands.

BACKGROUND OF THE INVENTION

Sigma receptors (σ) have received much attention from the drug discovery field due to their possible involvement in schizophrenia, regulation of motor behavior, convulsions, anxiety, and the psychostimulant effects of drugs of abuse including cocaine, methamphetamine and 3,4-methylenedioxymethamphetamine (MDMA).[1,2] In addition to a host of neurological and psychiatric areas of interest, sigma receptors are promising drug development targets for, oncological, immunological, cardiovascular, opthalmological, developmental, gastrointestinal and metabolic disorders as well as those affecting the endocrine system. They are structurally unique proteins that are distinct from classical G protein-coupled receptors, ionotropic receptors, or receptor tyrosine kinases. With two subtypes currently known, they modulate cell survival and excitability, and subserve many critical functions in the body. Endogenous ligands for these receptors are unknown, though current clues point to neurosteroids.[3]

The two subtypes, σ-1 and σ-2, were delineated by studies examining their respective molecular weights, distribution in tissue and drug selectivity profiles. The 223 amino acid σ-1 protein with two transmembrane spanning regions has been purified and cloned from several animal species including mouse, rat, guinea pig, and human.[4-8] To date, the σ-1 receptor is well studied and known because of the receptor sequence information and availability of selective σ-1 ligands. But, the protein corresponding to σ-2 sites has not yet been cloned. Also, σ-2 receptor-selective ligands are less common, with tritiated DTG (1,3-di(2-tolyl)guanidine) being accepted as a radioligand in the presence of (+)-pentazocine (to block binding to σ-1 sites). Due to the lack of availability of detailed protein structural information and truly selective σ-2 ligands, the pharmacological characterization of the σ-2 subtype has been very limited. There is clearly a need for a selective σ-2 ligand which can not only act as a probe to explore unknown biochemical mechanisms, but also be used as a radioligand in σ-2 receptor binding assays.

The abuse of drugs is a serious social, economic and health problem worldwide. Some of the opiates, cocaine, amphetamines and phencyclidine (PCP) are the drugs of abuse with significant affinities for σ receptors. Current treatments for drugs of abuse are limited and there is a need to develop novel and effective agents to combat this problem.

Cocaine use and abuse has been reported as early as the late 1500 s.[9] The historical use has been associated with the chewing of leaves from the *Erythroxylon coca* bush, from which cocaine was isolated in 1860,[10] to eliminate fatigue in workers. Indeed, cocaine is a powerful and addictive psychostimulant. Cocaine abuse is widespread and is responsible for more serious intoxications and deaths than any other illicit drug. However, the invigorating effects of cocaine have caused it to become a major recreational drug of abuse throughout the world with an estimated 13 million people using the drug. In 2004, 34.2 million Americans aged 12 and over reported lifetime use of cocaine with approximately 5.6 million reporting annual use and an estimated 2 million reporting current use of the drug. In 2004 alone, there were an estimated 1 million new users of cocaine amounting to ~2,700 per day. Despite a decline between 2002 and 2003 which is thought to potentially be due to increases in usage of other stimulants such as methamphetamine, data from the National Survey on Drug Use and Health showed near a 70% increase in the number of people receiving treatment for cocaine addiction from 276,000 in 2003 to 466,000 in 2004.[11]

Currently, there are no approved medications to treat cocaine abuse or addiction. An effective strategy used to develop an anti-cocaine agent was the development of antagonists that compete with cocaine for its target proteins. For years, treatment approaches have targeted the dopaminergic system which is known to be involved in the actions and rewards of cocaine use. Many compounds were generated and tested that targeted the dopamine transporter which was identified as a primary site of action of cocaine. These compounds were met with very limited success as many of them just substituted for cocaine.[12] After many years of investigation at the dopamine transporter as well as the dopamine receptors, researchers have been challenged to envision novel mechanisms that may afford new therapeutic interventions for cocaine addiction.

Although many other mechanisms are under investigation, the a receptor system has been demonstrated and validated as a legitimate target for the attenuation of cocaine effects. The ability of cocaine to bind to the sigma receptors was discovered and first documented in 1988.[13] It was reported that cocaine had micromolar affinity to the sigma receptor, and this interaction corresponded to micromolar levels that were achievable by cocaine in the body.[14] Additional studies have indicated that reducing brain sigma receptor levels with antisense oligonucleotides attenuates the convulsive and locomotor stimulant actions of cocaine. Synthetic small molecule antagonists for sigma receptors have also been shown to mitigate the actions of cocaine in animal models. From prior work, the role of the σ-1 subtype has been clearly linked to the actions of cocaine. However, the role of the σ-2 receptor has been suggested, but is less clear due to the lack of truly selective ligands for this subtype.

Radioligands selective for σ-1 receptors have the potential to non-invasively detect and monitor various pathologies, including neurodegenerative diseases and cancer. Applicants herein report the synthesis, radiofluorination and evaluation of a new $^{18}$F fluorinated σ-1 receptor ligands including 6-(3-fluoropropyl)-3-(2-(azapan-1-yl)ethyl)benzo[d]thiazol-2(3H)-one (18, [$^{18}$F]FTC-146). [$^{18}$F]FTC-146 displays superior in vitro affinity and selectivity compared to other reported σ-1 receptor compounds. The new $^{18}$F fluorinated σ-1 receptor ligands, including [$^{18}$F]FTC-146, can be synthesized by nucleophilic fluorination using an automated module. [$^{18}$F]FTC-146 afforded a product with >99% radiochemical purity (RCP) and specific activity (SA) of 3.9±1.9 Ci/μmol (n=13). Cell uptake studies revealed that [$^{18}$F]FTC-146 accumulation correlated with levels of σ-1 receptor protein. Furthermore, the binding profile of [$^{18}$F]FTC-146 was comparable to that of known high affinity σ-1 receptor ligand (+)-[$^{3}$H] pentazocine in the same cell uptake assay. PET images of [$^{18}$F]FTC-146 in normal mice showed high uptake of the radioligand in the brain which is known to contain high levels of σ-1 receptors. Time activity curves (TACs) showed rapid, high initial uptake of [$^{18}$F]FTC-146 in the mouse brain. Pre-treatment with non-radioactive CM304 (1 mg/kg) reduced the binding of [$^{18}$F]FTC-146 in the brain at 60 min by 83% denoting that [$^{18}$F]FTC-146 accumulation in mouse brain represents specific binding to σ-1 receptors. These results indicate that [$^{18}$F]FTC-146 is a good candidate radiotracer for studying σ-1 receptors in living subjects.

Initially the sigma receptor was thought to belong to the opioid class of receptors;[15] however, further studies classified it as a distinct molecular entity, resulting in its recognition as a separate family of receptors.[16] There are at least two σ receptor subtypes, the σ-1 and σ-2 receptors.[17] The σ-1 receptor is the best characterized of the two at present.[18, 19]

Despite initial controversy and conflicting ideas, recent key discoveries concerning the σ receptor have helped elucidate various biological aspects about this molecular chaperone and its putative functional roles.[20,21] Mainly located at the endoplasmic reticulum of cells, σ-1 receptors have been implicated in a host of biochemical processes and pathological conditions including neurodegenerative diseases, psychiatric disorders, drug addiction, digestive function, regulation of smooth muscle contraction and ischemia.[20, 22-24] σ-1 receptors are also highly expressed in most known human cancers (e.g., breast, lung, colon, ovarian, prostate, brain).[24,25] Agonists for σ-1 receptors influence intracellular and extracellular Ca2+ levels and thus have a broad range of neuromodulatory effects.[26,27] Certain σ-1 receptor agonists have been shown to regulate endothelial cell proliferation,[28] improve cognition,[29,30] provide neuroprotection,[31] and act as anti-depressant agents,[18,32] while antagonists inhibit/attenuate cocaine-induced seizures,[33] highlighting the potential of σ-1 receptors as both a diagnostic and therapeutic target.

There are a multitude of compounds that target σ receptors, including three specific classes of compounds; 1) benzomorphans, such as (+)-pentazocine (FIG. 1) and (+)-N-allylnormetazocine (NANM) that preferentially bind σ-1 receptors (compared to their (−)-enantiomers), 2) endogenous neurosteroids like progesterone (an antagonist of the σ-1 receptor) and 3) butyrophenones, such as the antipsychotic agent haloperidol that displays high affinity for both σ receptor subtypes.[19,34] Over the last two decades numerous groups have reported the development of high affinity σ-1 receptor ligands[34-42]—and of these, some have been labeled with radioisotopes (FIG. 1) for use in positron emission tomography (PET) studies.

Examining σ-1 receptors in living subjects with PET is an important step towards understanding the receptor's functional role and involvement in disease. PET radioligands specific for σ-1 receptors could potentially provide a non-invasive means of 1) visualizing and investigating the machinery of these sites, 2) assessing receptor occupancy (to help determine optimal doses of therapeutic drugs), 3) early detection and staging of σ-1 receptor-related disease(s), and 4) monitoring therapeutic response. Some existing σ-1 receptor radioligands include: [$^{11}$C]SA4503,[43] [$^{18}$F]FM-SA4503,[44] [$^{18}$F]FPS,[45] [$^{18}$F]SFE,[46,47] [$^{18}$F]FBFPA,[48] [$^{18}$F]fluspidine[49] and [$^{11}$C]13[39] (FIG. 1). The high affinity σ-1 receptor radioligand [$^{11}$C]SA4503 has demonstrated promising results in rodents,[43] felines[50] and non-human primates,[51] and is currently the only σ-1 receptor radioligand being routinely used in clinical research;[52, 53] however, it is far from ideal for several reasons including its high non-specific binding, affinity for other sites such as emopamil binding protein (EBP),[54] and suboptimal kinetic profile (indicative of irreversible binding). The fluorinated derivative of [$^{11}$C]SA4503 (known as [$^{18}$F]FM-SA4503) has demonstrated similar disadvantages in rodents and non-human primates, and is yet to be evaluated in humans. The piperidine [$^{18}$F]FPS reported by Waterhouse and colleagues was evaluated in human subjects in 2003,[46, 55, 56] however it displayed unfavorable kinetics (due to its inability to reach transient equilibrium at 4 h p.i.). Following these results, a lower affinity fluoromethyl derivative of [$^{18}$F]FPS (known as [$^{18}$F]SFE) was developed in hope of rectifying the issue of irreversible binding.[46] Whilst [$^{18}$F]SFE exhibited a superior kinetic profile (cleared from rat brain with a 40% reduction in peak uptake over a 90 min period), it was found to have a lower selectivity ratio, and in fact blocking studies in rats using a selective σ-2 receptor compound resulted in a small yet noticeable reduction in [$^{18}$F]SFE uptake.[46] In 2005 Mach and colleagues reported the radiosynthesis of another piperidine derivative [$^{18}$F]FBFPA (affinity for σ-2 receptor/σ-1 receptor=44) and demonstrated its ability to bind σ-1 receptors in both rodent and rhesus monkey brain.[48] In 2010 the synthesis of a spirocyclic piperidine σ-1 receptor radioligand, [$^{18}$F]fluspidine, and its evaluation in mice was reported.[37, 49] Biodistribution results showed 40% reduction in brain [$^{18}$F]fluspidine uptake over 2 hours, indicating that it may display reversible binding; however, it is still in the early stages of evaluation. Moussa and colleagues published the radiosynthesis of a carbon-11 labeled N-benzyl piperazine σ-1 receptor ligand, [$^{11}$C]13, and its in vivo evaluation in *Papio hamadryas* baboons using PET imaging. Whilst [$^{11}$C]13 accumulated in sigma-1 rich regions of the brain and peripheral organs, it was found to display a low selectivity ratio (affinity for σ-2 receptor/σ-1 receptor=38) and also nanomolar affinity for 5-HT2B receptors.[39]

At present, there is still no highly selective σ-1 receptor radioligand labeled with fluorine-18 or carbon-11 available for clinical research.

BRIEF DESCRIPTION OF THE INVENTION

The present invention relates to compounds useful as sigma receptors of the following formula I:

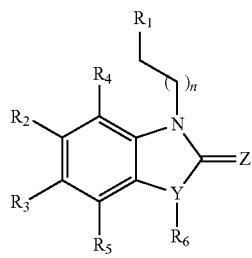

I

Wherein $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,3,4,5,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula I can be an optionally substituted $C_1$-$C_6$ alkylene, $C_1$-$C_6$ alkenylene or $C_1$-$C_6$ alkynylene group wherein the alkylene group can have inserted into its chain a $C_3$-$C_5$ cycloalkyl group, aromatic, and heterocyclic group.

The present invention further relates to compounds useful as sigma receptors of the following formula II:

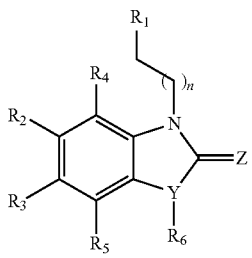

II

Wherein $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,4,5,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula II can be a substituted $C_1$-$C_6$ alkylene, $C_1$-$C_6$ alkenylene wherein the alkylene group can have inserted into its chain a $C_3$-$C_5$ cycloalkyl group, aromatic, and heterocyclic group.

The present invention relates to still yet further compounds useful as sigma receptors of the following formula III:

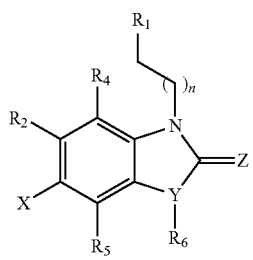

III

Wherein $R_1, R_{2,4,5,6}$ and "n" can be the options provided for formula II, above and wherein $X_1$ is halogen, or $C_1$-$C_4$ haloalkyl.

The present invention relates to a still yet further series of compounds useful as sigma receptors of the following formula IV:

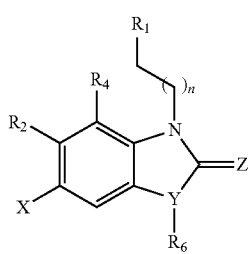

IV

Wherein $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,4,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula IV can be a substituted $C_1$-$C_6$ alkylene having the formula —(CHR$_x$—(CH$_2$)—CH$_2$)— wherein the —CHR$_x$— moiety is attached to $R_1$ and the alkylene group can have inserted into its chain a $C_3$-$C_5$ cycloalkyl group, aromatic, and heterocyclic group and wherein the $R_x$ is a $C_1$-$C_5$ straight chain or branched chain alkyl or a $C_1$-$C_4$ straight chain or branched chain haloalkyl.

The present invention further relates to compounds useful as sigma receptors of the following formula V:

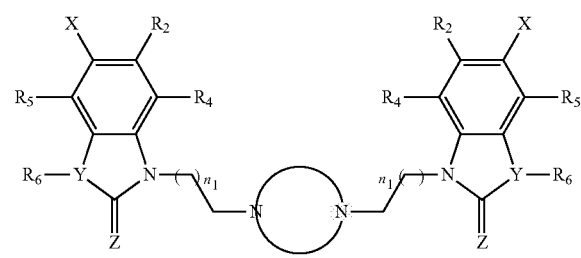

Wherein $R_{2,3,4,5,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be either CH, CH$_2$, O, S, OCH$_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The $R_1$ bridging moiety in the formula V can be an optionally substituted $C_1$-$C_6$ alkylene, $C_1$-$C_6$ alkenylene or $C_1$-$C_6$ alkynylene group wherein the alkylene group can have inserted into its chain a $C_3$-$C_5$ cycloalkyl group, aromatic, and heterocyclic group.

With the aim of synthesizing a new, selective PET radioligand for studying σ-1 receptors in living subjects, the present invention comprising another embodiment which relates to 18F fluorinated σ-1 receptor ligands from the benzothiazolone class of compounds as possible σ-1 receptor ligands. A lead compound from the benzothiazolone class of compounds originally reported by Yous and colleagues in 2005[42], SN56 (FIG. 1) from this class was reported to have high affinity (Ki=0.56 nM) and extremely high selectivity for the σ-1 receptor (Selectivity Ratio>1000). More recently, a tritiated version of SN56 ([³H]—SN56) was produced and assessed in vitro.[50] Results suggested [³H]—SN56 may be a favorable alternative to the σ-1 receptor radioligand [³H](+)-pentazocine. Applicants devised a strategy for modifying SN56 in a way that would allow incorporation of a fluorine-18 radiolabel without greatly altering the structure of the molecule in the hope of maintaining its high affinity and selectivity for the σ-1 receptor. The target molecule, 6-(3-fluoropropyl)-3-(2-(piperidin-1-yl)ethyl)benzo[d]thiazol-2(3H)-one (CM304) (FIG. 1) contains a fluoropropyl, in place of the propyl group on SN56. This is the only structural difference.

To the best of applicants' knowledge, no compounds from the benzothiazolone class have been evaluated as radioligands for σ-1 receptors. Since CM304 has an entirely different scaffold from other known σ-1 receptor radiotracers, and was born out of a class of highly selective σ-1 receptor compounds, applicants believe studies using this probe may generate valuable and novel information about the σ-1 receptor.

In this application, applicants report new ¹⁸F fluorinated σ-1 receptor ligands from the benzothiazolone class of compounds as possible σ-1 receptor ligands. Specifically, the applicant reports the synthesis of CM304, the radiosynthesis of [¹⁸F]FTC-146 and the preliminary evaluation of [¹⁸F]FTC-146 σ-1 receptor radioligand through the use of cellular uptake assays (using cells transfected with σ-1 receptor cDNA), mouse serum stability studies, and PET imaging of mice.

BRIEF DESCRIPTION OF THE FIGURES

FIG. 1—Selected sigma-1 receptor ligands and radioligands

Figure 17:
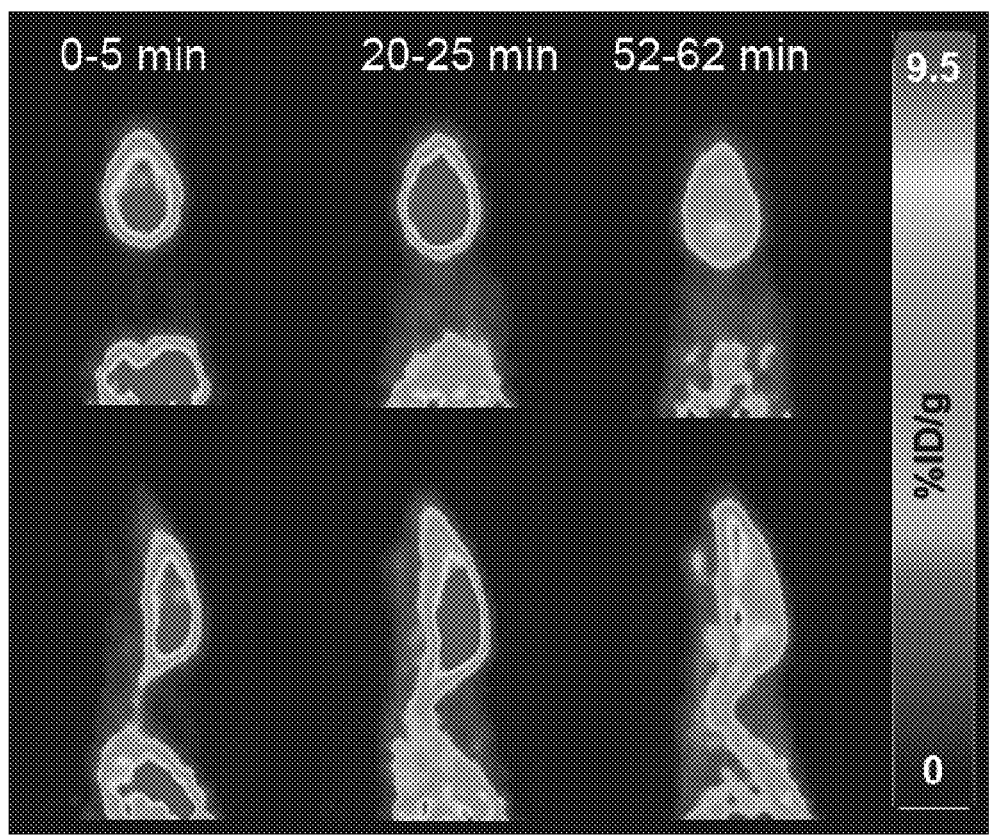

FIG. 17—[$^{18}$F]FTC-146 PET study in mice

Figure 18:
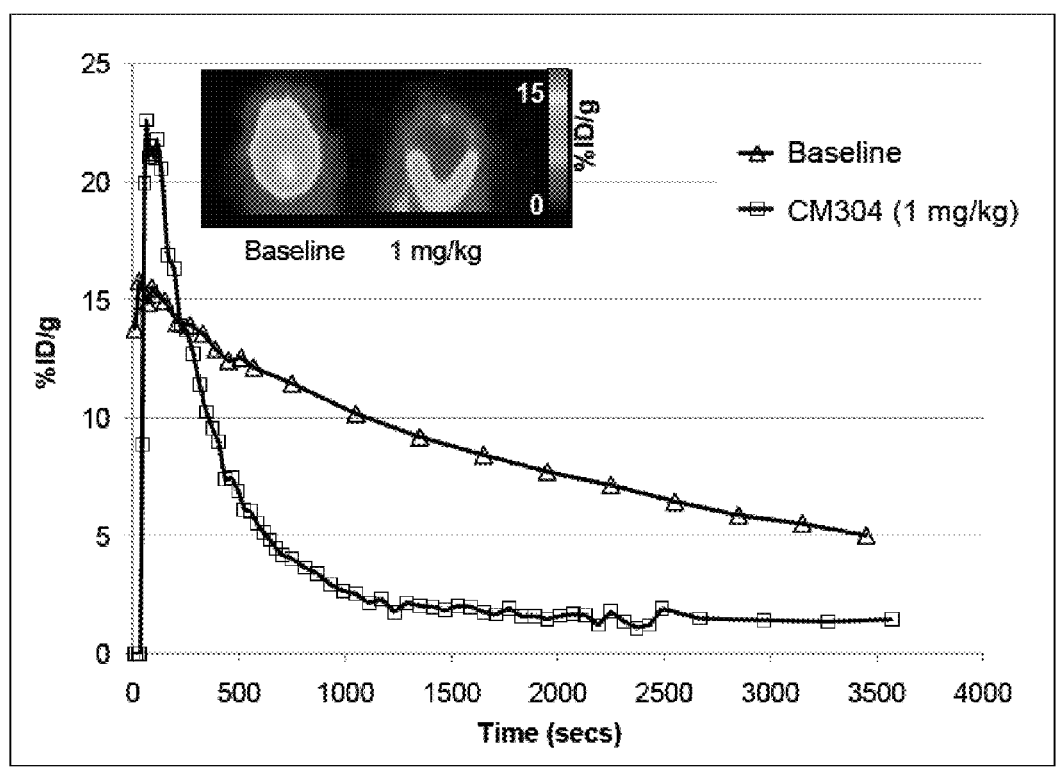

FIG. 18—[$^{18}$F]FTC-146 time activity curves. Time activity curves (TACs) representing accumulation of [$^{18}$F]FTC-146 in whole mouse brain as a function of time for both baseline (n=3) and blocking (n=3) PET imaging studies. Baseline studies involved i.v. administration of [$^{18}$F]FTC-146 (95-125 µCi), whereas blocking studies involved pre-treatment of mice with CM304 (1 mg/kg) 10 minutes prior to i.v. administration of [$^{18}$F]FTC-146 (95-125 µCi). Representative brain PET images (one baseline and one blocking) summed over the last 30 minutes are also shown.

DETAILED DESCRIPTION OF THE INVENTION

The generic structures of Formulae I, II, III, IV and V encompasses a diverse range of heterocycles. Embodiments within this genus, for example, include 2(3H)-benzoxazolone (Y=O, Z=O) and 2(3H)-benzothiazolone (Y=S, Z=O) compounds and the sigma receptor affinity shown by these heterocycles. The 2(3H)-benzoxazolone (BOA) and its bioisosteric surrogate 2(3H)-benzothiazolone (BTA) heterocycle is a bicyclic ring system which promotes high versatility in organic synthesis involving N-substitution (either N-alkylation or N-acylation) and aromatic ring electrophilic substitution reactions.

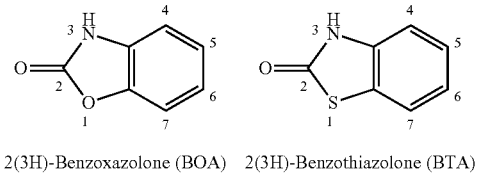

2(3H)-Benzoxazolone (BOA)    2(3H)-Benzothiazolone (BTA)

Chemical Structures of BOA and BTA

The present invention relates to compounds having the general formula I

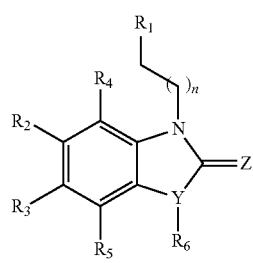

wherein $R_1$ can be a radical of an optionally substituted C-4 to C-7 N-containing heterocycle or a radical of an optionally substituted cyclic or acyclic tertiary amine, or isoindoline-1,3-dione $R_{2,3,4,5,6}$ can each independently be any one or combinations of the following moieties, cyano, nitro, acyl, alkyl, amido, azido, isothiocyanates, isocyanates, optionally substituted anilino, halogens, ethers, sulfonamides, thioacyl, nitro, aromatic, heterocyclic, olefinic, acetylene, deuterium, or tritium; Y can be either CH, CH$_2$, O, S, OCH$_2$, N—R, N—Ar, C—R, C—Ar; Z can be either H, O, S, S—R or NR. R groups can be either H, aryls, alkyls, or cycloalkyls; "n" can be 1 to 5 carbons in length and stereoisomers, functional analogs, and pharmaceutically acceptable salts thereof and wherein the moiety bridging $R_1$ and N can be optionally substituted alkylene, optionally substituted alkenylene or optionally substituted alkynylene and where the alkylene group can include an inserted C$_3$-C$_5$ cycloalkyl group, aromatic and heterocycle group.

The optionally substituted N-containing heterocyclic radical can be for example optionally substituted piperidine, optionally substituted tetrahydropiperidine, optionally substituted piperazine, optionally substituted tetrahydropyridine, optionally substituted azepanes or optionally substituted tetrahydroisoquinoline in which the optional substituents are on the aromatic moiety.

The present invention further relates to compounds useful as sigma receptors of the following formula II:

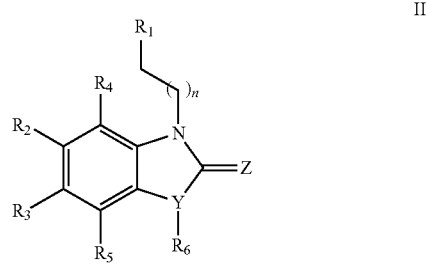

Wherein $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,4,5,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be either CH, CH$_2$, O, S, OCH$_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula II can be a substituted C$_1$-C$_6$ alkylene, C$_1$-C$_6$ alkenylene wherein the alkylene group can have inserted into its chain a C$_3$-C$_5$ cycloalkyl group, aromatic, and heterocyclic group.

Formulae I and II differ from each other only in the definition of the moiety bridging R1 and N.

The present invention relates to still yet further compounds useful as sigma receptors of the following formula III:

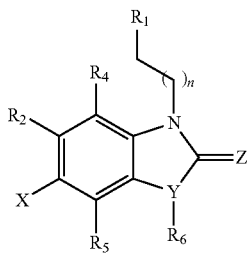

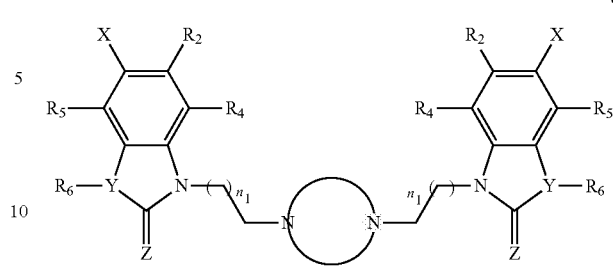

Wherein $R_1, R_{2,4,5,6}$ and "n" can be the options provided for formula II, above and wherein $X_1$ is halogen, or $C_1$-$C_4$ haloalkyl.

The present invention relates to a still yet further series of compounds useful as sigma receptors of the following formula IV:

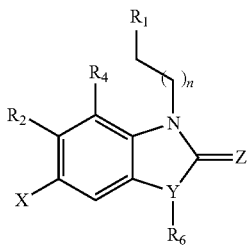

Wherein $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,4,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula IV can be a substituted $C_1$-$C_6$ alkylene having the formula —($CHR_x$—($CH_2$)—$CH_2$)— wherein the —$CHR_x$— moiety is attached to $R_1$ and the alkylene group can have inserted into its chain a $C_3$-$C_5$ cycloalkyl group, aromatic, and heterocyclic group and wherein the $R_x$ is a $C_1$-$C_4$ straight chain or branched chain alkyl or a $C_1$-$C_4$ straight chain or branched chain haloalkyl.

The present invention relates to compounds useful as sigma receptors of the following formula V:

Wherein $R_{2,3,4,5,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The $R_1$ bridging moiety in the formula V can be an optionally substituted $C_1$-$C_6$ alkylene, $C_1$-$C_6$ alkenylene or $C_1$-$C_6$ alkynylene group wherein the alkylene group can have inserted into its chain a $C_3$-$C_5$ cycloalkyl group, aromatic, and heterocyclic group.

Exemplary compounds of the invention can be of the general formulae shown below in which n=1-5:

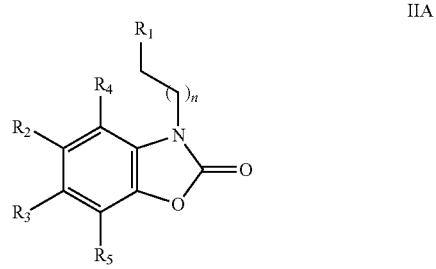

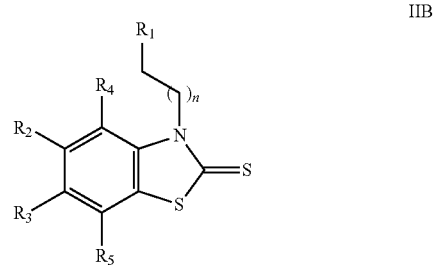

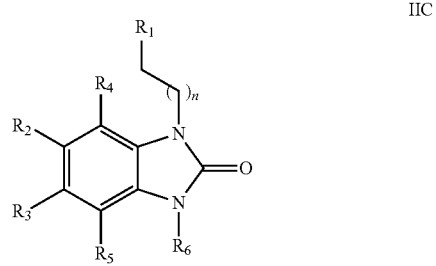

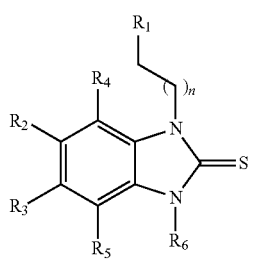
IID
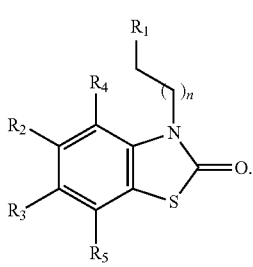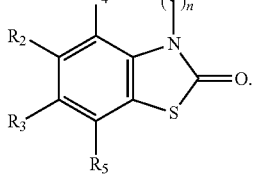
IIE
Further exemplary compounds of the invention can be of the general formulae shown below in which n=1-5:
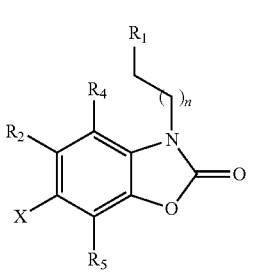
IIIA
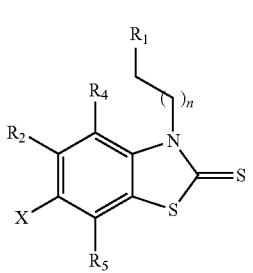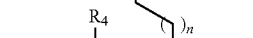
IIIB
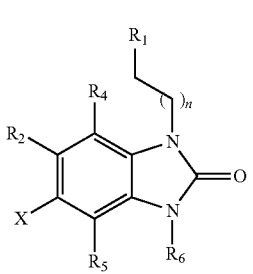
IIIC
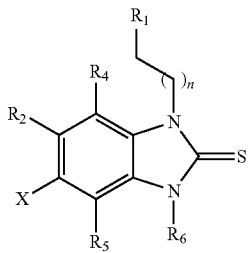
IIID
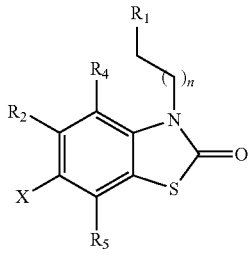
IIIE
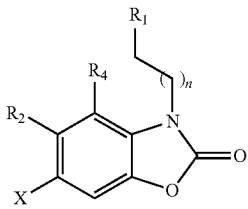
IVA
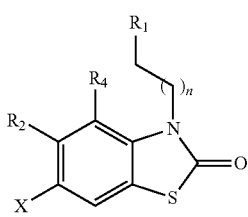
IVB
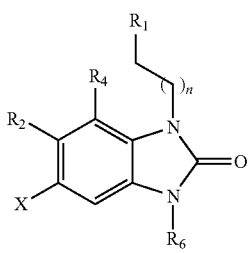
IVC
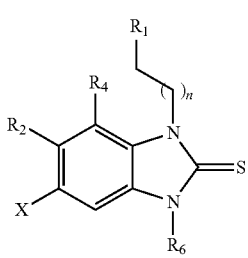
IVD

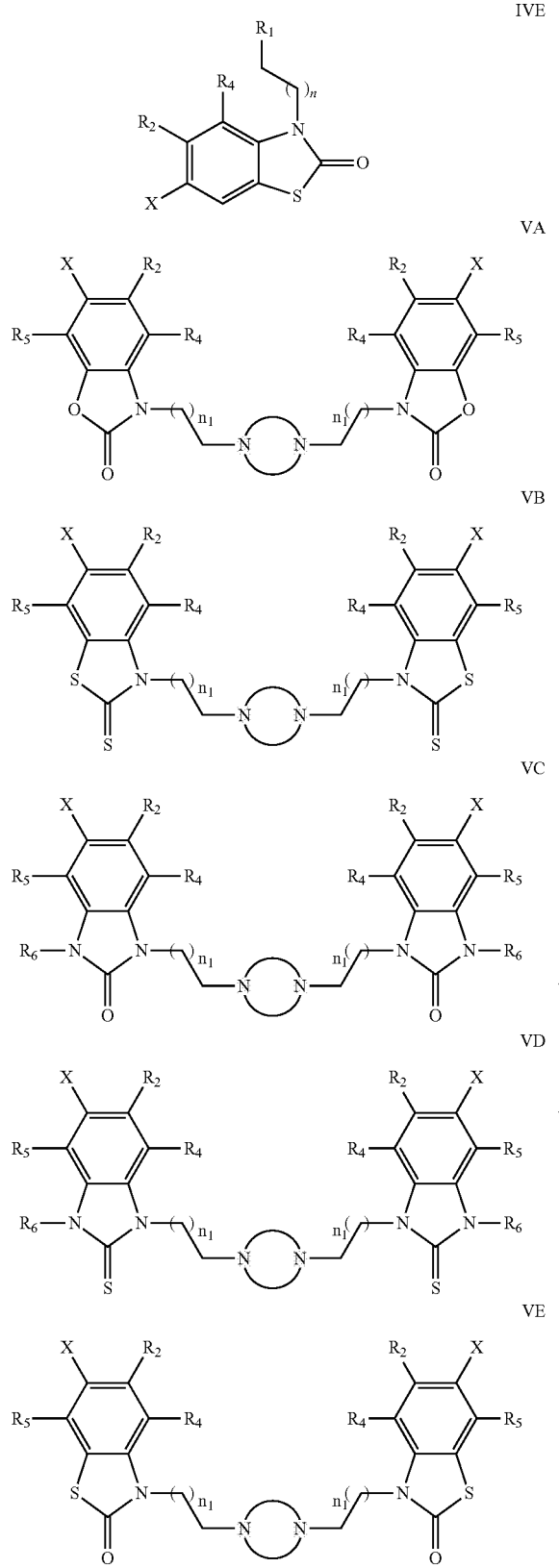

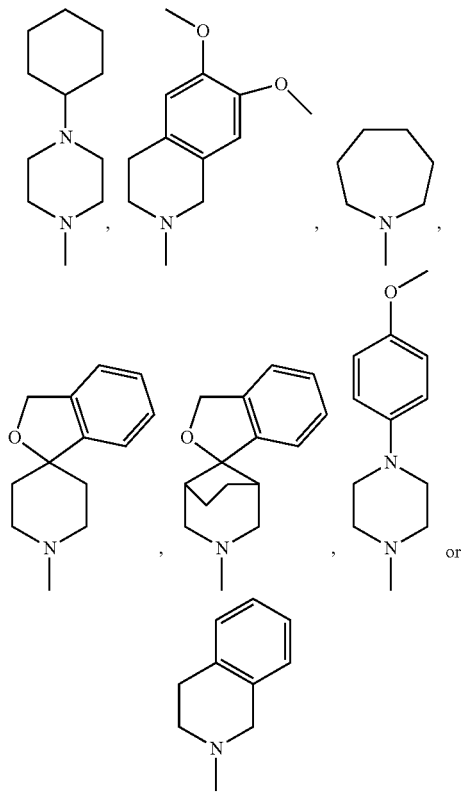

Other exemplary compounds of the invention are compounds where Y=O and Z=O; or Y=S and Z=S; or where Y=CH$_2$ or Y=CH.

$R_1$ for example is optionally substituted

DEFINITIONS OF TERMS

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, azido, isothiocyanate, isocyanate, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may contain one or more O, S, S(O), or S(O)$_2$ atoms. Examples of "alkyl" as used herein include, but are not limited to, methyl, n-butyl, t-butyl, n-pentyl, isobutyl, and isopropyl, and the like.

As used herein, the term haloalkyl refers to a straight or branched chain alkyl having one to four carbon atoms in which at least one H up to all of the H's of the alkyl is substituted with a halo moiety wherein halo includes fluoro, chloro, bromo or iodo.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkylene" group may contain one or more O, S, S(O), or S(O)$_2$ atoms. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may contain one or more O, S, S(O), or S(O)$_2$ atoms.

As used herein, the term "alkenylene" refers to a straight or branched chain divalent hydrocarbon radical having from two to ten carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenylene" group may contain one or more O, S, S(O), or S(O)$_2$ atoms. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may contain one or more O, S, S(O), or S(O)$_2$ atoms.

As used herein, the term "alkynylene" refers to a straight or branched chain 5 divalent hydrocarbon radical having from two to ten carbon atoms and one or more carbon-carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynylene" group may contain one or more O, S, S(O), or S(O)$_2$ atoms. Examples of "alkynylene" as used herein include, but are not limited to, ethyne-1,2-diyl, propyne-1,3-diyl, and the like.

As used herein, "cycloalkyl" refers to an alicyclic hydrocarbon group optionally possessing one or more degrees of unsaturation, having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to a non-aromatic alicyclic divalent hydrocarbon radical having from three to twelve carbon atoms and optionally possessing one or more degrees of unsaturation, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a three to twelve-membered heterocyclic ring optionally possessing one or more degrees of unsaturation, containing one or more heteroatomic substitutions selected from S, SO, SO$_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, tetrahydropyridine, hexahydroazepine and the like.

As used herein, the term "heterocyclyl containing at least one basic nitrogen atom" refers to a "heterocyclic" or "heterocyclyl" group as defined above, wherein said heterocyclyl group contains at least one nitrogen atom flanked by 20 hydrogen, alkyl, alkylene, or alkylyne groups, wherein said alkyl and/or alkylene groups are not substituted by oxo. Examples of "heterocyclyl containing at least one basic nitrogen atom" include, but are not limited to, piperazine-2-yl, pyrrolidine-2-yl, azepine-4-yl,

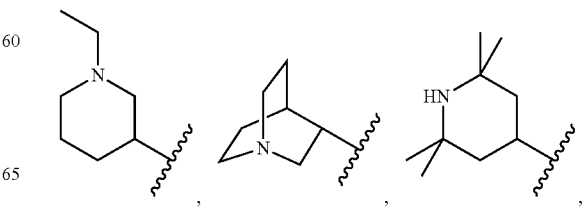

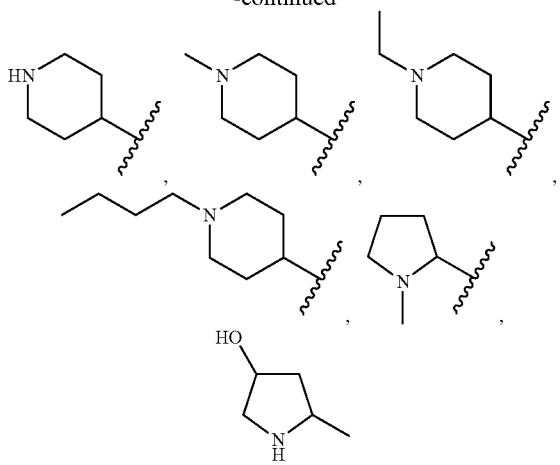

and the like.

As used herein, the term "heterocyclylene" refers to a three to twelve-membered heterocyclic ring diradical optionally having one or more degrees of unsaturation containing one or more heteroatoms selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-diyl, and the like.

As used herein, the term "aryl" refers to a benzene ring or to an optionally substituted benzene ring system fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy optionally substituted by acyl, mercapto, azido, isothiocyanate, isocyanate, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perluoroalkyl, multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower periluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, halo includes fluoro, bromo and iodo.

Initial efforts were focused on incorporating a good directionality by implying side-chains on a rigid template using conventional simple synthetic methodology. Exploring the effects of linker length between two hydrophobic regions for sigma receptor affinity led to the synthesis of 2 to 6 carbon linkers of 2(3H)-benzoxazolones ligands and 2(3H)-benzothiazolones compounds.

The in vitro receptor binding affinities of the initial series of compounds of formulae II and III investigated in rat brain homogenates at σ-1 and σ-2 subtypes are summarized in tables 1 and 2.

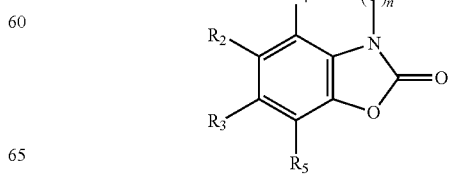

TABLE 1

Initial series 2(3H)-benzoxazolones to explore the effects of linker length on sigma receptor affinity

| Compd. | R₁ | R₂-R₅ | n | σ-1 ($K_i$, nM) | σ-2 ($K_i$, nM) | σ-1/σ-2 |
|---|---|---|---|---|---|---|
| CM-129 | -N(piperazine)N-cyclohexyl | H | 2 | 6.90 ± 0.37 | 5.43 ± 0.78 | 1.3 |
| CM-124 | -N(piperazine)N-cyclohexyl | H | 3 | 5.22 ± 1.11 | 8.74 ± 2.30 | 0.6 |
| CM-121 | -N(piperazine)N-cyclohexyl | H | 4 | 11.3 ± 1.25 | 1.83 ± 0.17 | 6.2 |
| CM-126 | -N(piperazine)N-cyclohexyl | H | 5 | 10.5 ± 2.52 | 5.89 ± 1.31 | 1.8 |
| SN-48 | -N(piperazine)N-cyclohexyl | H | 6 | 4.60 ± 1.08 | 3.06 ± 0.45 | 1.5 |

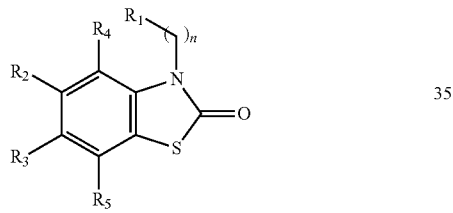

TABLE 2

Initial series 2(3H)-benzothiazolones to explore the effects of linker length on sigma receptor affinity

| Compd. | R₁ | R₂-R₅ | n | σ-1 ($K_i$, nM) | σ-2 ($K_i$, nM) | σ-1/σ-2 |
|---|---|---|---|---|---|---|
| SN-97 | -N(piperazine)N-cyclohexyl | H | 2 | 4.66 ± 0.74 | 2.25 ± 0.37 | 2.1 |
| SN-98 | -N(piperazine)N-cyclohexyl | H | 3 | 5.61 ± 0.74 | 3.05 ± 0.41 | 1.84 |
| CM-145 | -N(piperazine)N-cyclohexyl | H | 4 | 4.17 ± 0.62 | 0.39 ± 0.06 | 10.69 |
| SN-99 | -N(piperazine)N-cyclohexyl | H | 5 | 4.98 ± 0.42 | 2.44 ± 0.26 | 2.04 |

TABLE 2-continued

Initial series 2(3H)-benzothiazolones to explore the effects of linker length on sigma receptor affinity

| Compd. | R₁ | R₂-R₅ | n | σ-1 (K$_i$, nM) | σ-2 (K$_i$, nM) | σ-1/σ-2 |
|---|---|---|---|---|---|---|
| SN-102 | -N(piperazine)N-cyclohexyl | H | 6 | 6.55 ± 0.25 | 1.49 ± 0.18 | 4.40 |

CM121 showed a six fold preference for the σ-2 subtype, suggesting that a four methylene spacer between the piperazine ring and the heterocycle may favor σ-2 affinity (Table 1, Scheme 1). During further SAR studies, compound CM170 was found to have an 11 fold preference for the σ-2 subtype, suggesting a 4-fluoropiperazine moiety may favor σ-2 affinity (Scheme 1). Additionally, CM142 having a 6-acetyl group in the 2(3H)-benzoxazolone heterocycle increased the preference for σ-2 receptors by 7 fold (Scheme 1).

Scheme 1: Sigma-2 selective ligands

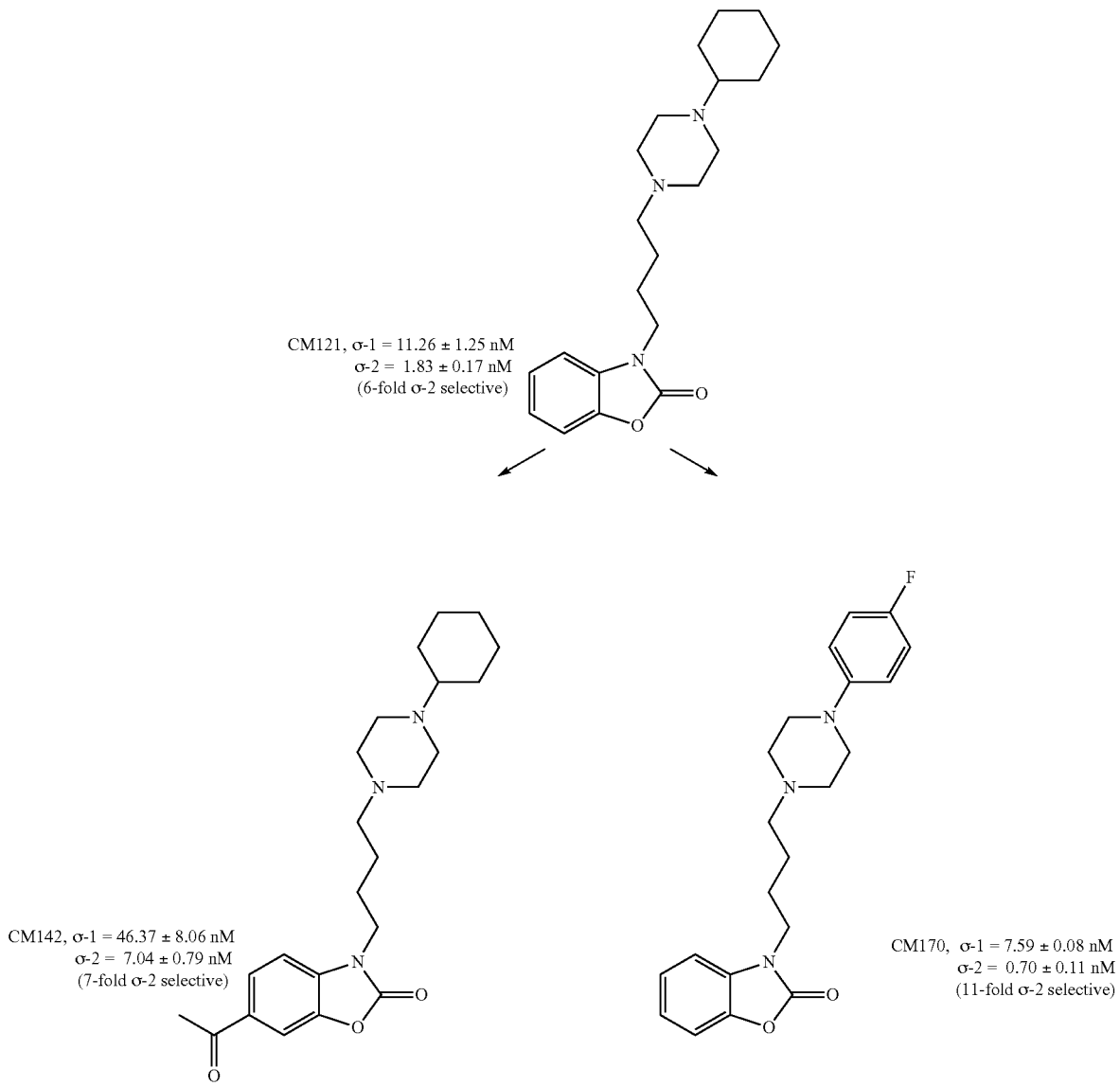

CM121, σ-1 = 11.26 ± 1.25 nM
σ-2 = 1.83 ± 0.17 nM
(6-fold σ-2 selective)

CM142, σ-1 = 46.37 ± 8.06 nM
σ-2 = 7.04 ± 0.79 nM
(7-fold σ-2 selective)

CM170, σ-1 = 7.59 ± 0.08 nM
σ-2 = 0.70 ± 0.11 nM
(11-fold σ-2 selective)

Interestingly, SN79 (Scheme 2) showed the high selectivity (>16,500 fold) for the σ-2 subtype suggesting that a four methylene linker, a 6-acetyl group in the 2(3H)-benzoxazolone heterocycle and a 4-fluoropiperazine moiety favor σ-2 affinity over the σ-1 subtype.

Scheme 2:

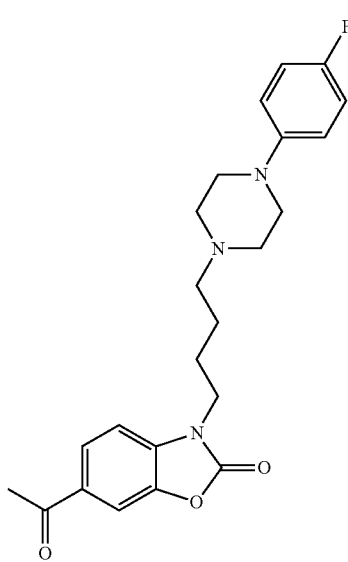

Compound SN79

SN79,   σ-1 = >100,000 nM
        σ-2 = 6.06 ± 0.74 nM
        (>16500 fold σ-2 selective)

When tested on select non-sigma binding sites in rat brain homogenates (Table 3), compound SN79 exhibited weaker interactions, confirming preferential affinity for sigma receptors.

TABLE 3

Non-sigma binding affinity of SN79

| Monoamine transporters | $K_i$, nM | Other Receptors | $K_i$, nM |
|---|---|---|---|
| DAT | 2615 ± 62 | Opioid | >10,000 |
| SERT | 159 ± 15 | NMDA | >10,000 |
| NET | 177 ± 14 | Dopamine ($D_2$) | >10,000 |
|  |  | 5-$HT_2$ | 320 ± 16 |

Compound SN79 was investigated for in vivo antagonizing effects in cocaine treated mice. Pretreatment of mice with SN79 led to a significant attenuation of cocaine-induced convulsions, locomotor activity and behavioral sensitization as seen in FIGS. 2-5. These data further demonstrate that compound SN79, acting through σ-2 receptors is able to significantly attenuate both the acute effects of cocaine as well as its chronic effects.

In addition to compounds exhibiting selectivity for the σ-2 receptor, compounds from this same series have demonstrated high affinity for both subtypes. Compound CM156 (Scheme 3), where the 2-oxo is replaced with a sulfur, demonstrated the highest affinity for both subtypes and was therefore examined in several non-sigma binding assays as shown in table 4. CM156 had much weaker affinity for other proteins of interest, confirming preferential affinity for sigma receptors.

Scheme 3:

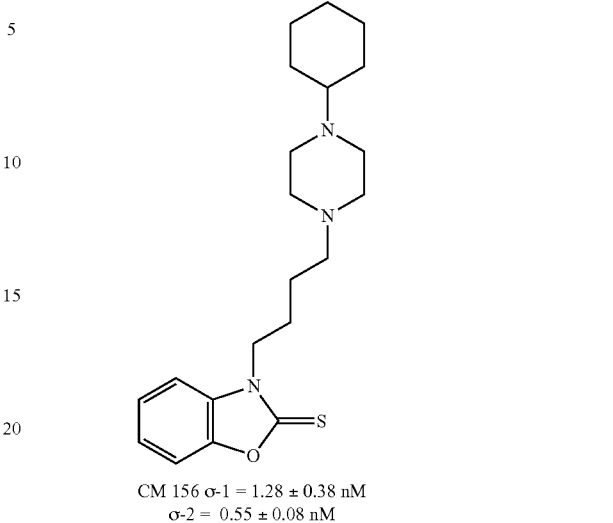

Compound CM156

CM 156 σ-1 = 1.28 ± 0.38 nM
        σ-2 = 0.55 ± 0.08 nM

TABLE 4

Non-sigma binding affinity of CM156

| Monoamine transporters | $K_i$, nM | Other Receptors | $K_i$, nM |
|---|---|---|---|
| DAT | 1175 ± 10 | Opioid | >10,000 |
| SERT | 1402 ± 152 | NMDA | >10,000 |
| NET | >10,000 | Dopamine ($D_2$) | 1041 ± 9 |
|  |  | 5-$HT_2$ | 1326 ± 159 |

Figure 6:
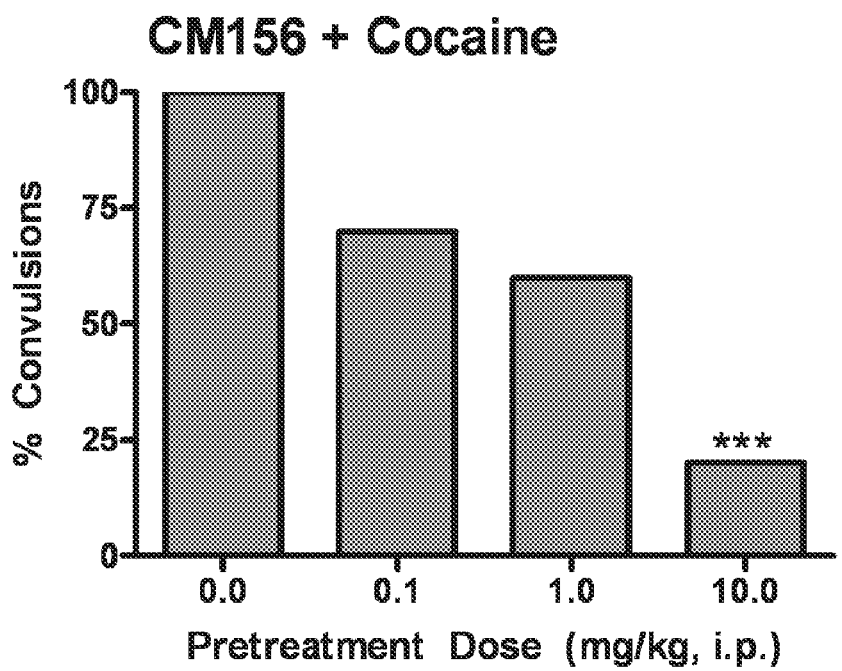
FIG. 6—CM156 attenuates the convulsive effects of cocaine (***P<0.005)
Figure 7:
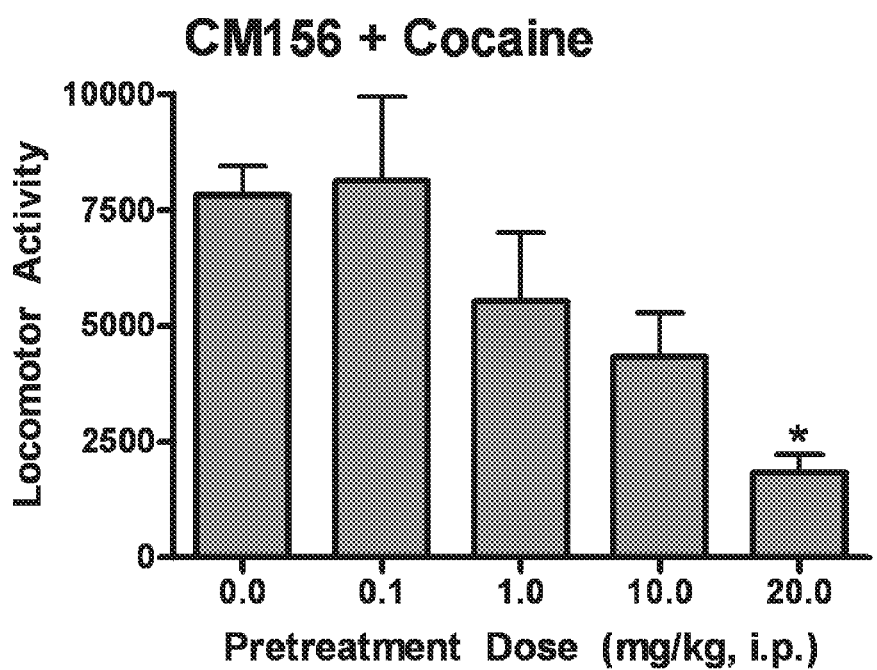
FIG. 7—CM156 pretreatment attenuates cocaine-induced locomotor activity (*P<0.05)
Figure 8:
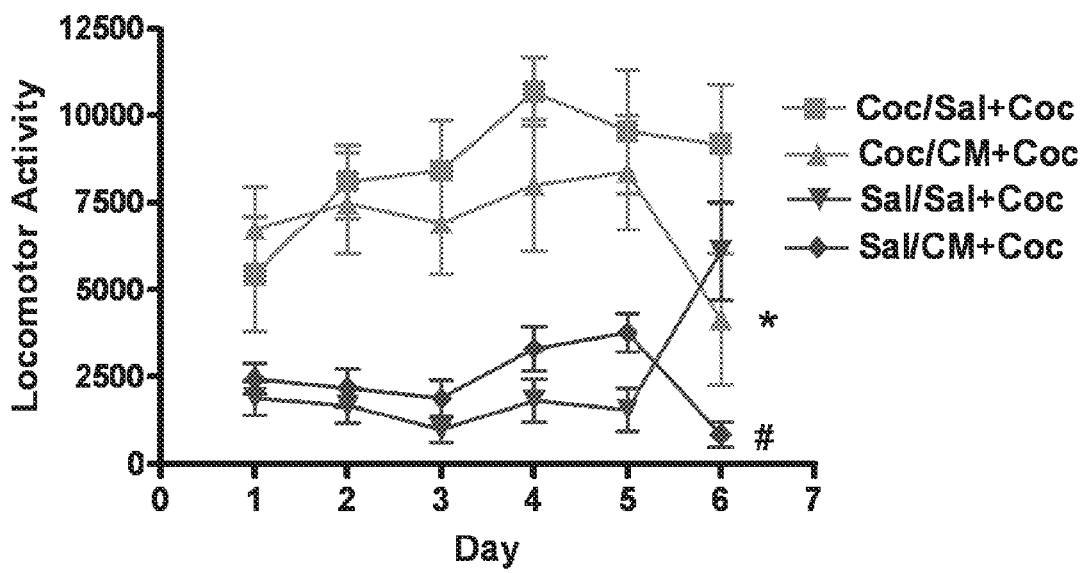
FIG. 8—CM156 pretreatment attenuates the expression of cocaine-induced sensitization (*P<0.05 vs sensitized, #P<0.05 vs acute cocaine)
Figure 9:
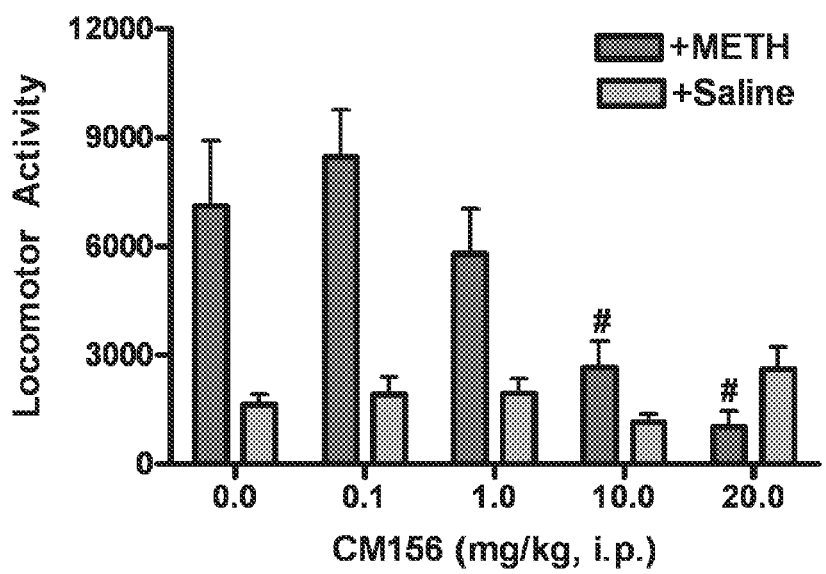
FIG. 9—CM156 pretreatment attenuates methamphetamine-induced locomotor activity (#P<0.05)
Figures 10, 11:
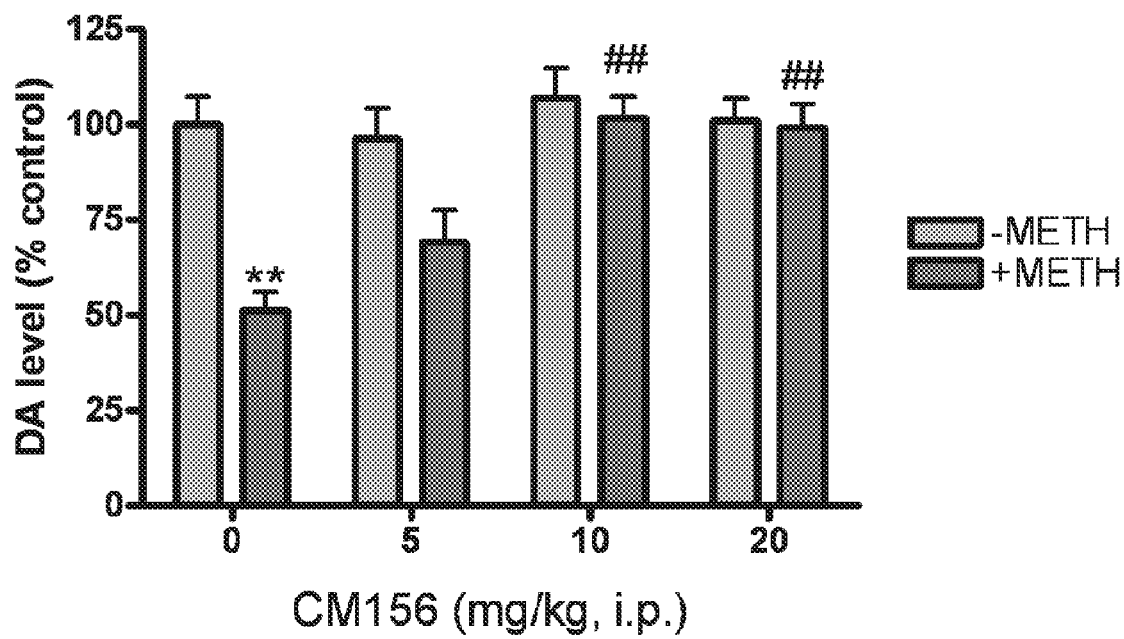
FIG. 10—CM156 pretreatment attenuates methamphetamine-induced dopamine depletions (**P<0.05, ##P<0.05)
FIG. 11—Table 1: Metabolic stability of AZ_66 by Rat liver microsomes (1 mg/ml)
Figures 12, 13, 14:
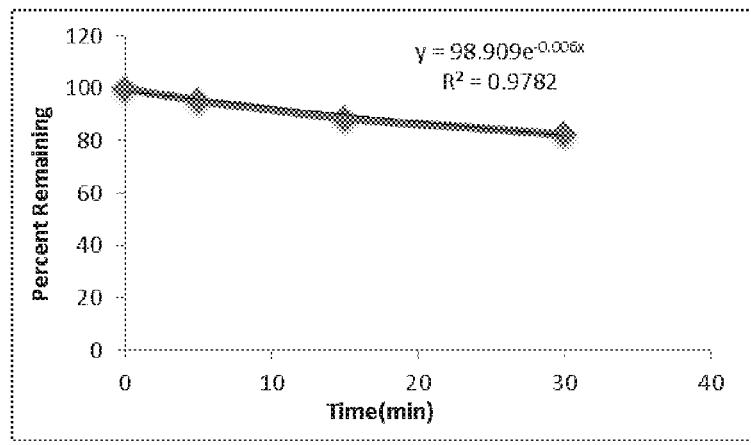
FIG. 12—Metabolic stability of AZ_66 by Rat liver microsomes (1 mg/ml)
FIG. 13—Table 2: In vitro Half-life and Intrinsic clearance
FIG. 14—Table 3: Incubation of CM_156 (10 μM) with rat liver microsomes (1 mg/ml)

Compound CM156 was further investigated in vivo for antagonizing effects in cocaine treated mice. Pretreatment of mice with CM156 led to a significant attenuation of cocaine-induced convulsions, locomotor activity and behavioral sensitization as seen in FIGS. 6-8. Compound CM156 was additionally investigated for its ability to attenuate methamphetamine-induced locomotor stimulation and neurotoxicity in mice. As seen in FIGS. 9 and 10, CM156 attenuated the locomotor stimulant effects of methamphetamine as well as the neurotoxic effects resulting from methamphetamine exposures. Together, these data demonstrate that CM156 with high affinity for both a subtypes can mitagate a variety of drug-induced effects, both from cocaine and methamphetamine, in vivo.

Metabolic Stability of AZ_66 in Rat Liver Microsomes
  AIM: To study the metabolic stability of AZ_66 in Rat liver microsomes.
  Analytical Method Set Up
  For the metabolism studies of AZ_66, an isocratic method was developed using UPLC/MS/MS.
  Chromatographic Conditions
  Mobile phase A: 0.3% Formic acid in water, 10 mM Ammonium Formate (50%)
  Mobile phase B: 0.1% Formic acid in Methanol (50%)
  Column: Atlantis dC18 (2.1×50 mm, 5 µm)
  Flow rate: 0.2 mL/min
  Injection volume: 10 µl
  Mass Parameters
  The detection of the analyte was carried out using ESI+ve mode. The MS conditions were as follows: Capillary voltage 4.88V, Cone voltage 46V, Extractor voltage 3V, RF lens voltage 0.5V. The source and Desolvation temperatures were 120° C. and 250° C. respectively, and the Desolvation and cone gas flows were 500 and 60 L/hr respectively. The selected mass-to-charge (m/z) ratio transition of AZ-66 ions [M+H]$^+$ used in the single ion reaction (SIR) was m/z: 406.2

Method

Metabolic stability of AZ_66 (1 μM) was performed in Ammonium acetate buffer (50 mM, pH 7.4) with Rat liver microsomes (0.5 mg) at 37° C. in 0.5 ml of incubation mixture. The incubation mixture composed of Ammonium acetate buffer (50 mM, pH 7.4), Magnesium chloride (3 mM), NADPH regenerating system consisting of NADP (1 mM), glucose-6-phosphate (5 mM), and glucose-6-phosphate dehydrogenase (1 Unit/mL). The Substrate and microsomes were pre incubated at 37° C. for 5 min before starting the reaction. The reactions were started by the addition of regenerating system and carried out at 37° C. in a shaking water bath for 60 min. The incubations were stopped by adding equal volume of ice cold acetonitrile at predetermined time points (0, 5, 15, 30, 60 min). The samples were centrifuged for 10 min at 4° C. and the supernatant was injected in to UPLC/MS/MS. Control incubation without NADPH was also performed and these served as 100% value. All microsomal incubations were conducted using the same lot of microsomes.

Additional Controls

Additional incubations were performed using rat liver microsomes at same experimental conditions with CM_156 (10 μM). This served as a positive control to determine if the test system used in this study were metabolically competent. In vitro half-life and CLint: The percent of the parent compound remaining is plotted versus time. The slope of the line gives the rate constant k for the disappearance of parent compound, from which an in vitro $t_{1/2}$ can be calculated. CLint can be calculated using the following formula $$CLint = k(\text{min}^{-1}) \times \frac{[V](L)}{[P](\text{mg})} = (L/\text{mg} \times \text{min})$$

[V] is the incubation volume in μl and [P] is the amount of microsomal protein in the incubation.

Results

The metabolism of AZ_66 was investigated in vitro using rat liver microsomes for 60-min. The estimated $t_{1/2}$ for disappearance of AZ_66 in rat liver microsomes was 115.56±15 min. Linear part of the Concentration vs Time graph was selected for the half-life calculations i.e. from 0-30 min. The estimated CLint from microsomes was 0.006 ml/min/mg. The CLint whole liver of AZ_66 1 μM was 0.002434 L/min. There is no loss of substrate in the absence of cofactor indicating that the loss of AZ_66 is through metabolism by NADPH-dependent enzymes.

AZ_66 was found to be stable in rat liver microsomes even after 60 min of incubation. Microsomes metabolized about 25% of the added substrate by 60 min. The results revealed that the metabolism was slow and continued at a linear rate for 30 min with an apparent departure from linearity after 30 min. The deviation from linearity may be due to limiting amounts of substrate or known organic and inorganic cofactors.

The substantial stability of the compound may be attributed to the C—F bond and oxygen in the thiazole ring. The other possible reason for higher stability could be the presence of methyl group preventing the N-dealkylation.

It may be concluded that the rate of metabolism could be decreased by incorporation of appropriate substituents at the primary sites of metabolism. See FIGS. 11, 12, 13, and 14.

The compounds of the present invention are for use as novel radioligands and agents for treatment of drugs of abuse including cocaine- and methamphetamine-induced abuse and toxicities.

EXPERIMENTAL

Chemical Synthesis of Novel σ Antagonists

Compounds can be modified in several positions to investigate the effects around the core structure on σ-1 and σ-2 affinities and activities. It has been demonstrated that one can substitute the template molecule through several synthetic routes. These routes which can be easily performed utilizing parallel synthesis methodology, can be easily varied to obtain multiple novel ligands. Initial studies focused on exploring the following changes to the molecules through parallel methodologies: 1) varying the methylene spacer between the tertiary amine and heterocycle; 2) modifying substituents to the piperazine nitrogen above the template; 3) modifying the piperazine ring to substitute piperidines, tetrahydropyridines, azepanes and diazepines; 4) modifying the order of heteroatoms in the heterocycle portion of the molecule as well as the connectivity pattern; and 5) substitution on the benzo portion of the heterocycle to probe the space and physicochemical requirements of the σ receptors.

Compounds were analyzed after purification using standard techniques (NMR, IR, LC/MS, HPLC) and converted into hydrochloride salts for water solubility. Final purity of compounds were achieved through melting points and elemental analysis. When necessary, X-ray crystallography was performed.

Syntheses of 2(3H)-benzoxazolones and 2(3H)-benzothiazolones were accomplished by multistep solution phase synthesis as shown Scheme 4. Synthesis involved simple base-mediated alkylation and Friedel-Craft's alkylation reactions.

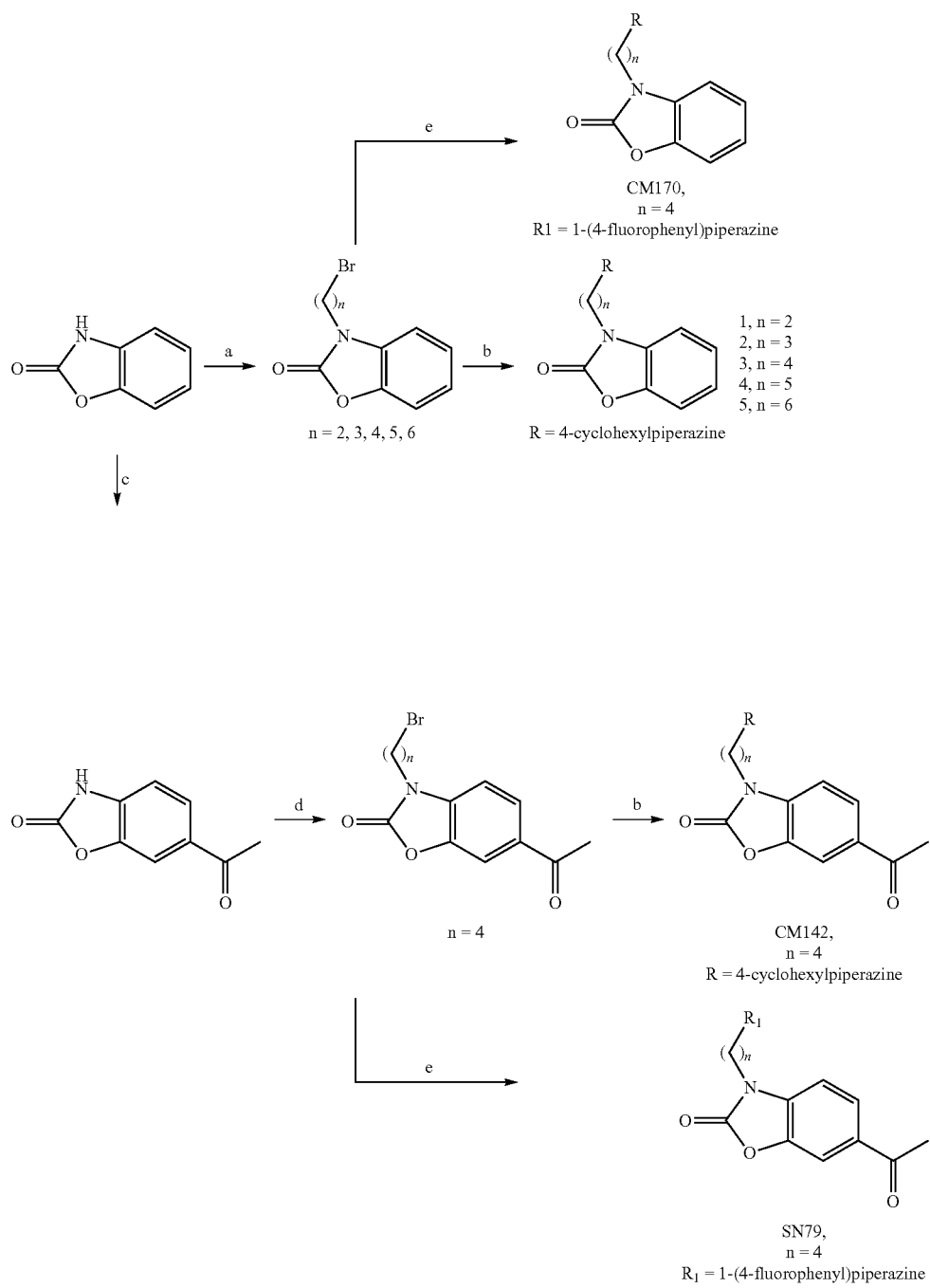
Scheme 4. Reagents and conditions: a) Dibromoalkane, $K_2CO_3$, DMF, 60° C., 2 h; b) 1-cyclohexylpiperazine, $K_2CO_3$, DMF, 60° C., 3 h; c) $(CH_3CO)_2O$, $AlCl_3$, 75° C., 4 h; d) 1,4-dibromobutane, $K_2CO_3$, DMF, 60° C., 2 h; e) 1-(4-fluorophenyl)piperazine, $K_2CO_3$, DMF, 60° C., 4 h Sigma Compounds—Synthetic Scheme

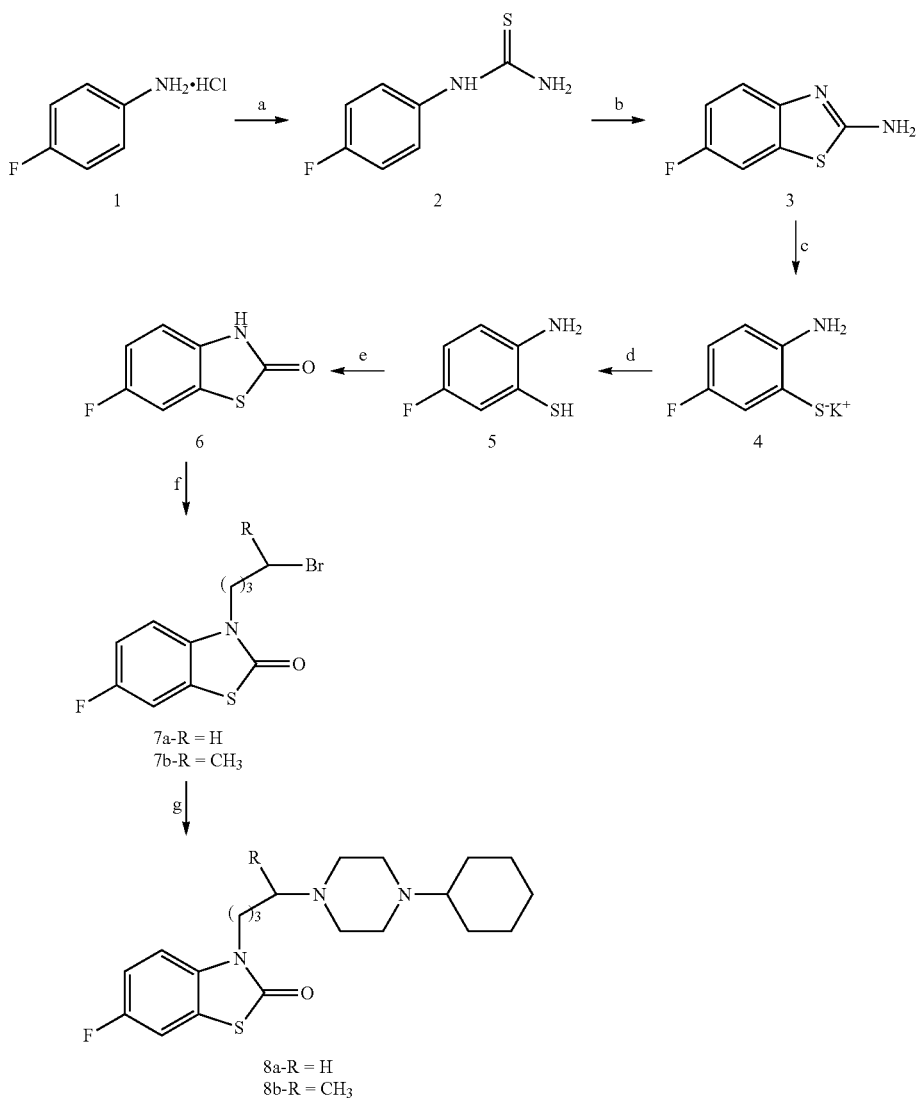

Scheme 5. Reagents and conditions: (a) NH$_4$SCN, H$_2$O, reflux, 4 h; (b) Br$_2$, CHCl$_3$, 1 h at 0° C., reflux, 2 h (c) KOH (d) Gl. acetic acid (e) Carbonyl 1,1' diimidazole, THF, reflux, 3 h; (f) 1,4 dibromoalkane, K$_2$CO$_3$, DMF, 60° C., 3 h; (g) cyclohexyl piperazine, K$_2$CO$_3$, TBAI, ACN, reflux, 6 h σ Receptor Assays Compounds were evaluated for σ-1 and σ-2 binding in rat brain homogenates. Twelve concentrations of each test ligand (0.001-1,000 nM) were incubated for 120 min at 25° C. in 50 mM Tris-HCl, pH 8.0 with 500 µg membrane protein, and 5 nM [$^3$H](+)-pentazocine (for σ$_1$ assays) or 3 nM [$^3$H]DTG plus 300 nM (+)-pentazocine (for σ$_2$ assays); non-specific binding was determined in the presence of 10 µM haloperidol. The assays were terminated with ice-cold 10 mM Tris-HCl, pH 8.0, followed by two washes through glass fiber filters that were pre-soaked for at least 30 min in 0.5% polyethyleneimine.

Non-σ Assays

Compounds were tested at various non-σ target sites to evaluate selectivity because cocaine interacts with these sites (dopamine, serotonin and norepinephrine transporters) or historic "sigma" ligands interact with them (opioid, NMDA, dopamine D$_2$, 5-HT$_2$ receptors). The compounds were tested in competition binding assays using rat brain homogenates as previously published. Briefly, the radioligands to label the sites of interest and compounds to define non-specific binding were as follows: dopamine transporters (0.5 nM [$^3$H]WIN35,428, 50 µM cocaine), serotonin transporters (0.2 nM [$^3$H]paroxetine, 1.5 µM imipramine), norepinephrine transporters (0.5 nM [$^3$H]nisoxetine, 4 µM desipramine), opioid receptors (2 nM [$^3$H]bremazocine, 10 µM levollorphan), NMDA receptors (5 nM [$^3$H]TCP, 10 µM cyclazocine), dopamine D$_2$ receptors (5 nM [$^3$H](−)-sulpiride, 1 µM haloperidol), and 5-HT$_2$ receptors (2 nM [$^3$H]ketanserin, 1 µM mianserin). The results were reported as K$_i$ in nM. If after three independent replications of the assay, the 10,000 nM concentration of the compound did not display at least 30% inhibition of the radioligand, the affinity of the compound was reported as >10,000 nM.

Cocaine-Induced Convulsions

Male, Swiss Webster mice were pretreated (i.p.) with saline or compound (0.1-10 mg/kg), then challenged 15 min later with a convulsive dose of cocaine (70 mg/kg, i.p.).

Mice were observed for the next 30 min for convulsions, which were defined as a loss of righting reflexes for at least 5 sec combined with the presence of clonic limb movements or popcorn jumping. Fisher's exact test was used to determine whether the effect produced by pretreatment with a particular drug dose differed significantly from pretreatment with the saline control.

Cocaine-Induced Locomotor Activity

Male, Swiss Webster mice were acclimated to the treatment room and then to the chambers of the automated activity monitoring system (San Diego Instruments, San Diego, Calif.). They were injected (i.p.) with saline or compound (0.1-20 mg/kg), then challenged 15 min later with cocaine (20 mg/kg, i.p.) or saline (i.p). The total locomotor activity (ambulatory, fine and rearing movements) of the mice was recorded for the next 30 min as the number of disruptions made by them in the 16×16 photobeam grid of their testing chamber.

Development of Sensitization

Male, Swiss Webster mice were acclimated as detailed above. For five consecutive days (Days 1-5), the mice were pretreated (i.p.) with saline or compound (0.1-20 mg/kg), then challenged 15 min later with cocaine (10 mg/kg, i.p.) or saline (i.p.). The total locomotor activity (ambulatory, fine and rearing movements) of the mice was recorded for the next 30 min as the number of disruptions made by them in the 16×16 photobeam grids of their testing chamber on each of the five days. A 10 day drug-free period followed. On Day 15, all of the mice were pre-administered (i.p.) saline followed by cocaine (10 mg/kg, i.p.), and locomotor activity quantified for the next 30 min.

Expression of Sensitization

Male, Swiss Webster mice were acclimated as detailed above. For five consecutive days (Days 1-5), the mice were pretreated (i.p) with saline, then challenged 15 min later with cocaine (10 mg/kg, i.p.). The total locomotor activity (ambulatory, fine and rearing movements) of the mice was recorded for the next 30 min. A 10 day drug free period followed and on Day 15, the mice were administered saline (i.p.) or compound (0.1-20 mg/kg), followed 15 min later with cocaine (10 mg/kg, i.p.). Locomotor activity was then recorded for the next 30 min.

Methamphetamine-Induced Locomotor Activity

Male, Swiss Webster mice were acclimated as detailed above. They were injected (i.p.) with saline or compound (0.1-20 mg/kg), then challenged 15 min later with methamphetamine (1 mg/kg, i.p.) or saline (i.p). The total locomotor activity (ambulatory, fine and rearing movements) of the mice was recorded for the next 30 min as the number of disruptions made by them in the 16×16 photobeam grids surrounding their testing chambers.

Methamphetamine-Induced Dopamine Depletions

Male, Swiss Webster mice were injected (i.p.) with saline or compound (0-20 mg/kg), followed 15 min later with either saline (-METH) or methamphetamine (5 mg/kg) at 2 hr intervals, a total of four times. Striatal dopamine levels were measured one week later.

The following represents compounds which are within the scope of the invention and which were prepared and tested for activity. Also included are compounds which were prepared but not tested but which are expected to have activity similar to the prepared and tested compounds. Also included in the listing are compounds which can be prepared and which would be expected to have activities similar to those compounds which were prepared and tested.

| Compd. | Structure | Ki (nM) |
|---|---|---|
| SN-48 | 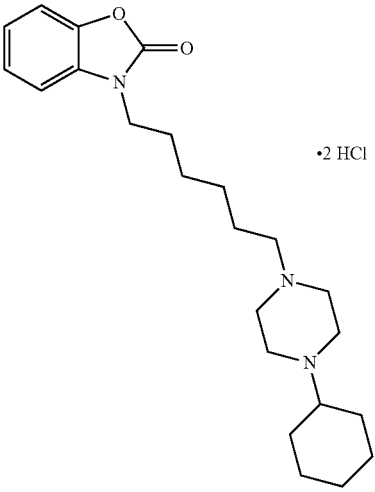 [SMILES: O=c1oc2ccccc2n1CCCCCCN1CCN(C2CCCCC2)CC1] •2 HCl | σ1 = 4.60 ± 1.08 σ2 = 3.06 ± 0.45 |

-continued
| Compd. | Structure | Ki (nM) |
|---|---|---|
| SN-55 | 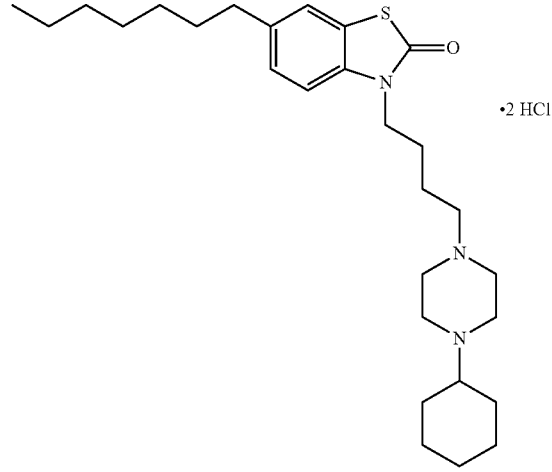 [SMILES: CCCCCCCc1ccc2c(c1)sc(=O)n2CCCCN1CCN(C2CCCCC2)CC1] ·2 HCl | σ1 = 34.12 ± 8.09<br>σ2 = 31.39 ± 6.87 |
| SN-57 | 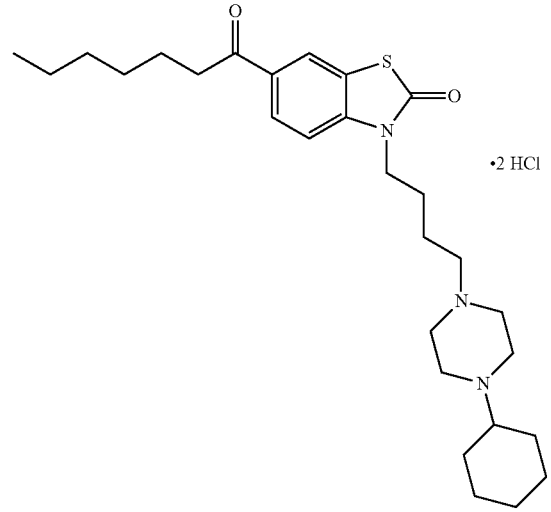 [SMILES: CCCCCCC(=O)c1ccc2c(c1)sc(=O)n2CCCCN1CCN(C2CCCCC2)CC1] ·2 HCl | σ1 = 43.76 ± 6.12<br>σ2 = 29.29 ± 2.83 |
| SN-60 | 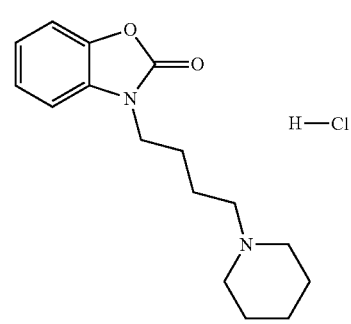 [SMILES: O=c1oc2ccccc2n1CCCCN1CCCCC1 ; Cl] H—Cl | σ1 = 12.06 ± 1.54<br>σ2 = 212.67 ± 11.81 |

-continued
| Compd. | Structure | Ki (nM) |
|---|---|---|
| SN-61 | 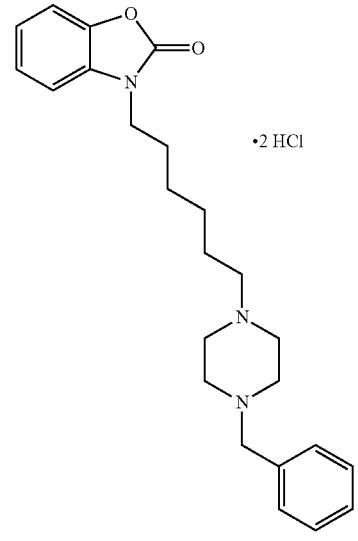 [SMILES: O=c1oc2ccccc2n1CCCCCCN1CCN(Cc2ccccc2)CC1] •2 HCl | σ1 = 4.68 ± 1.37<br>σ2 = 107.1 ± 32.59 |
| SN-71 | 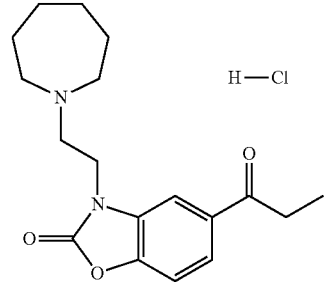 [SMILES: CCC(=O)c1ccc2oc(=O)n(CCN3CCCCCC3)c2c1 ; Cl] H—Cl | σ1 = 114.74 ± 25.91<br>σ2 = 2342 ± 229.80 |
| SN-72 | 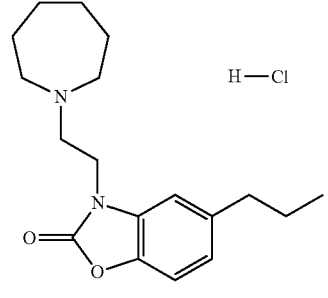 [SMILES: CCCc1ccc2oc(=O)n(CCN3CCCCCC3)c2c1 ; Cl] H—Cl | σ1 = 3.33 ± 0.41<br>σ2 = 1810.66 ± 83.76 |
| SN-78 | 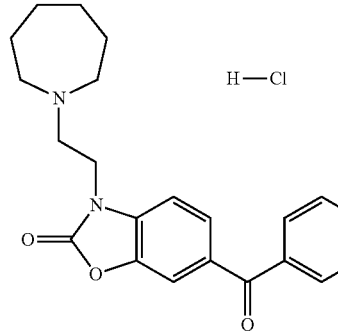 H—Cl | σ1 = 88.31 ± 8.59<br>σ2 = 859.66 ± 86.59 |

| Compd. | Structure | Ki (nM) |
|---|---|---|
| SN-79 | 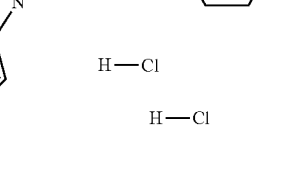 | σ1 = >100,000<br>σ2 = 6.06 ± 0.74 |
| SN-81 | 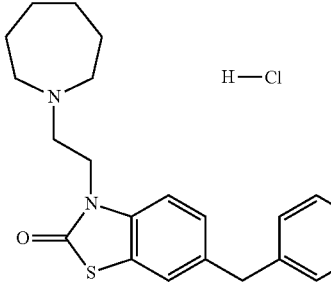 | σ1 = 7.42 ± 3.21<br>σ2 = 224.56 ± 46.88 |
| SN-97 | 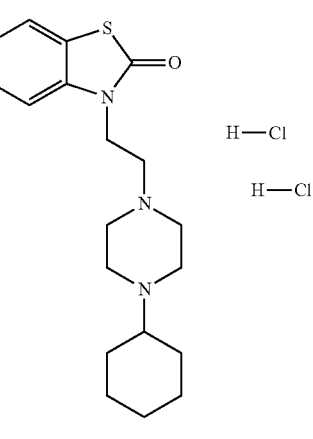 | σ1 = 4.66 ± 0.74<br>σ2 = 2.25 ± 0.37 |
| SN-98 | 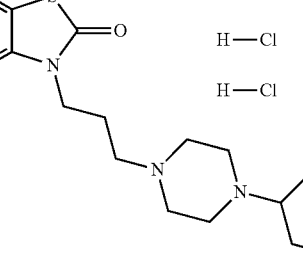 | σ1 = 5.61 ± 0.74<br>σ2 = 3.05 ± 0.41 |
| SN-99 | 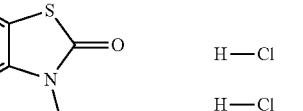 | σ1 = 4.98 ± 0.42<br>σ2 = 2.44 ± 0.26 |

| Compd. | Structure | Ki (nM) |
|---|---|---|
| SN-102 | 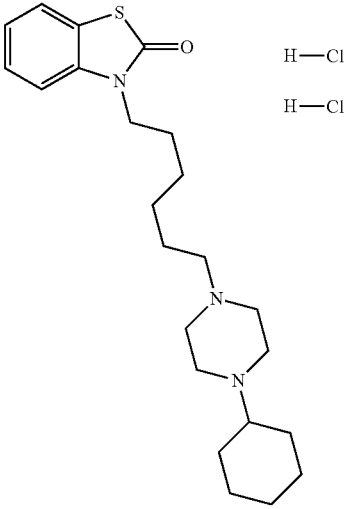 | σ1 = 6.55 ± 0.25<br>σ2 = 1.49 ± 0.18 |
| SN-123 | 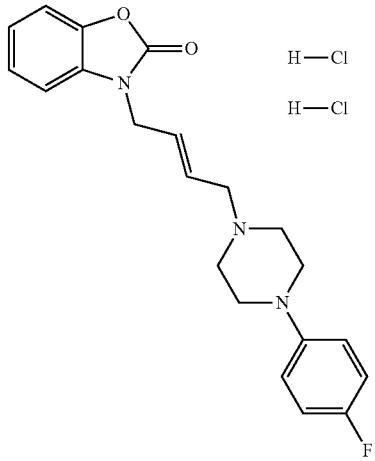 | |
| SN-124 | 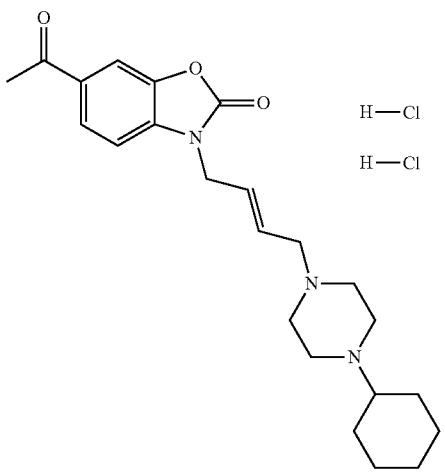 | |

| Compd. | Structure | Ki (nM) |
|---|---|---|
| SN-125 | 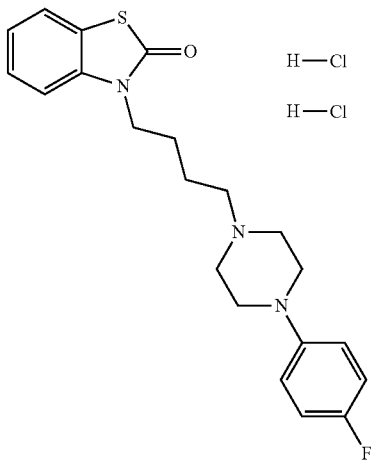 H—Cl<br>H—Cl | |
| SN-126 | 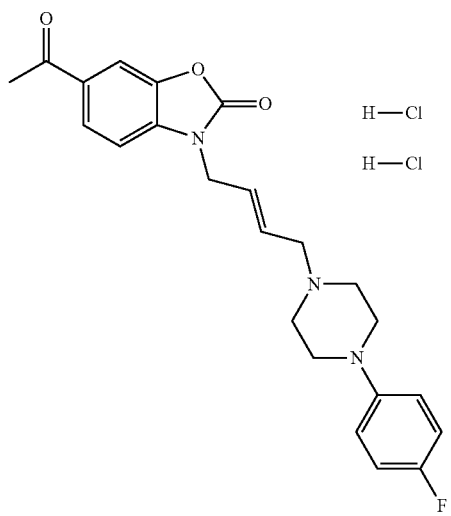 H—Cl<br>H—Cl | |
| SN-127 | 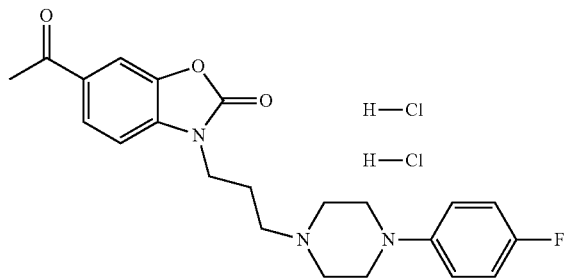 H—Cl<br>H—Cl | |

| Compd. | Structure | Ki (nM) |
|---|---|---|
| SN-136 | 6-acetyl-3-[5-[4-(4-fluorophenyl)piperazin-1-yl]pentyl]-1,3-benzoxazol-2(3H)-one · 2 HCl | |
| SN-137 | 6-acetyl-3-[4-[4-(4-fluorophenyl)piperazin-1-yl]butyl]-1,3-benzothiazol-2(3H)-one · 2 HCl | |
| SN-138 | 6-acetyl-3-[4-[4-(2-fluorophenyl)piperazin-1-yl]butyl]-1,3-benzothiazol-2(3H)-one | |
| SN-139 | 6-acetyl-3-[6-[4-(4-fluorophenyl)piperazin-1-yl]hexyl]-1,3-benzoxazol-2(3H)-one · 2 HCl | |

-continued
| Compd. | Structure | Ki (nM) |
|---|---|---|
| SN-140 | 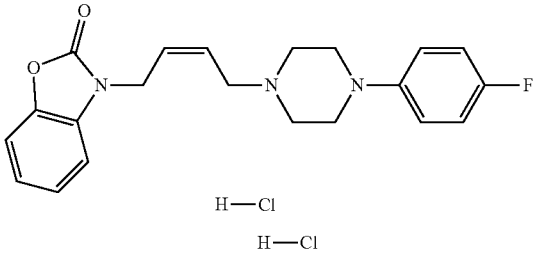 | |
| SN-147 | 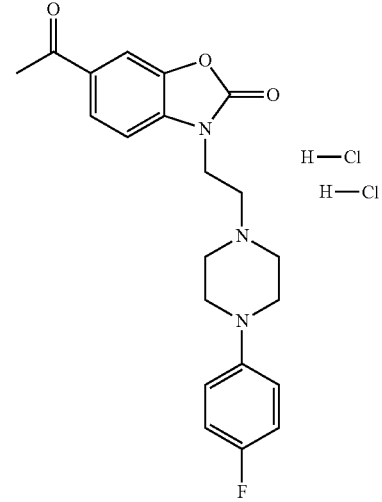 | |
| SN-148 | 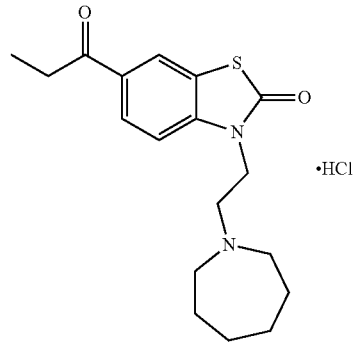 [SMILES: CCC(=O)c1ccc2c(c1)sc(=O)n2CCN1CCCCCC1 ; Cl] | |
| SN-150 | 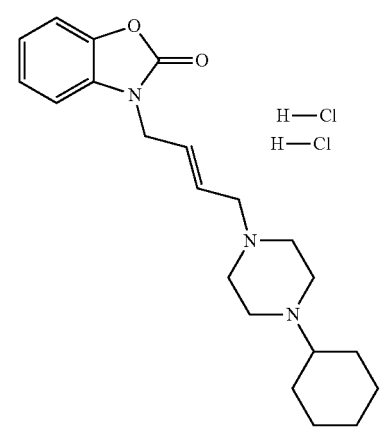 | |

-continued

| Compd. | Structure | Ki (nM) |
|---|---|---|
| SN-158 | 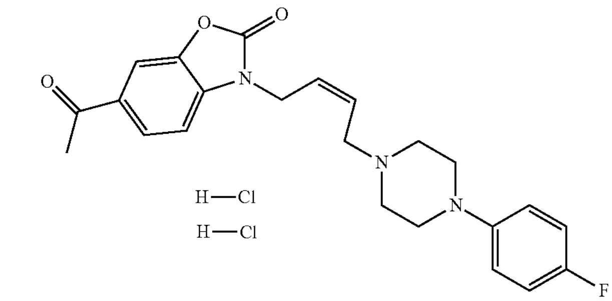 | |
| SN-167 | 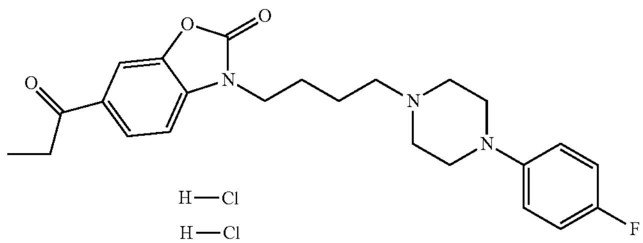 | |
| SN-168 | 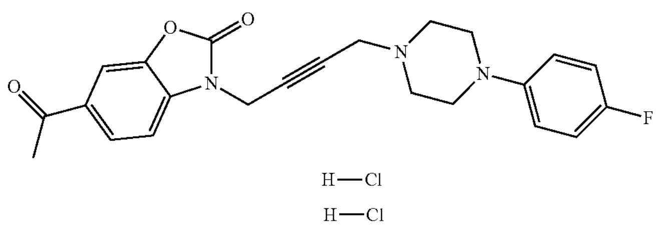 | |
| SN-169 | 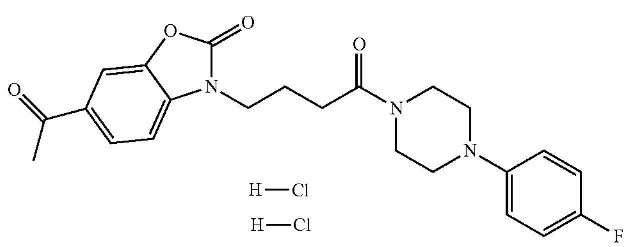 | |
| SN-170 | 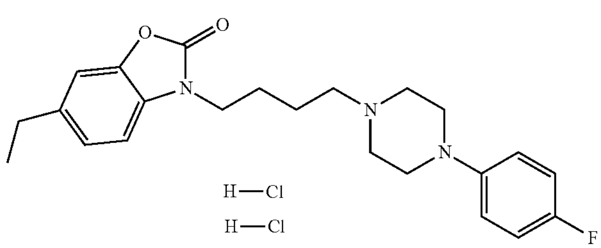 | |
| SN-196 | 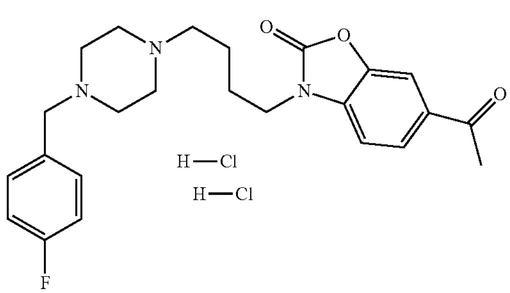 | |

-continued
| Compd. | Structure | Ki (nM) |
|---|---|---|
| SN-197 | 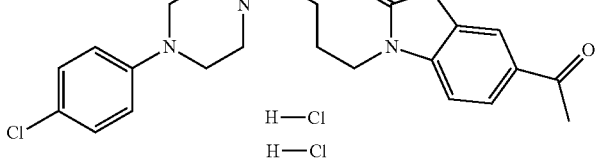 | |
| SN-198 | 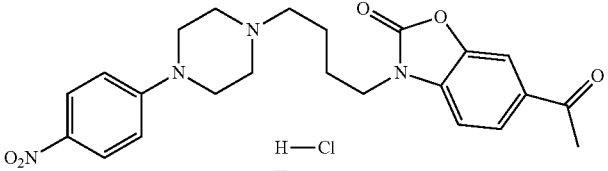 | |
| SN-199 | 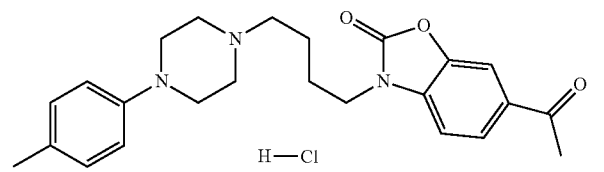 | |
| SN-203 | 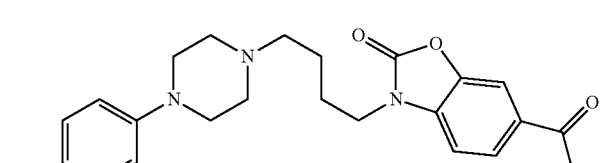 | |
| SN-204 | 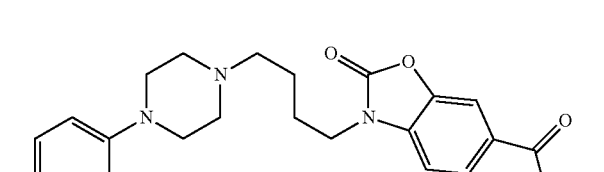 | |
| SN-205 | 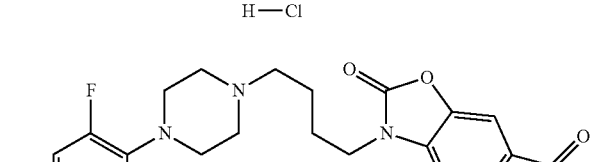 | |
| SN-212 | 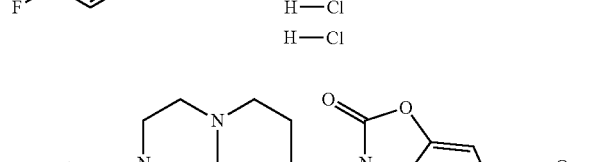 | |

-continued
| Compd. | Structure | Ki (nM) |
|---|---|---|
| SN-213 | 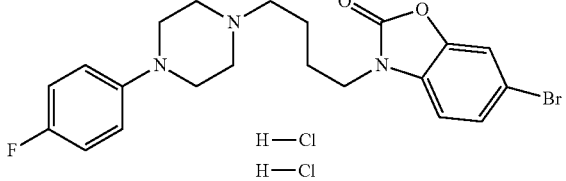 | |
| SN-214 | 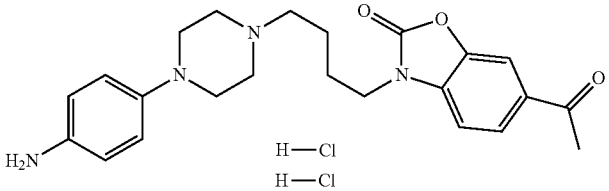 | |
| SN-230 | 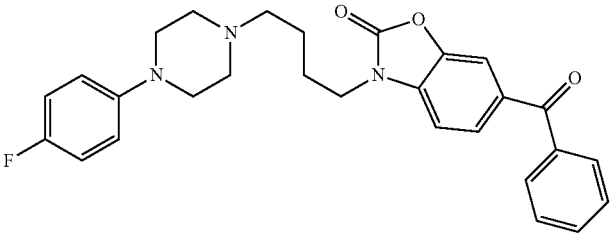 [SMILES: O=C(c1ccccc1)c1ccc2c(c1)oc(=O)n2CCCCN1CCN(c2ccc(F)cc2)CC1] | |
| SN-231 | 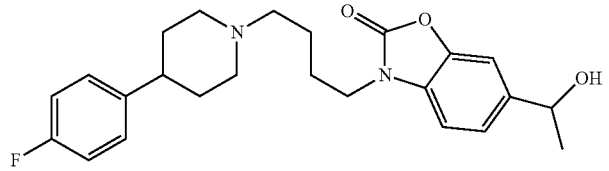 [SMILES: CC(O)c1ccc2c(c1)oc(=O)n2CCCCN1CCC(c2ccc(F)cc2)CC1] | |
| SN-232 | 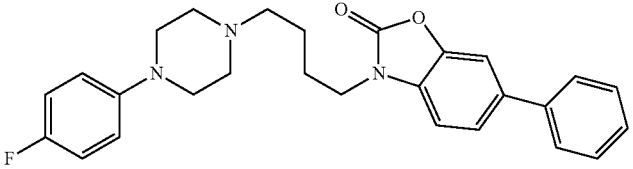 [SMILES: O=c1oc2cc(-c3ccccc3)ccc2n1CCCCN1CCN(c2ccc(F)cc2)CC1] | |

| CMPD | STRUCTURE | Ki (nM) $\sigma_1$ | Ki (nM) $\sigma_2$ |
|---|---|---|---|
| CM 121 | 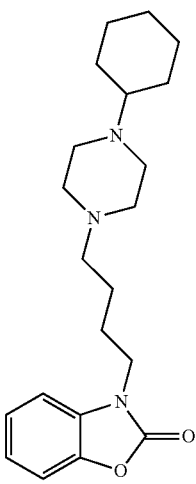 [SMILES: O=c1oc2ccccc2n1CCCCN1CCN(C2CCCCC2)CC1] | 11.26 ± 1.25 | 1.83 ± 0.17 |
| CM 124 | 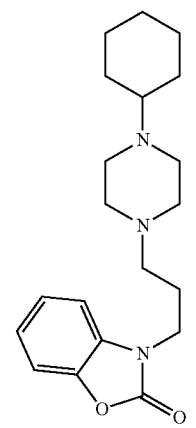 [SMILES: O=c1oc2ccccc2n1CCCN1CCN(C2CCCCC2)CC1] | 5.22 ± 1.11 | 8.74 ± 2.30 |
| CM 126 | 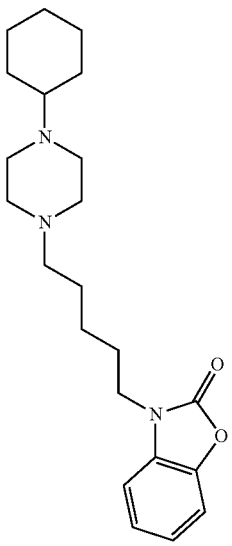 [SMILES: O=c1oc2ccccc2n1CCCCCN1CCN(C2CCCCC2)CC1] | 10.55 ± 2.52 | 5.89 ± 1.31 |

-continued
| CMPD | STRUCTURE | Ki (nM) $\sigma_1$ | Ki (nM) $\sigma_2$ |
|---|---|---|---|
| CM 129 | 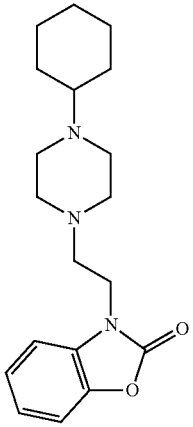 [SMILES: O=c1oc2ccccc2n1CCN1CCN(C2CCCCC2)CC1] | 6.90 ± 0.37 | 5.43 ± 0.78 |
| CM 135 | 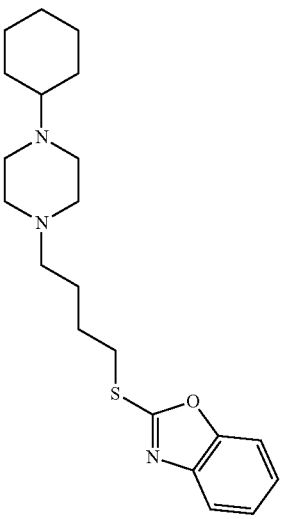 [SMILES: c1ccc2oc(SCCCCN3CCN(C4CCCCC4)CC3)nc2c1] | 3.37 ± 0.28 | 3.77 ± 0.35 |
| CM 138 | 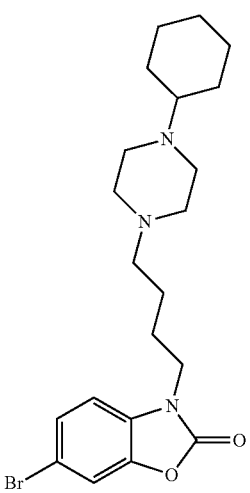 [SMILES: O=c1oc2cc(Br)ccc2n1CCCCN1CCN(C2CCCCC2)CC1] | 7.87 ± 0.19 | 4.47 ± 0.42 |

-continued
| CMPD | STRUCTURE | Ki (nM) σ₁ | Ki (nM) σ₂ |
|---|---|---|---|
| CM 142 | 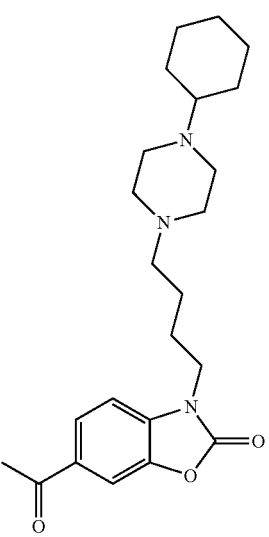 [SMILES: CC(=O)c1ccc2c(c1)oc(=O)n2CCCCN1CCN(C2CCCCC2)CC1] | 46.4 ± 8.06 | 7.04 ± 0.79 |
| CM 145 | 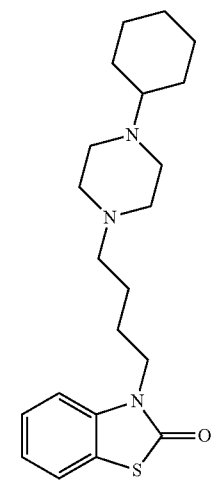 | 4.17 ± 0.62 | 0.39 ± 0.06 |
| CM 146 | 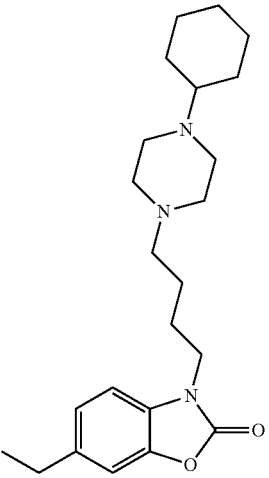 [SMILES: CCc1ccc2c(c1)oc(=O)n2CCCCN1CCN(C2CCCCC2)CC1] | 2.18 ± 0.14 | 2.56 ± 1.22 |

-continued
| CMPD | STRUCTURE | Ki (nM) $\sigma_1$ | Ki (nM) $\sigma_2$ |
|---|---|---|---|
| CM 152 | 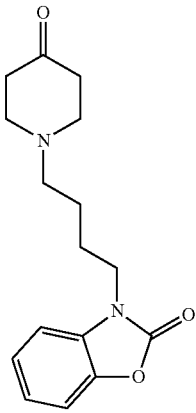 [SMILES: O=C1CCN(CCCCn2c(=O)oc3ccccc32)CC1] | 19.3 ± 0.90 | 78.5 ± 39.6 |
| CM 156 | 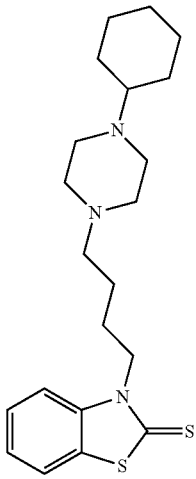 [SMILES: S=c1sc2ccccc2n1CCCCN1CCN(C2CCCCC2)CC1] | 1.28 ± 0.38 | 0.55 ± 0.08 |
| CM 159 | 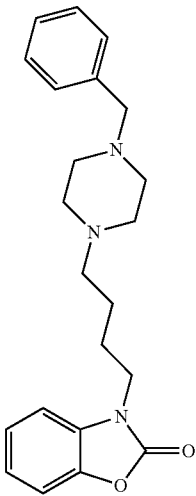 [SMILES: O=c1oc2ccccc2n1CCCCN1CCN(Cc2ccccc2)CC1] | 4.44 ± 0.88 | 46.41 ± 12.61 |

-continued
| CMPD | STRUCTURE | Ki (nM) $\sigma_1$ | Ki (nM) $\sigma_2$ |
|---|---|---|---|
| CM 160 | 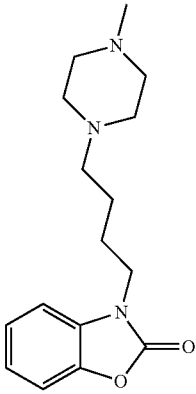 [SMILES: CN1CCN(CCCCn2c(=O)oc3ccccc32)CC1] | 91.69 ± 11.52 | 2382.33 ± 142.94 |
| CM 162 | 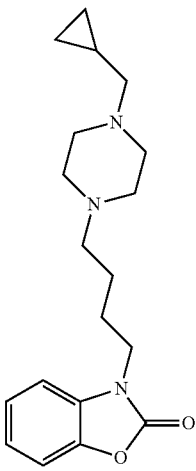 [SMILES: O=c1oc2ccccc2n1CCCCN1CCN(CC2CC2)CC1] | 10.83 ± 1.00 | 46.75 ± 10.18 |
| CM 165 | 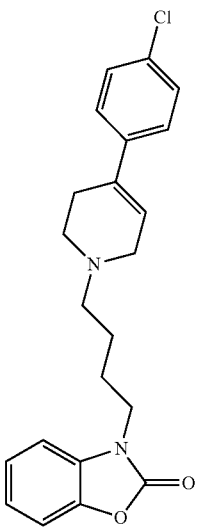 [SMILES: O=c1oc2ccccc2n1CCCCN1CC=C(c2ccc(Cl)cc2)CC1] | 2.40 ± 0.38 | 14.44 ± 3.09 |

-continued
| CMPD | STRUCTURE | Ki (nM) σ₁ | Ki (nM) σ₂ |
|---|---|---|---|
| CM 166 | 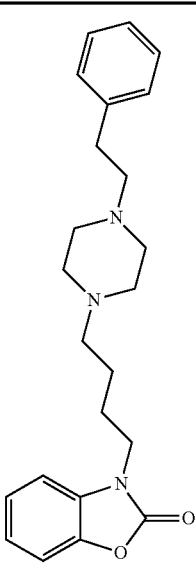 | 3.15 ± 0.37 | 92.71 ± 14.14 |
| CM 167 | 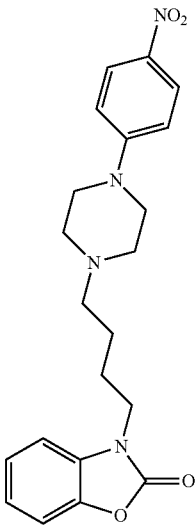 [SMILES: O=c1oc2ccccc2n1CCCCN1CCN(c2ccc([N+](=O)[O-])cc2)CC1] | 259.07 ± 33.45 | 226.00 ± 17.50 |
| CM 168 | 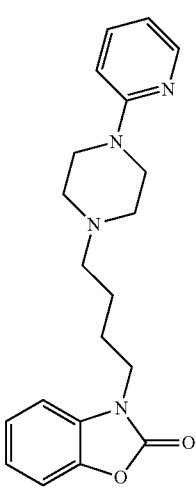 [SMILES: O=c1oc2ccccc2n1CCCCN1CCN(c2ccccn2)CC1] | 311.93 ± 33.22 | 128.10 ± 16.26 |

-continued
| CMPD | STRUCTURE | Ki (nM) $\sigma_1$ | Ki (nM) $\sigma_2$ |
|---|---|---|---|
| CM 169 | 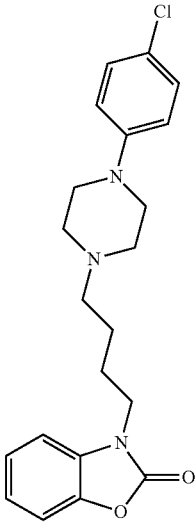 [SMILES: O=c1oc2ccccc2n1CCCCN1CCN(c2ccc(Cl)cc2)CC1] | 25.44 ± 4.72 | 241.5 ± 28.98 |
| CM 170 | 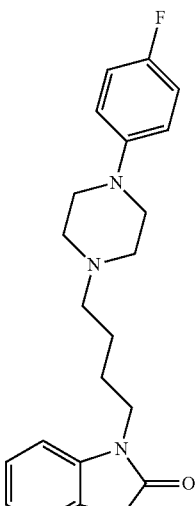 | 7.59 ± 0.08 | 0.70 ± 0.11 |
| CM 171 | 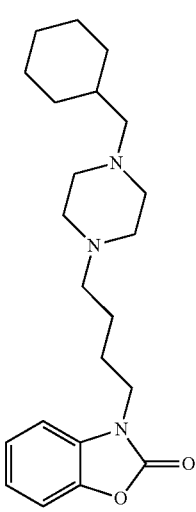 [SMILES: O=c1oc2ccccc2n1CCCCN1CCN(CC2CCCCC2)CC1] | 0.94 ± 0.13 | 13.94 ± 2.86 |

-continued

| CMPD | STRUCTURE | Ki (nM) $\sigma_1$ | Ki (nM) $\sigma_2$ |
|---|---|---|---|
| CM 172 | 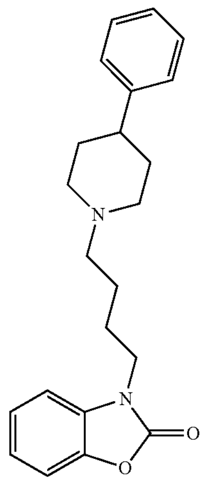 [SMILES: O=c1oc2ccccc2n1CCCCN1CCC(c2ccccc2)CC1] | 0.58 ± 0.22 | 17.22 ± 1.04 |
| CM 174 | 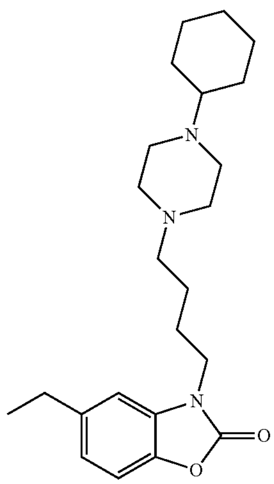 [SMILES: CCc1ccc2oc(=O)n(CCCCN3CCN(C4CCCCC4)CC3)c2c1] | 4.04 ± 0.35 | 58.24 ± 11.48 |
| CM 175 | 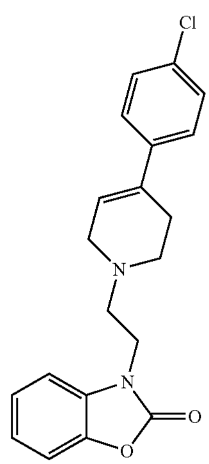 [SMILES: O=c1oc2ccccc2n1CCN1CC=C(c2ccc(Cl)cc2)CC1] | 21.37 ± 3.68 | 616.33 ± 77.47 |

-continued
| CMPD | STRUCTURE | Ki (nM) σ₁ | Ki (nM) σ₂ |
|---|---|---|---|
| CM 176 | 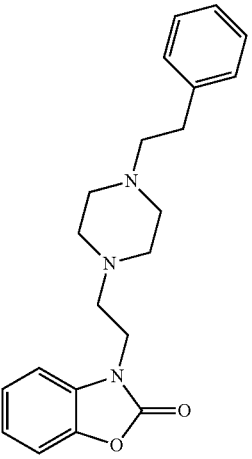 [SMILES: O=c1oc2ccccc2n1CCN1CCN(CCc2ccccc2)CC1] | 1.43 ± 0.26 | 21.73 ± 2.79 |
| CM 178 | 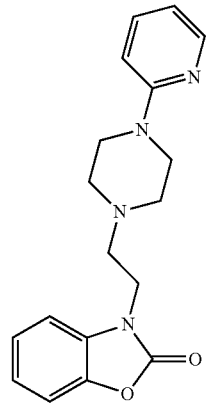 [SMILES: O=c1oc2ccccc2n1CCN1CCN(c2ccccn2)CC1] | >10,000 | >10,000 |
| CM 179 | 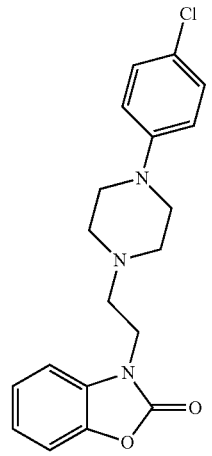 [SMILES: O=c1oc2ccccc2n1CCN1CCN(c2ccc(Cl)cc2)CC1] | 1426.33 ± 185.09 | 2260 ± 96.08 |

-continued
| CMPD | STRUCTURE | Ki (nM) σ₁ | Ki (nM) σ₂ |
|------|-----------|------------|------------|
| CM 181 | 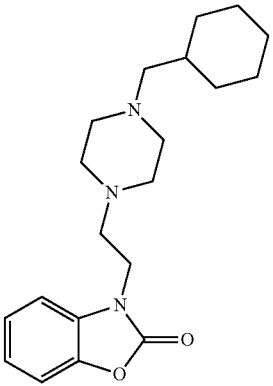 [SMILES: O=c1oc2ccccc2n1CCN1CCN(CC2CCCCC2)CC1] | 2.36 ± 0.38 | 8.83 ± 1.17 |
| CM 182 | 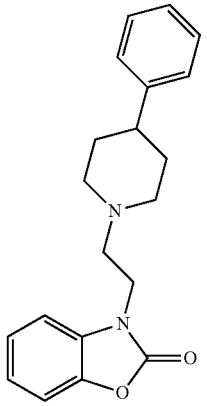 [SMILES: O=c1oc2ccccc2n1CCN1CCC(c2ccccc2)CC1] | 14.08 ± 2.84 | 777.26 ± 72.47 |
| CM 184 | 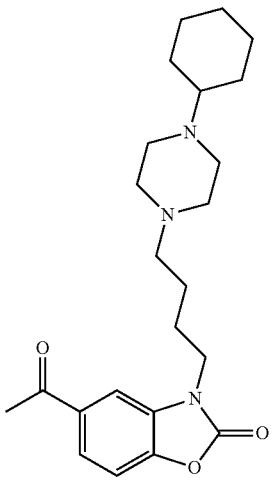 [SMILES: CC(=O)c1ccc2oc(=O)n(CCCCN3CCN(C4CCCCC4)CC3)c2c1] | 40.82 ± 6.21 | 10.41 ± 1.54 |

-continued
| CMPD | STRUCTURE | Ki (nM) σ₁ | Ki (nM) σ₂ |
|---|---|---|---|
| CM 188 | 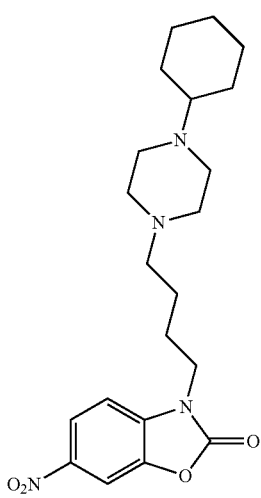 [SMILES: O=c1oc2cc([N+](=O)[O-])ccc2n1CCCCN1CCN(C2CCCCC2)CC1] | 11.11 ± 1.61 | 2.46 ± 0.18 |
| CM 191 | 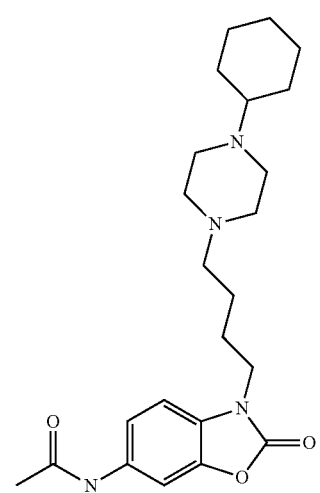 | 213.87 ± 55.33 | 77.37 ± 14.22 |
| CM 295 | 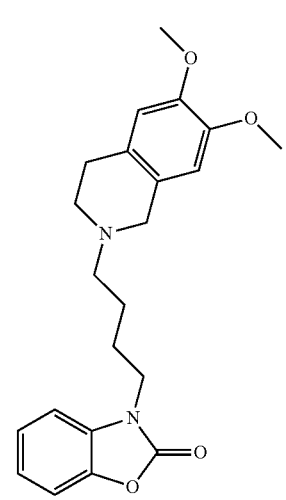 [SMILES: COc1cc2c(cc1OC)CN(CCCCn1c(=O)oc3ccccc31)CC2] | 74.31 ± 3.77 | 1.52 ± 0.64 |

-continued
| CMPD | STRUCTURE | Ki (nM) $\sigma_1$ | Ki (nM) $\sigma_2$ |
| --- | --- | --- | --- |
| CM 307 | 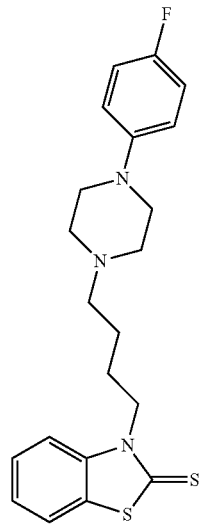 [SMILES: Fc1ccc(N2CCN(CCCCn3c(=S)sc4ccccc43)CC2)cc1] | 6.27 ± 0.78 | 6.61 ± 1.42 |
| CM 308 | 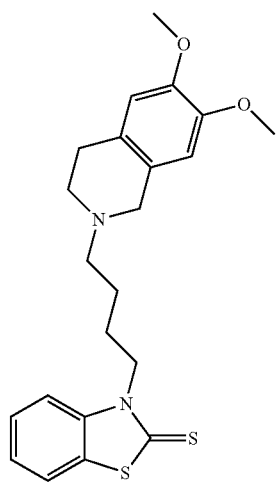 [SMILES: COc1cc2c(cc1OC)CN(CCCCn1c(=S)sc3ccccc31)CC2] | 9.11 ± 1.31 | 0.56 ± 0.12 |

-continued
| CMPD | STRUCTURE | Ki (nM) σ₁ | Ki (nM) σ₂ |
|---|---|---|---|
| CM 322 | 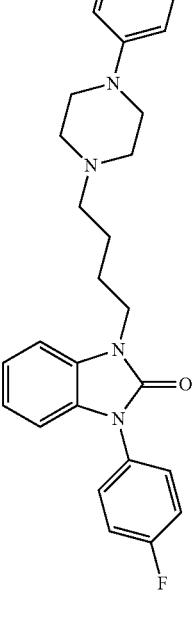 | 118.46 ± 48.37 | 1.67 ± 0.16 |
| CM 325 | 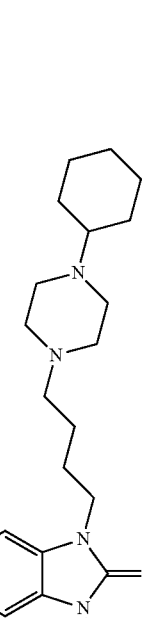 | 5.04 ± 0.66 | 2.12 ± 0.75 |

| CMPD | STRUCTURE | Ki (nM) σ₁ | Ki (nM) σ₂ |
|---|---|---|---|
| CM 328 | 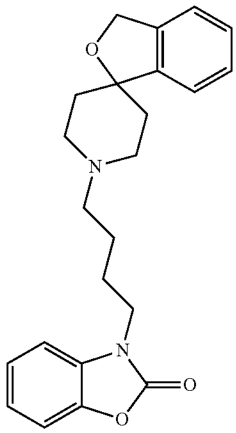 [SMILES: O=c1oc2ccccc2n1CCCCN1CCC2(CC1)OCc1ccccc12] | | |
| CM 329 | 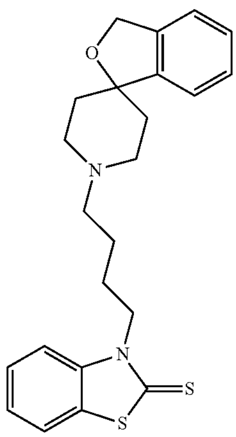 [SMILES: S=c1sc2ccccc2n1CCCCN1CCC2(CC1)OCc1ccccc12] | | |
| CM 330 | 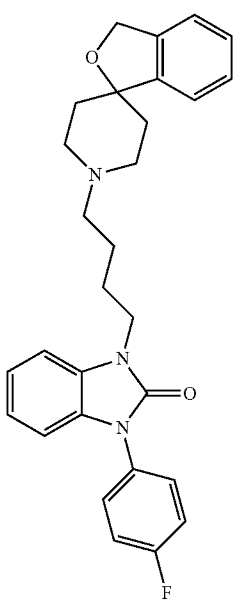 [SMILES: O=c1n(CCCCN2CCC3(CC2)OCc2ccccc23)c2ccccc2n1-c1ccc(F)cc1] | | |

-continued
| CMPD | STRUCTURE | Ki (nM) σ₁ | Ki (nM) σ₂ |
|---|---|---|---|
| CM 338 | 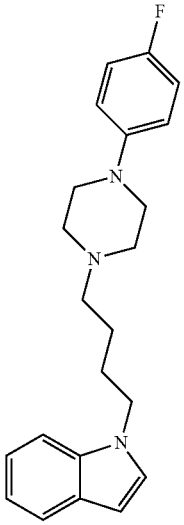 [SMILES: Fc1ccc(N2CCN(CCCCn3ccc4ccccc43)CC2)cc1] | 169.8 ± 5.68 | 1.09 ± 0.03 |
| CM 339 | 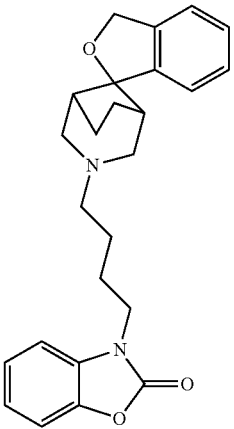 [SMILES: O=c1oc2ccccc2n1CCCCN1CC2CCC(C1)C21OCc2ccccc21] | | |
| CM 341 | 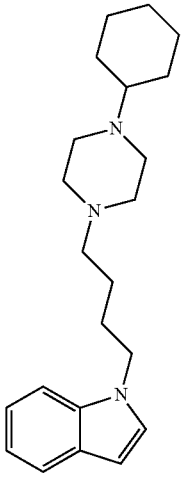 [SMILES: c1ccc2c(c1)ccn2CCCCN1CCN(C2CCCCC2)CC1] | 3.28 ± 0.32 | 1.90 ± 0.16 |

-continued
| CMPD | STRUCTURE | Ki (nM) $\sigma_1$ | Ki (nM) $\sigma_2$ |
|---|---|---|---|
| CM 343 | 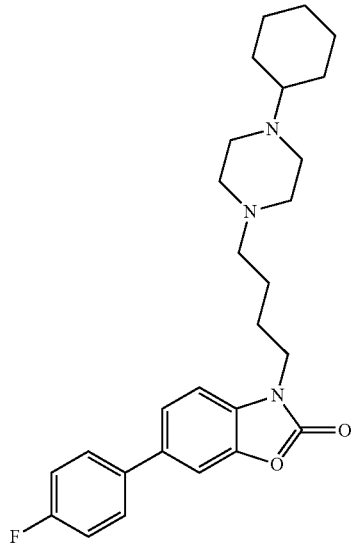 | 17.6 ± 0.82 | 38.13 ± 1.42 |
| CM 347 | 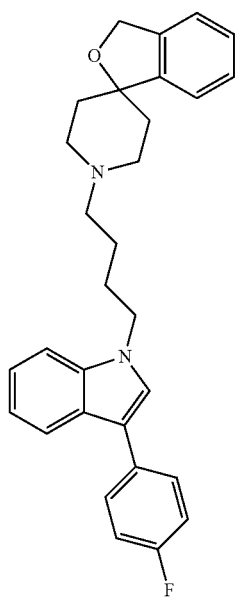 [SMILES: Fc1ccc(-c2cn(CCCCN3CCC4(CC3)OCc3ccccc34)c3ccccc23)cc1] | | |

-continued
| CMPD | STRUCTURE | Ki (nM) σ₁ | Ki (nM) σ₂ |
| --- | --- | --- | --- |
| CM 349 | 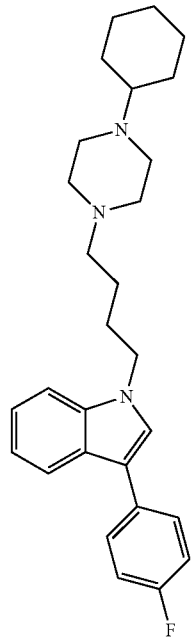 [SMILES: Fc1ccc(-c2cn(CCCCN3CCN(C4CCCCC4)CC3)c3ccccc23)cc1] | 90.87 ± 12.30 | 22.55 ± 1.13 |
| CM 350 | 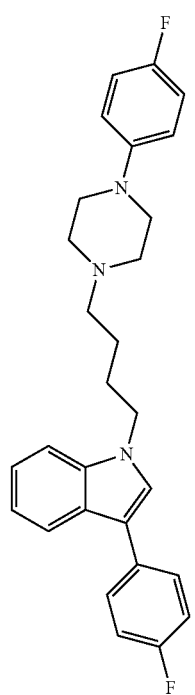 [SMILES: Fc1ccc(-c2cn(CCCCN3CCN(c4ccc(F)cc4)CC3)c3ccccc23)cc1] | 1202 ± 73.89 | 83.33 ± 3.96 |

| CMPD | STRUCTURE | Ki (nM) $\sigma_1$ | Ki (nM) $\sigma_2$ |
|---|---|---|---|
| CM 353 | 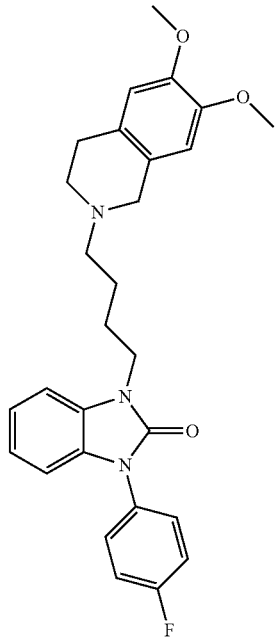 [SMILES: COc1cc2c(cc1OC)CN(CCCCn1c(=O)n(-c3ccc(F)cc3)c3ccccc31)CC2] | | |
| CM 355 | 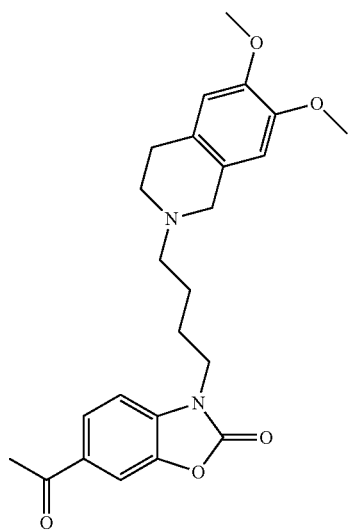 [SMILES: COc1cc2c(cc1OC)CN(CCCCn1c(=O)oc3cc(C(C)=O)ccc31)CC2] | | |

-continued

| CMPD | STRUCTURE | Ki (nM) $\sigma_1$ | Ki (nM) $\sigma_2$ |
| --- | --- | --- | --- |
| CM 356 | 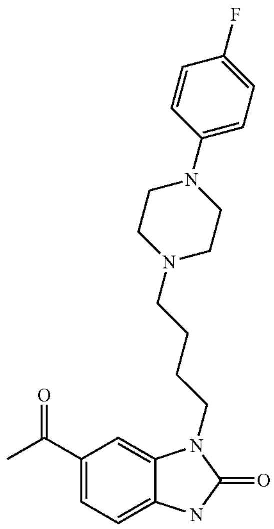 [SMILES: CC(=O)c1ccc2[nH]c(=O)n(CCCCN3CCN(c4ccc(F)cc4)CC3)c2c1] | 27.82 ± 4.14 | 1.21 ± 0.20 |
| CM 357 | 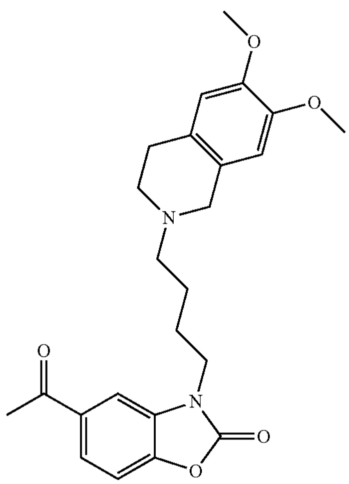 [SMILES: COc1cc2c(cc1OC)CN(CCCCn1c(=O)oc3ccc(C(C)=O)cc31)CC2] | | |
| CM 360 | 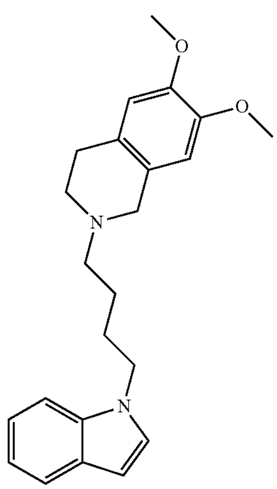 [SMILES: COc1cc2c(cc1OC)CN(CCCCn1ccc3ccccc31)CC2] | 73.25 ± 5.58 | 0.21 ± 0.020 |

-continued

| CMPD | STRUCTURE | Ki (nM) σ$_1$ | Ki (nM) σ$_2$ |
|---|---|---|---|
| CM 361 | 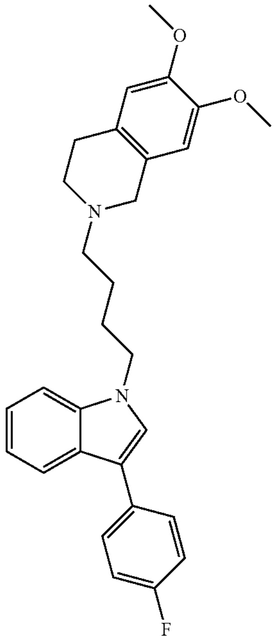 [SMILES: COc1cc2c(cc1OC)CN(CCCCn1cc(-c3ccc(F)cc3)c3ccccc31)CC2] | 4713 ± 449.50 | 4.37 ± 0.33 |
| CM 362 | 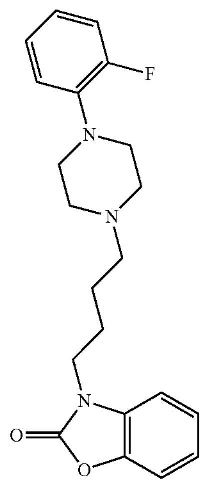 [SMILES: O=c1oc2ccccc2n1CCCCN1CCN(c2ccccc2F)CC1] | 17.64 ± 3.34 | 2.79 ± 0.49 |
| CM 365 | 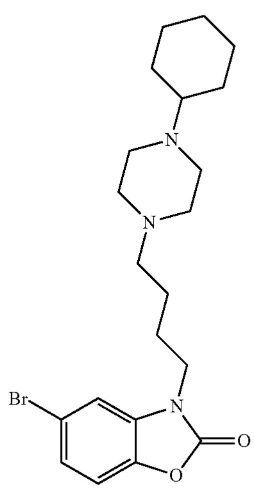 [SMILES: O=c1oc2ccc(Br)cc2n1CCCCN1CCN(C2CCCCC2)CC1] | 5.94 ± 0.35 | 0.055 ± 0.0063 |

-continued
| CMPD | STRUCTURE | Ki (nM) σ₁ | Ki (nM) σ₂ |
|---|---|---|---|
| CM 366 | 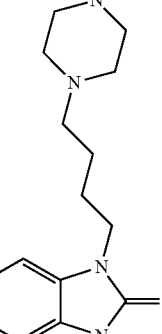 | 22.55 ± 1.14 | 0.0061 ± 0.00096 |
| CM 372 | 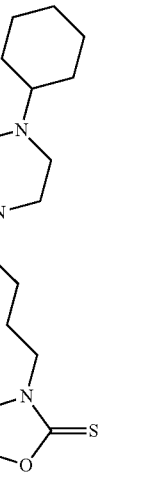 | 4.90 ± 1.70 | 0.77 ± 0.06 |
| CM 373 | 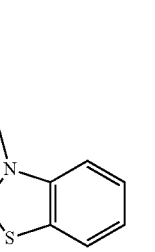 | | |
| CM 393 | 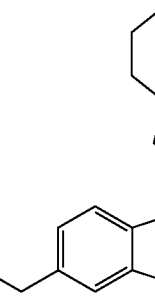 | | |

| CMPD | STRUCTURE | Ki (nM) $\sigma_1$ | Ki (nM) $\sigma_2$ |
|---|---|---|---|
| CM 394 | 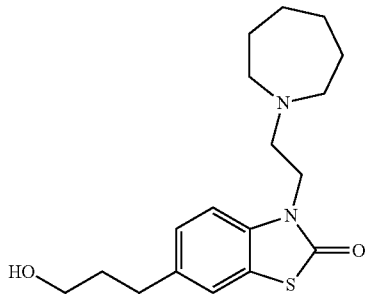 [SMILES: O=c1sc2cc(CCCO)ccc2n1CCN1CCCCCC1] | | |
| CM 396 | 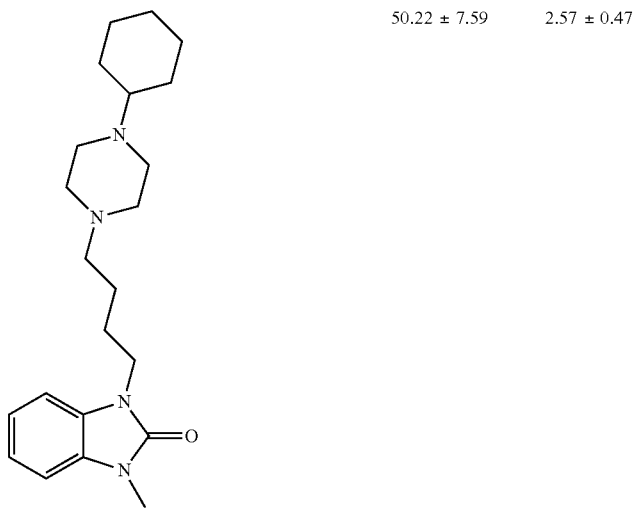 | 50.22 ± 7.59 | 2.57 ± 0.47 |
| CM 397 | 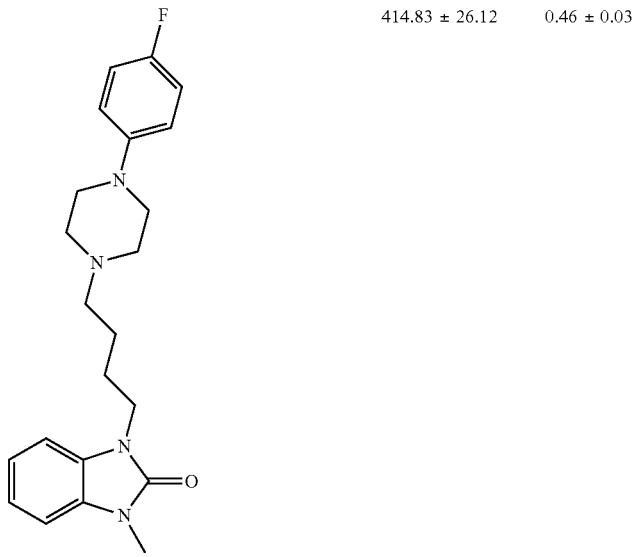 | 414.83 ± 26.12 | 0.46 ± 0.03 |

-continued

| CMPD | STRUCTURE | Ki (nM) $\sigma_1$ | Ki (nM) $\sigma_2$ |
|---|---|---|---|
| CM 398 | 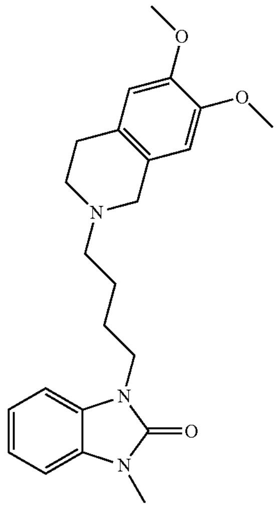 [SMILES: COc1cc2c(cc1OC)CN(CCCCn1c(=O)n(C)c3ccccc31)CC2] | | |
| CM 401 | 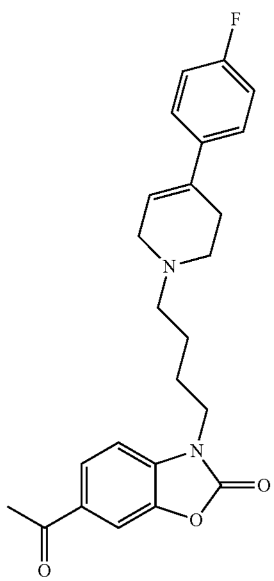 [SMILES: CC(=O)c1ccc2c(c1)oc(=O)n2CCCCN1CC=C(c2ccc(F)cc2)CC1] | 2.89 ± 0.23 | 0.66 ± 0.08 |
| CM 406 | 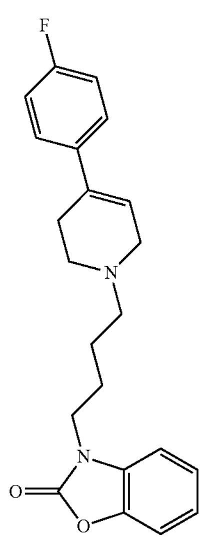 [SMILES: O=c1oc2ccccc2n1CCCCN1CC=C(c2ccc(F)cc2)CC1] | | |

-continued
| CMPD | STRUCTURE | Ki (nM) σ₁ | Ki (nM) σ₂ |
|---|---|---|---|
| CM 407 | 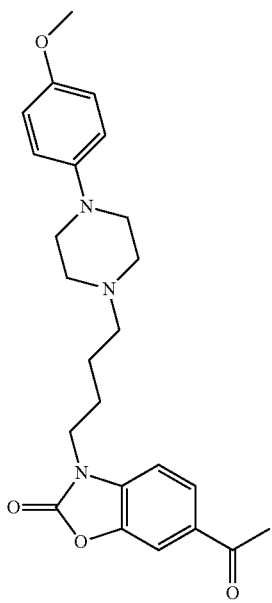 [SMILES: COc1ccc(N2CCN(CCCCn3c(=O)oc4cc(C(C)=O)ccc43)CC2)cc1] | | |
| CM 408 | 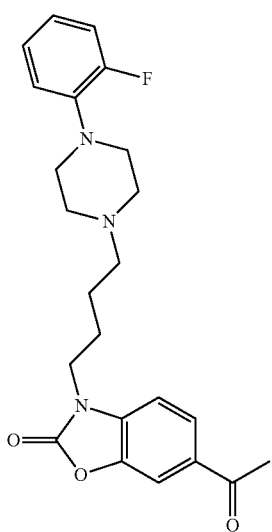 [SMILES: CC(=O)c1ccc2c(c1)oc(=O)n2CCCCN1CCN(c2ccccc2F)CC1] | | |
| CM 418 | 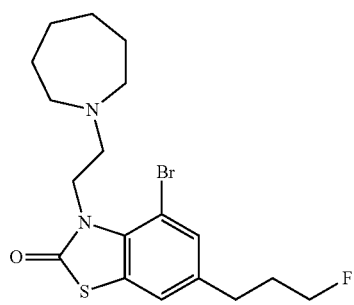 [SMILES: O=c1sc2cc(CCCF)cc(Br)c2n1CCN1CCCCCC1] | | |

-continued
| CMPD | STRUCTURE | Ki (nM) σ₁ | Ki (nM) σ₂ |
|---|---|---|---|
| CM 422 | 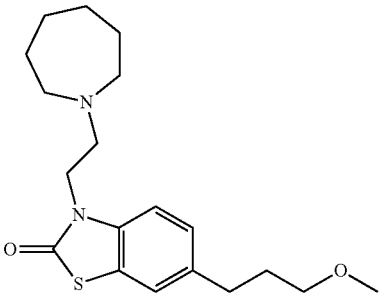 [SMILES: COCCCc1ccc2c(c1)sc(=O)n2CCN1CCCCCC1] | | |
| CM 423 | 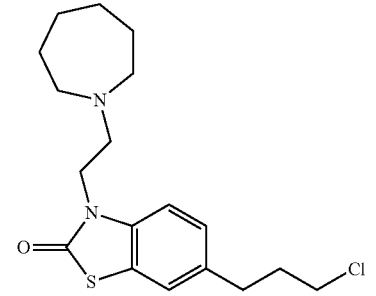 [SMILES: O=c1sc2cc(CCCCl)ccc2n1CCN1CCCCCC1] | | |
| CM 433 | 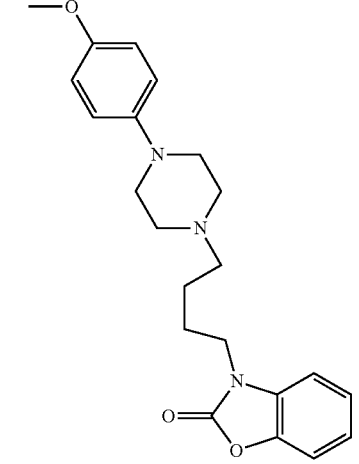 [SMILES: COc1ccc(N2CCN(CCCCn3c(=O)oc4ccccc43)CC2)cc1] | | |
| CM 435 | 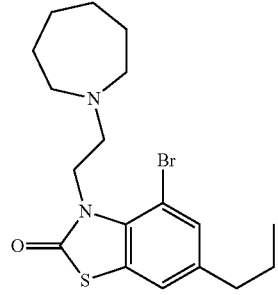 [SMILES: CCCc1cc(Br)c2c(c1)sc(=O)n2CCN1CCCCCC1] | | |

-continued
| CMPD | STRUCTURE | Ki (nM) $\sigma_1$ | Ki (nM) $\sigma_2$ |
|---|---|---|---|
| CM 436 | 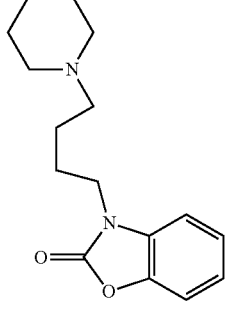 | | |
| CM 442 | 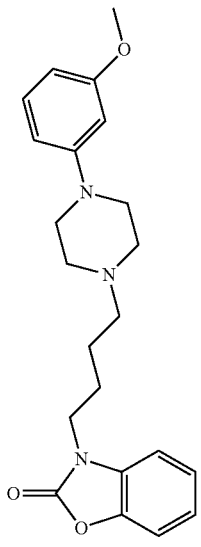 [SMILES: COc1cccc(N2CCN(CCCCn3c(=O)oc4ccccc43)CC2)c1] | | |
| CM 444 | 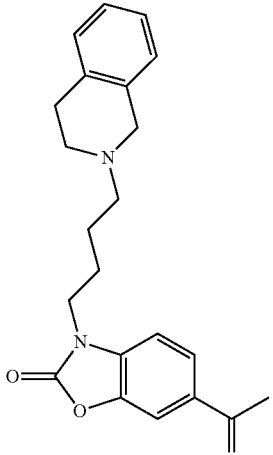 | | |

| CMPD | STRUCTURE | Ki (nM) σ₁ | Ki (nM) σ₂ |
|---|---|---|---|
| CM 449 | 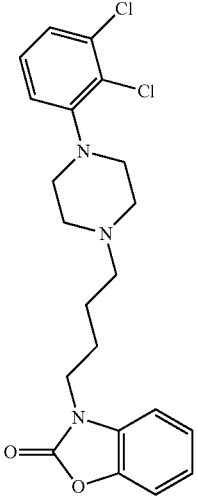 [SMILES: O=c1oc2ccccc2n1CCCCN1CCN(c2cccc(Cl)c2Cl)CC1] | | |
| CM 450 | 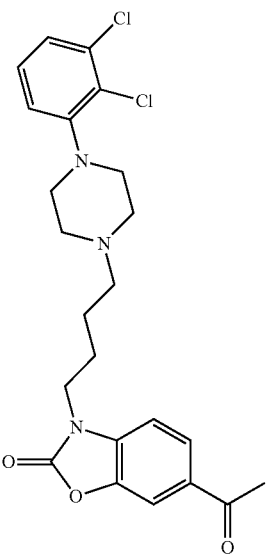 [SMILES: CC(=O)c1ccc2c(c1)oc(=O)n2CCCCN1CCN(c2cccc(Cl)c2Cl)CC1] | | |
| CM 454 | 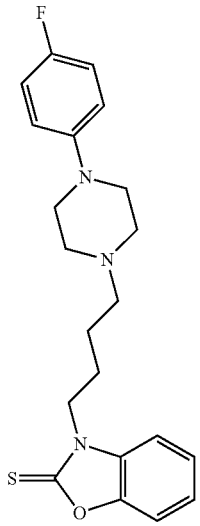 [SMILES: Fc1ccc(N2CCN(CCCCn3c(=S)oc4ccccc43)CC2)cc1] | | |

| CMPD | STRUCTURE | Ki (nM) $\sigma_1$ | Ki (nM) $\sigma_2$ |
|---|---|---|---|
| CM 458 | 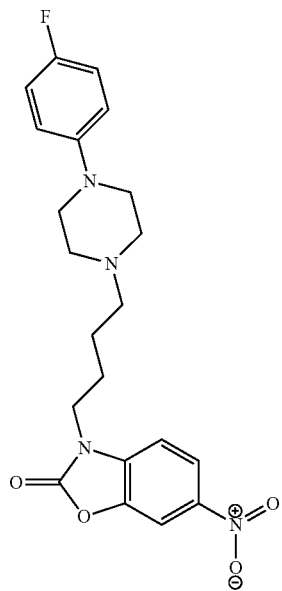 [SMILES: O=c1oc2cc([N+](=O)[O-])ccc2n1CCCCN1CCN(c2ccc(F)cc2)CC1] | | |
| CM 459 | 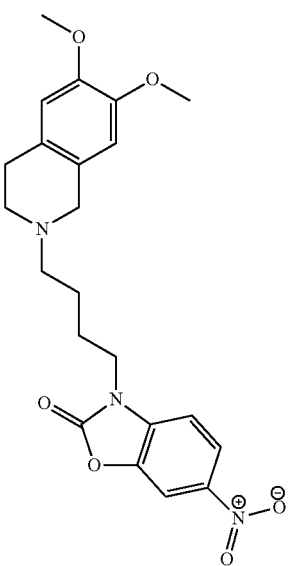 [SMILES: COc1cc2c(cc1OC)CN(CCCCn1c(=O)oc3cc([N+](=O)[O-])ccc31)CC2] | | |

| CMPD | STRUCTURE | Ki (nM) σ₁ | Ki (nM) σ₂ |
|---|---|---|---|
| CM 461 | 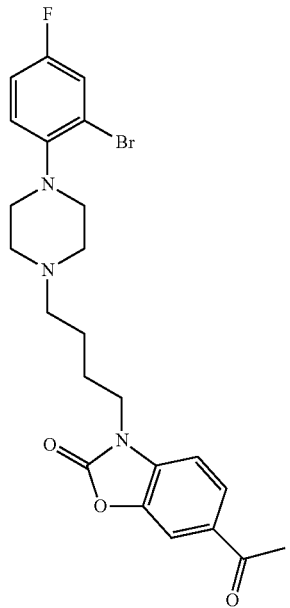 [SMILES: CC(=O)c1ccc2c(c1)oc(=O)n2CCCCN1CCN(c2ccc(F)cc2Br)CC1] | | |
| CM 464 | 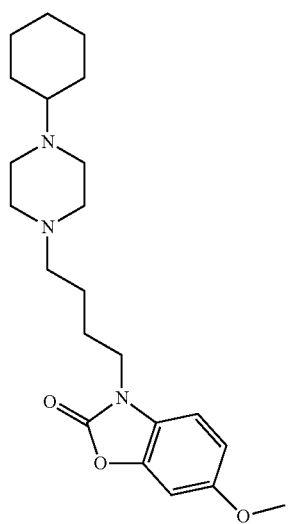 [SMILES: COc1ccc2c(c1)oc(=O)n2CCCCN1CCN(C2CCCCC2)CC1] | | |

-continued
| CMPD | STRUCTURE | Ki (nM) $\sigma_1$ | Ki (nM) $\sigma_2$ |
|---|---|---|---|
| CM 465 | 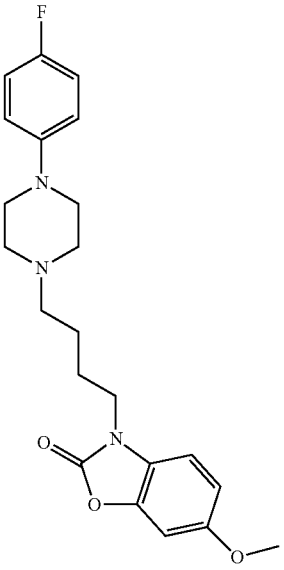 [SMILES: COc1ccc2c(c1)oc(=O)n2CCCCN1CCN(c2ccc(F)cc2)CC1] | | |
| CM 466 | 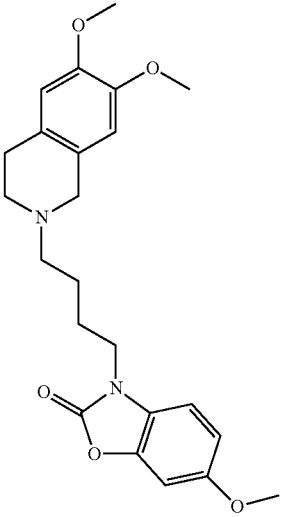 [SMILES: COc1ccc2c(c1)oc(=O)n2CCCCN1CCc2cc(OC)c(OC)cc2C1] | | |
| CM 471 | 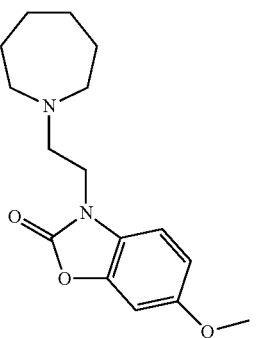 [SMILES: COc1ccc2c(c1)oc(=O)n2CCN1CCCCCC1] | | |

| CMPD | STRUCTURE | Ki (nM) σ₁ | Ki (nM) σ₂ |
|---|---|---|---|
| CM 483 | 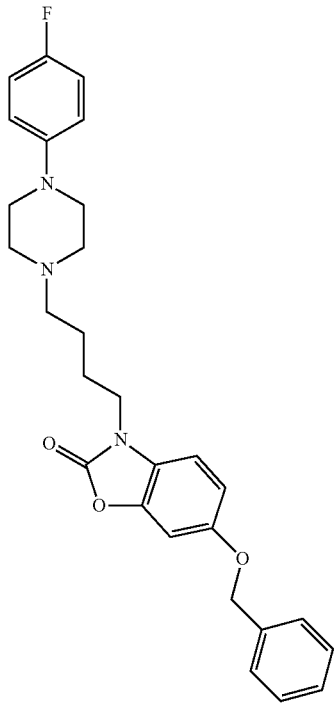 [SMILES: O=c1oc2cc(OCc3ccccc3)ccc2n1CCCCN1CCN(c2ccc(F)cc2)CC1] | | |
| CM 484 | 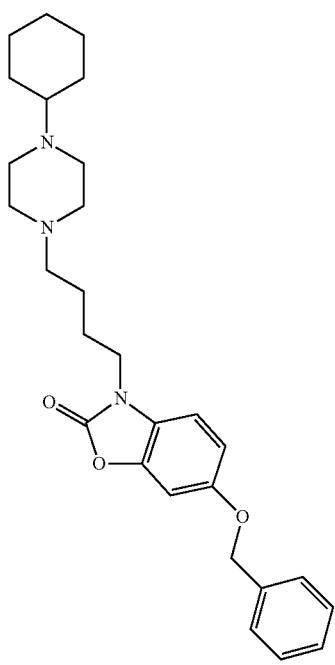 [SMILES: O=c1oc2cc(OCc3ccccc3)ccc2n1CCCCN1CCN(C2CCCCC2)CC1] | | |

-continued
| CMPD | STRUCTURE | Ki (nM) σ₁ | Ki (nM) σ₂ |
|---|---|---|---|
| CM 485 | 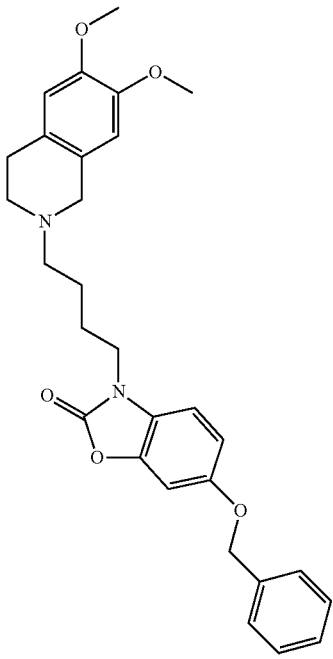 [SMILES: COc1cc2c(cc1OC)CN(CCCCn1c(=O)oc3cc(OCc4ccccc4)ccc31)CC2] | | |
| CM 490 | 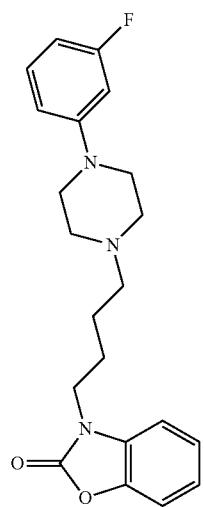 [SMILES: O=c1oc2ccccc2n1CCCCN1CCN(c2cccc(F)c2)CC1] | | |

-continued
| CMPD | STRUCTURE | Ki (nM) σ₁ | Ki (nM) σ₂ |
|---|---|---|---|
| CM 491 | 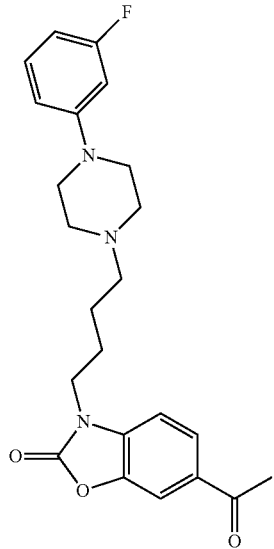 [SMILES: CC(=O)c1ccc2c(c1)oc(=O)n2CCCCN1CCN(c2cccc(F)c2)CC1] | | |
| CM 498 | 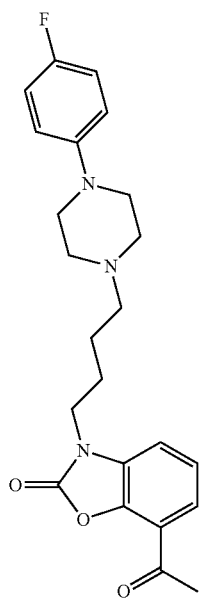 [SMILES: CC(=O)c1cccc2c1oc(=O)n2CCCCN1CCN(c2ccc(F)cc2)CC1] | | |

-continued
| CMPD | STRUCTURE | Ki (nM) σ₁ | Ki (nM) σ₂ |
|---|---|---|---|
| CM 500 | 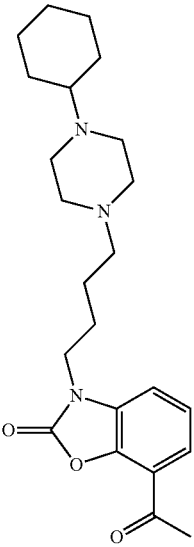 [SMILES: CC(=O)c1cccc2c1oc(=O)n2CCCCN1CCN(C2CCCCC2)CC1] | | |
| CM 504 | 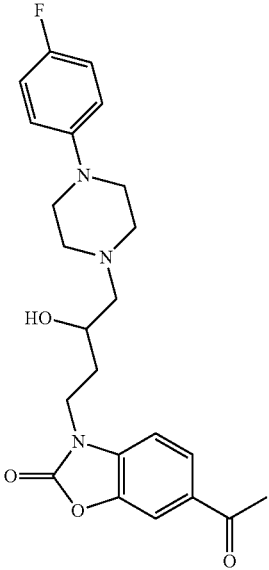 [SMILES: CC(=O)c1ccc2c(c1)oc(=O)n2CCC(O)CN1CCN(c2ccc(F)cc2)CC1] | | |
| CM 528 | 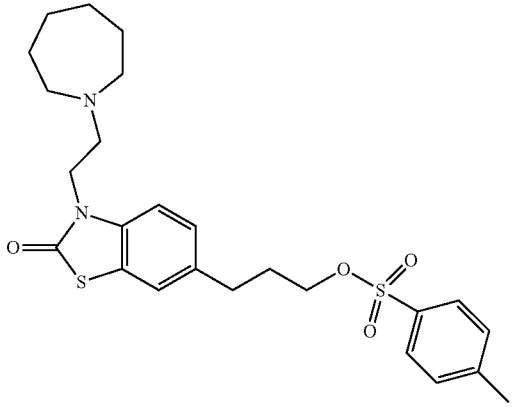 [SMILES: Cc1ccc(S(=O)(=O)OCCCc2ccc3c(c2)sc(=O)n3CCN2CCCCCC2)cc1] | | |

-continued
| CMPD | STRUCTURE | Ki (nM) $\sigma_1$ | Ki (nM) $\sigma_2$ |
|---|---|---|---|
| CM 538 | 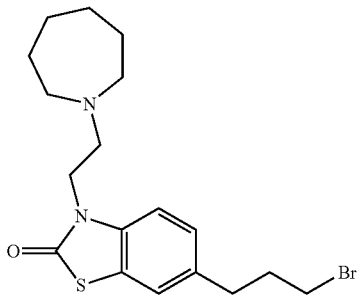 [SMILES: O=c1sc2cc(CCCBr)ccc2n1CCN1CCCCCC1] | | |
| CM 539 | 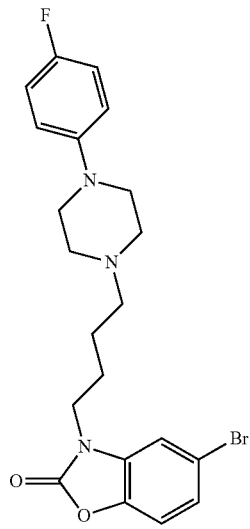 [SMILES: O=c1oc2ccc(Br)cc2n1CCCCN1CCN(c2ccc(F)cc2)CC1] | | |
| CM 540 | 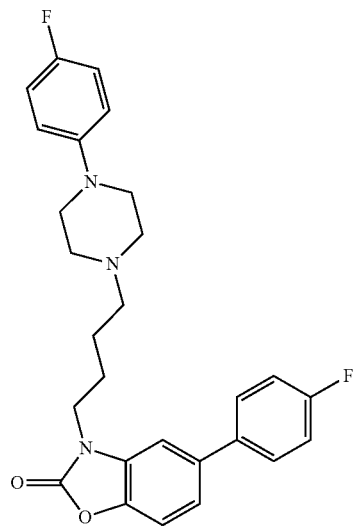 [SMILES: O=c1oc2ccc(-c3ccc(F)cc3)cc2n1CCCCN1CCN(c2ccc(F)cc2)CC1] | | |

| CMPD | STRUCTURE | Ki (nM) σ₁ | Ki (nM) σ₂ |
|---|---|---|---|
| CM 563 | 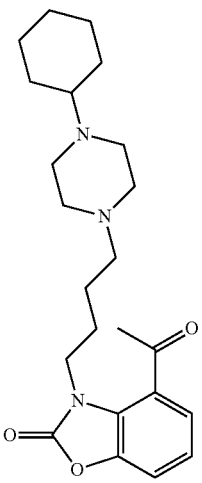 [SMILES: CC(=O)c1cccc2oc(=O)n(CCCCN3CCN(C4CCCCC4)CC3)c12] | | |
| CM 564 | 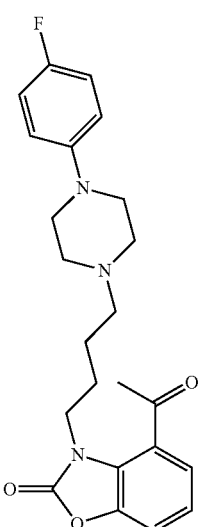 | | |
| CM 566 | 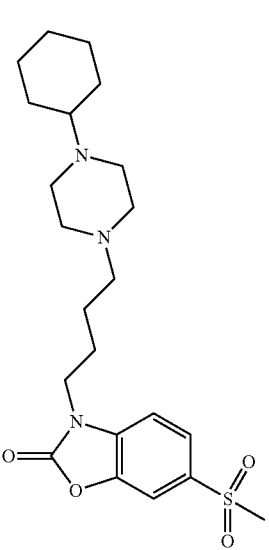 [SMILES: CS(=O)(=O)c1ccc2c(c1)oc(=O)n2CCCCN1CCN(C2CCCCC2)CC1] | | |

-continued
| CMPD | STRUCTURE | Ki (nM) σ₁ | Ki (nM) σ₂ |
|---|---|---|---|
| CM 567 | 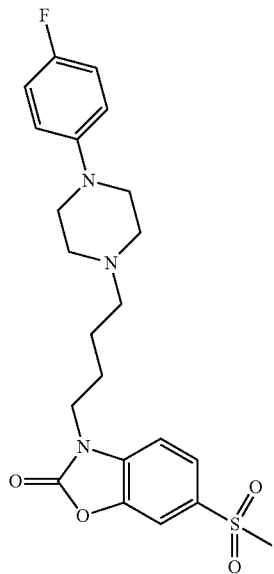 [SMILES: CS(=O)(=O)c1ccc2c(c1)oc(=O)n2CCCCN1CCN(c2ccc(F)cc2)CC1] | | |
| CM 569 | 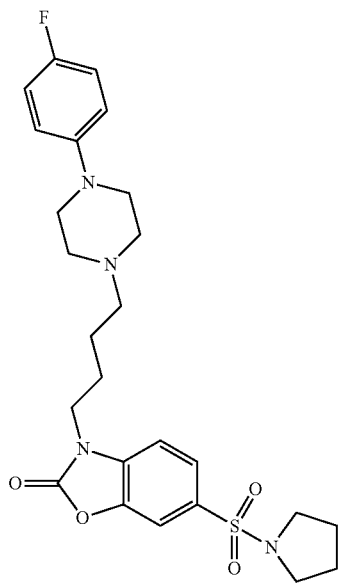 [SMILES: O=c1oc2cc(S(=O)(=O)N3CCCC3)ccc2n1CCCCN1CCN(c2ccc(F)cc2)CC1] | | |

| CMPD | STRUCTURE | Ki (nM) $\sigma_1$ | Ki (nM) $\sigma_2$ |
|---|---|---|---|
| CM 571 | 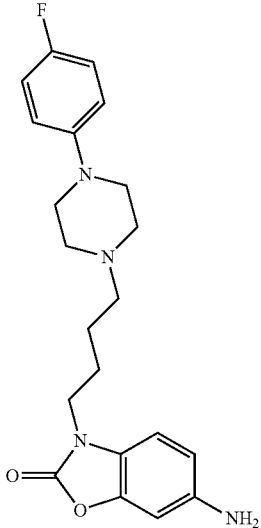 [SMILES: Nc1ccc2c(c1)oc(=O)n2CCCCN1CCN(c2ccc(F)cc2)CC1] | | |
| CM 572 | 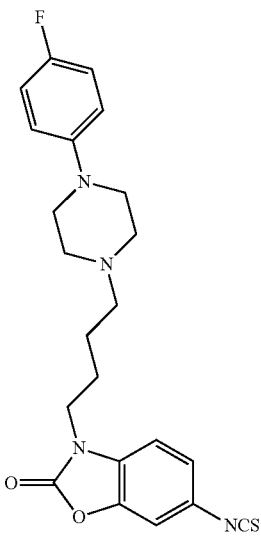 | | |
| CM 585 | 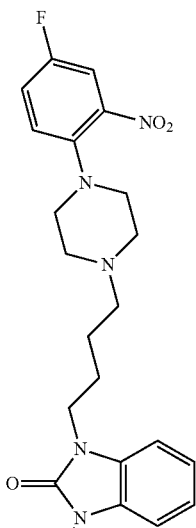 | | |

-continued
| CMPD | STRUCTURE | Ki (nM) σ₁ | Ki (nM) σ₂ |
|---|---|---|---|
| CM 592 | 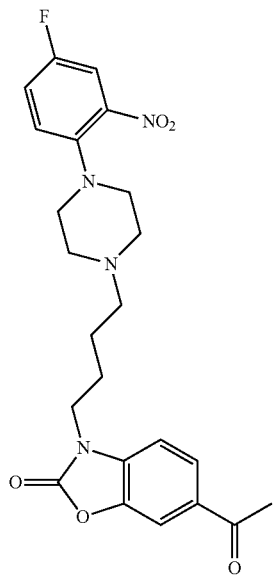 | 369.1 ± 14.2 | 6.30 ± 0.39 |
| CM 599 | 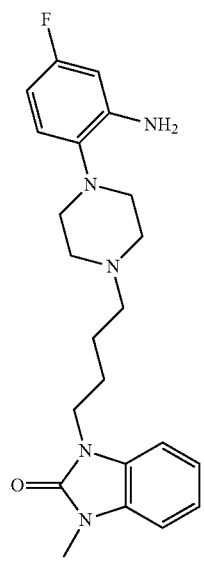 [SMILES: Cn1c(=O)n(CCCCN2CCN(c3ccc(F)cc3[N+](=O)[O-])CC2)c2ccccc21] | 215.7 ± 11.8 | 3.59 ± 0.12 |

-continued
| CMPD | STRUCTURE | Ki (nM) σ₁ | Ki (nM) σ₂ |
|---|---|---|---|
| CM 600 | 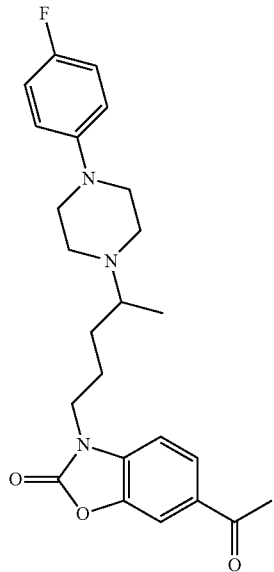 [SMILES: CC(=O)c1ccc2c(c1)oc(=O)n2CCCC(C)N1CCN(c2ccc(F)cc2)CC1] | 27.1 ± 2.32 | 2.15 ± 0.09 |
| CM 608 | 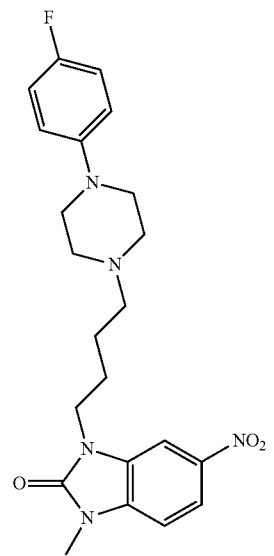 [SMILES: Cn1c(=O)n(CCCCN2CCN(c3ccc(F)cc3)CC2)c2cc([N+](=O)[O-])ccc21] | 15.5 ± 1.75 | 4.72 ± 0.42 |

-continued
| CMPD | STRUCTURE | Ki (nM) $\sigma_1$ | Ki (nM) $\sigma_2$ |
|---|---|---|---|
| CM 609 | 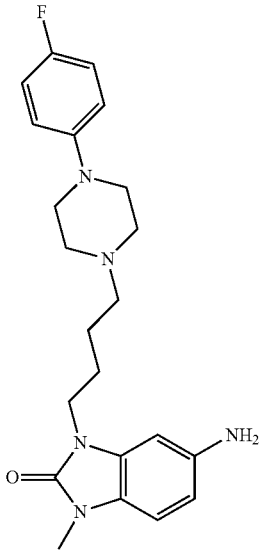 [SMILES: Cn1c(=O)n(CCCCN2CCN(c3ccc(F)cc3)CC2)c2cc(N)ccc21] | 23.4 ± 2.63 | 26.6 ± 2.74 |
| CM 617 | 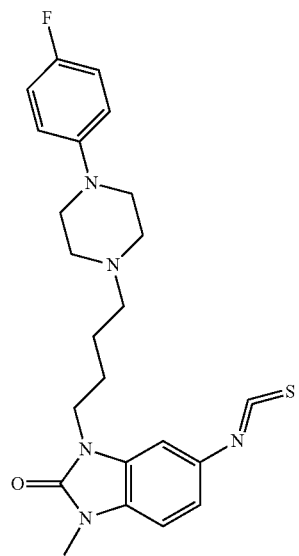 [SMILES: Cn1c(=O)n(CCCCN2CCN(c3ccc(F)cc3)CC2)c2cc(N=C=S)ccc21] | 97.4 ± 6.20 | 30.1 ± 3.42 |

-continued
| CMPD | STRUCTURE | Ki (nM) $\sigma_1$ | Ki (nM) $\sigma_2$ |
|---|---|---|---|
| CM 621 | 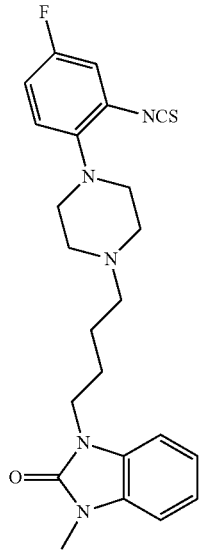 | 96.5 ± 5.80 | 12.60 ± 1.01 |
| CM 623 | 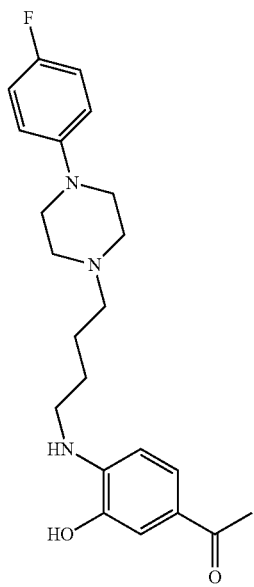 [SMILES: CC(=O)c1ccc(NCCCCN2CCN(c3ccc(F)cc3)CC2)c(O)c1] | 29.4 ± 3.93 | 44.1 ± 3.40 |

-continued
| CMPD | STRUCTURE | Ki (nM) σ₁ | Ki (nM) σ₂ |
|---|---|---|---|
| CM 624 | 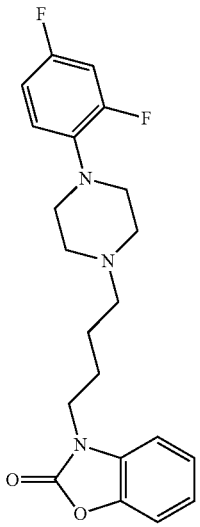 [SMILES: O=c1oc2ccccc2n1CCCCN1CCN(c2ccc(F)cc2F)CC1] | 14.8 ± 0.71 | 1.96 ± 0.11 |
| CM 625 | 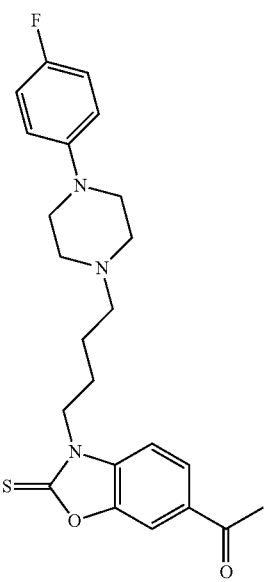 [SMILES: CC(=O)c1ccc2c(c1)oc(=S)n2CCCCN1CCN(c2ccc(F)cc2)CC1] | 10.8 ± 0.78 | 1.88 ± 0.13 |

-continued

| CMPD | STRUCTURE | Ki (nM) $\sigma_1$ | Ki (nM) $\sigma_2$ |
|---|---|---|---|
| CM 627 | 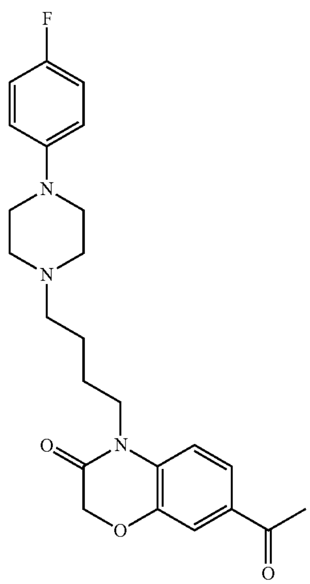 [SMILES: CC(=O)c1ccc2c(c1)OCC(=O)N2CCCCN1CCN(c2ccc(F)cc2)CC1] | 25.5 ± 1.11 | 6.34 ± 0.17 |
| CM 657 | 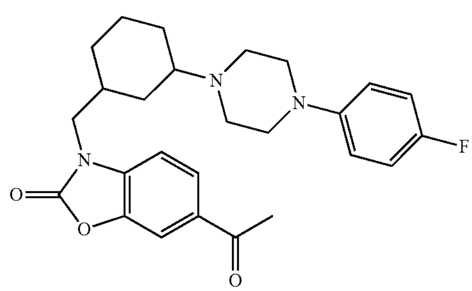 [SMILES: CC(=O)c1ccc2c(c1)oc(=O)n2CC1CCCC(N2CCN(c3ccc(F)cc3)CC2)C1] | 12.7 ± 1.06 | 5.99 ± 0.59 |
| CM 666 | 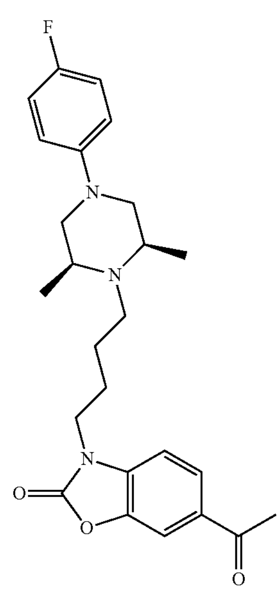 [SMILES: CC(=O)c1ccc2c(c1)oc(=O)n2CCCCN1[C@H](C)CN(c2ccc(F)cc2)C[C@@H]1C] | 21.2 ± 2.34 | 14.9 ± 0.52 |

-continued
| CMPD | STRUCTURE | Ki (nM) σ₁ | Ki (nM) σ₂ |
|---|---|---|---|
| CM 673 | 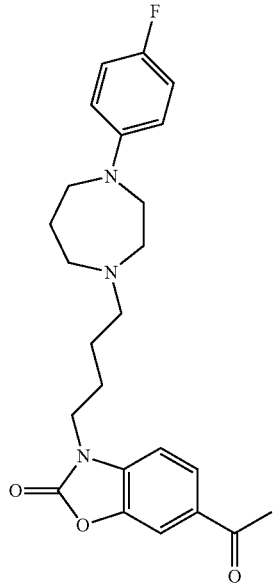 [SMILES: CC(=O)c1ccc2c(c1)oc(=O)n2CCCCN1CCCN(c2ccc(F)cc2)CC1] | 104.1 ± 8.06 | 50.6 ± 4.32 |
| CM 697 | 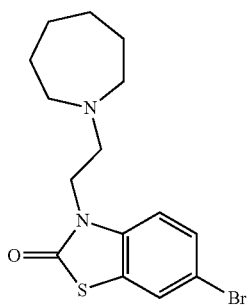 [SMILES: O=c1sc2cc(Br)ccc2n1CCN1CCCCCC1] | | |
| CM 699 | 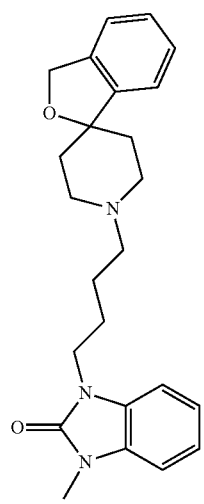 [SMILES: Cn1c(=O)n(CCCCN2CCC3(CC2)OCc2ccccc23)c2ccccc21] | | |

| CMPD | STRUCTURE | Ki (nM) $\sigma_1$ | Ki (nM) $\sigma_2$ |
|---|---|---|---|
| CM 711 | 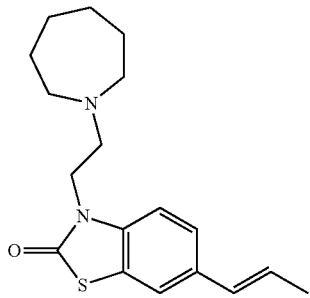 [SMILES: C/C=C/c1ccc2c(c1)sc(=O)n2CCN1CCCCCC1] | | |
| CM 728 | 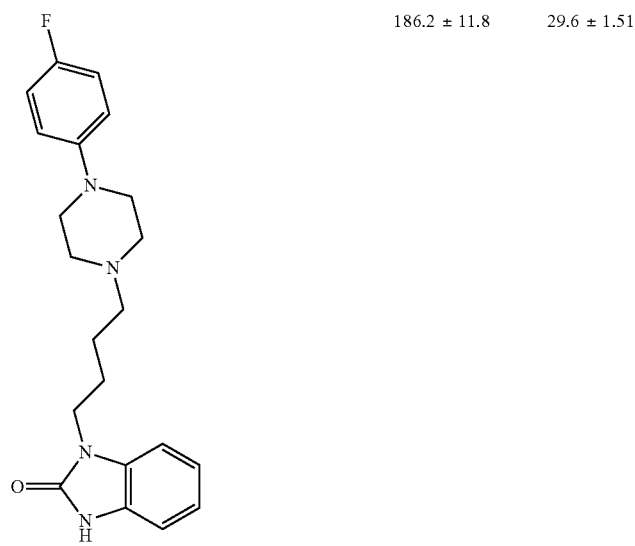 | 186.2 ± 11.8 | 29.6 ± 1.51 |
| CM 764 | 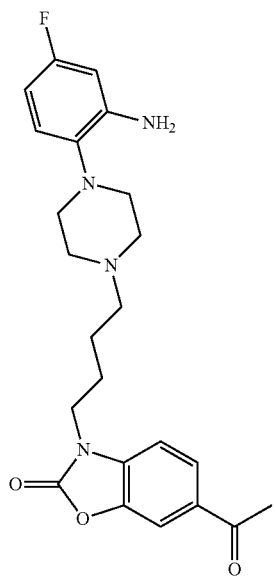 | | |

-continued
| CMPD | STRUCTURE | Ki (nM) σ₁ | Ki (nM) σ₂ |
|---|---|---|---|
| CM 768 | 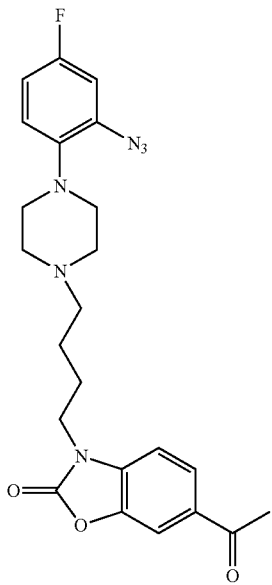 [SMILES: CC(=O)c1ccc2c(c1)oc(=O)n2CCCCN1CCN(c2ccc(F)cc2N=[N+]=[N-])CC1] | | |
| CM 769 | 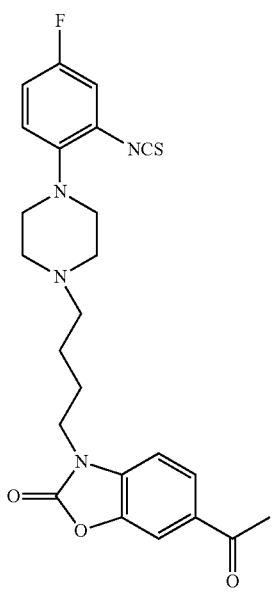 | | |

| CMPD | STRUCTURE | Ki (nM) $\sigma_1$ | Ki (nM) $\sigma_2$ |
| --- | --- | --- | --- |
| CM 775 | 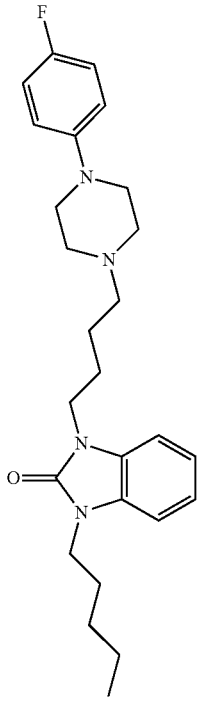 [SMILES: CCCCCn1c(=O)n(CCCCN2CCN(c3ccc(F)cc3)CC2)c2ccccc21] | | |
| CM 777 | 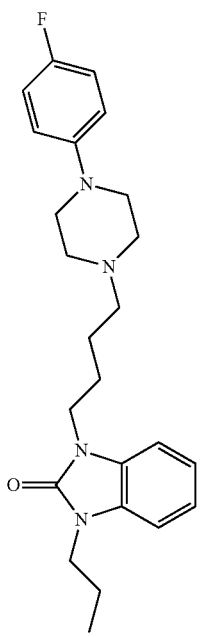 [SMILES: CCCn1c(=O)n(CCCCN2CCN(c3ccc(F)cc3)CC2)c2ccccc21] | | |

-continued
| CMPD | STRUCTURE | Ki (nM) $\sigma_1$ | Ki (nM) $\sigma_2$ |
|---|---|---|---|
| CM 778 | 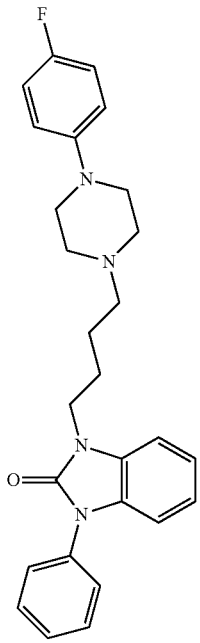 [SMILES: O=c1n(CCCCN2CCN(c3ccc(F)cc3)CC2)c2ccccc2n1-c1ccccc1] | | |
| CM 781 | 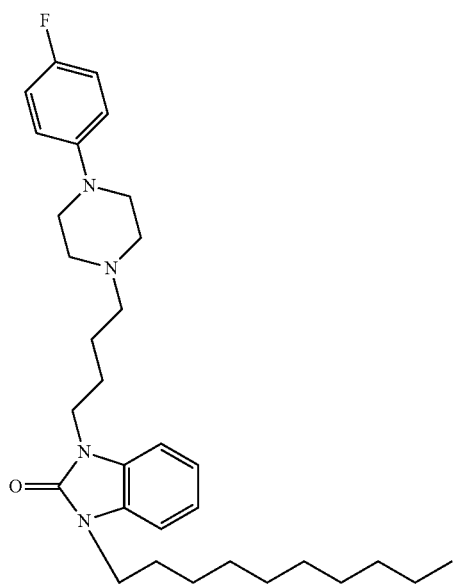 [SMILES: CCCCCCCCCCn1c(=O)n(CCCCN2CCN(c3ccc(F)cc3)CC2)c2ccccc21] | | |

| CMPD | STRUCTURE | Ki (nM) σ₁ | Ki (nM) σ₂ |
|---|---|---|---|
| CM 782 | 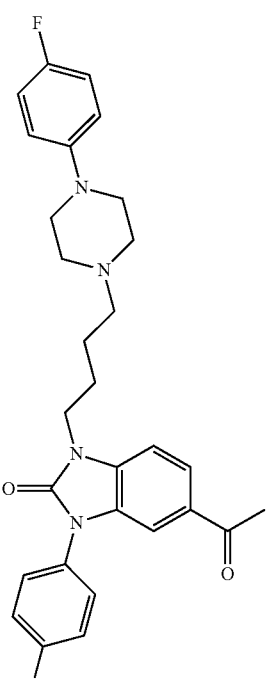 | | |
| CMPD | STRUCTURE | Ki (nm) σ₁ | Ki (nm) σ₂ |
|---|---|---|---|
| NF6 | 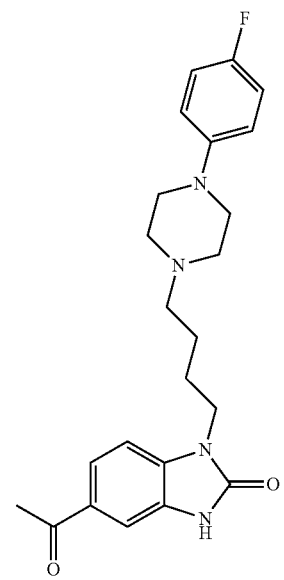 [SMILES: CC(=O)c1ccc2c(c1)[nH]c(=O)n2CCCCN1CCN(c2ccc(F)cc2)CC1] | | |

| CMPD | STRUCTURE | Ki (nm) σ1 | Ki (nm) σ2 |
|---|---|---|---|
| NF7 | 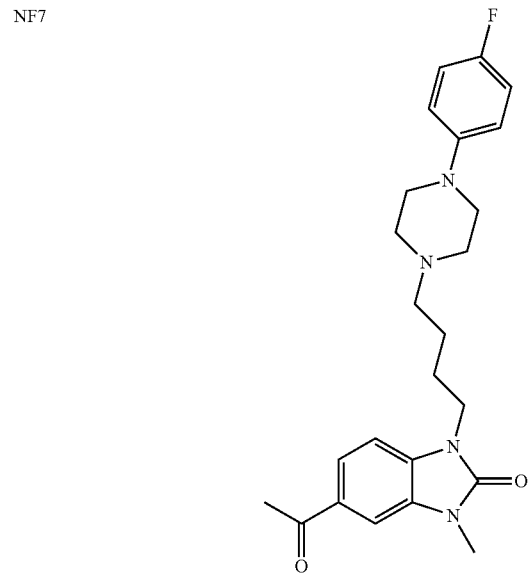 | | |
| NF8 | 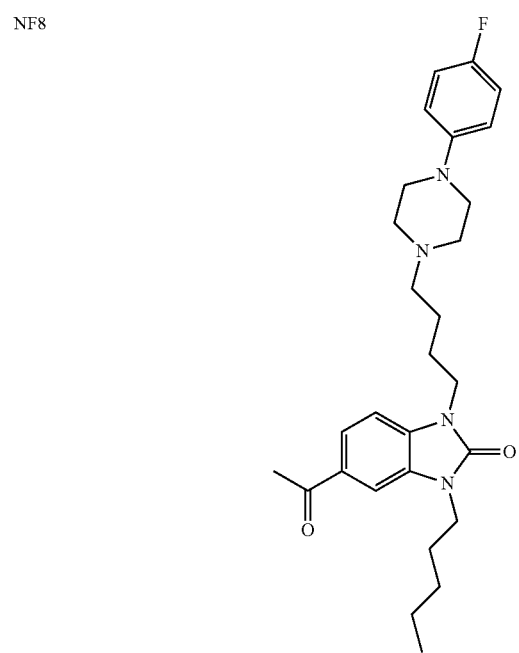 | | |

| CMPD | STRUCTURE | Ki (nm) $\sigma_1$ | Ki (nm) $\sigma_2$ |
|---|---|---|---|
| NF9 | 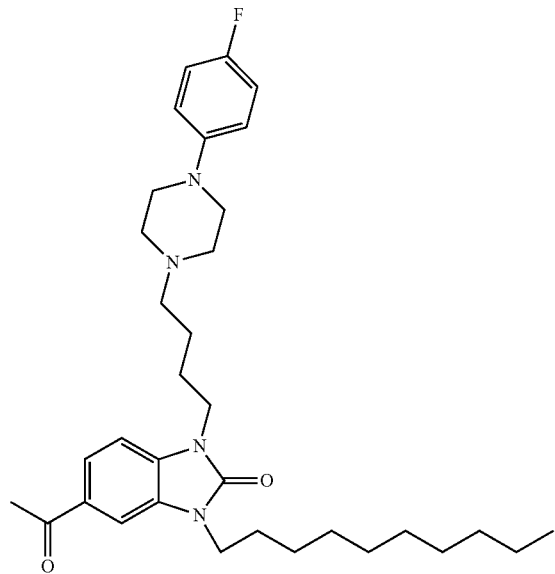 [SMILES: CCCCCCCCCCn1c(=O)n(CCCCN2CCN(c3ccc(F)cc3)CC2)c2ccc(C(C)=O)cc21] | | |
| NF10 | 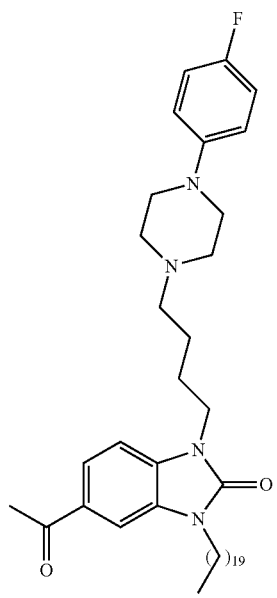 | | |

-continued
| CMPD | STRUCTURE | Ki (nm) σ₁ | Ki (nm) σ₂ |
|---|---|---|---|
| NF12 | 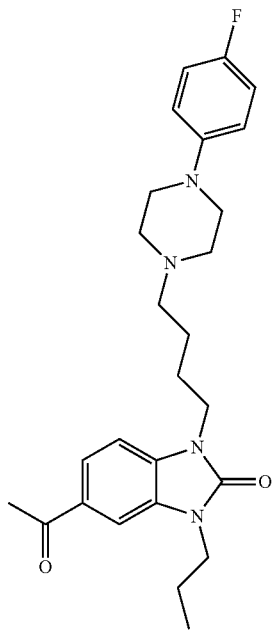 [SMILES: CCCn1c(=O)n(CCCCN2CCN(c3ccc(F)cc3)CC2)c2ccc(C(C)=O)cc21] | | |
| EA2 | 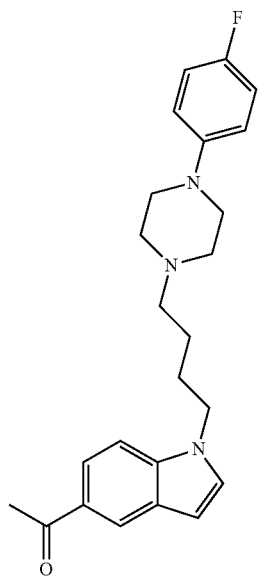 [SMILES: CC(=O)c1ccc2c(ccn2CCCCN2CCN(c3ccc(F)cc3)CC2)c1] | | |

| CMPD | STRUCTURE | Ki (nm) σ$_1$ | Ki (nm) σ$_2$ |
|---|---|---|---|
| EA6 | 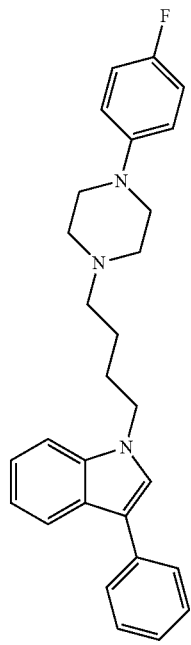 [SMILES: Fc1ccc(N2CCN(CCCCn3cc(-c4ccccc4)c4ccccc43)CC2)cc1] | | |
| EA7 | 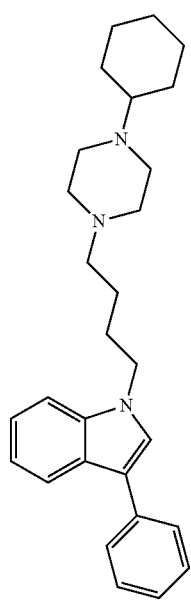 [SMILES: c1ccc(-c2cn(CCCCN3CCN(C4CCCCC4)CC3)c3ccccc23)cc1] | | |

-continued
| CMPD | STRUCTURE | Ki (nm) σ$_1$ | Ki (nm) σ$_2$ |
|---|---|---|---|
| EA8 | 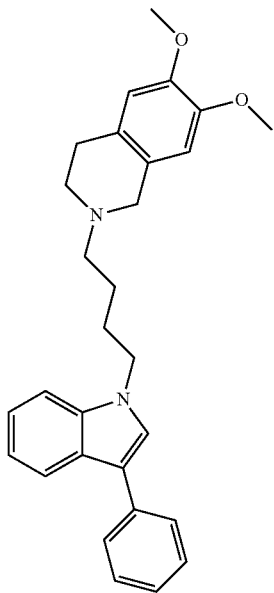 [SMILES: COc1cc2c(cc1OC)CN(CCCCn1cc(-c3ccccc3)c3ccccc31)CC2] | | |
| EA12 | 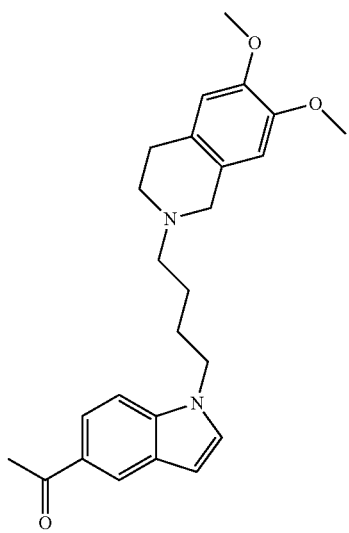 [SMILES: COc1cc2c(cc1OC)CN(CCCCn1ccc3cc(C(C)=O)ccc31)CC2] | | |

-continued
| CMPD | STRUCTURE | Ki (nm) $\sigma_1$ | Ki (nm) $\sigma_2$ |
|---|---|---|---|
| EA13 | 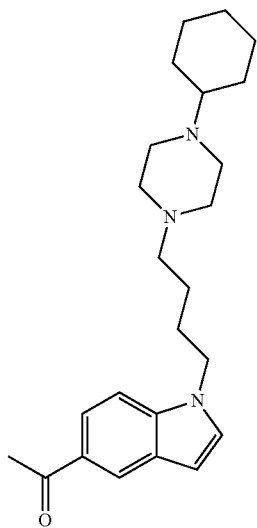 [SMILES: CC(=O)c1ccc2c(ccn2CCCCN2CCN(C3CCCCC3)CC2)c1] | | |
| EA14 | 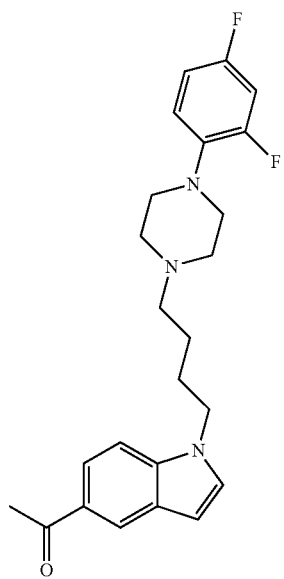 [SMILES: CC(=O)c1ccc2c(ccn2CCCCN2CCN(c3ccc(F)cc3F)CC2)c1] | | |

| CMPD | STRUCTURE | Ki (nm) σ₁ | Ki (nm) σ₂ |
|------|-----------|------------|------------|
| EA18 | 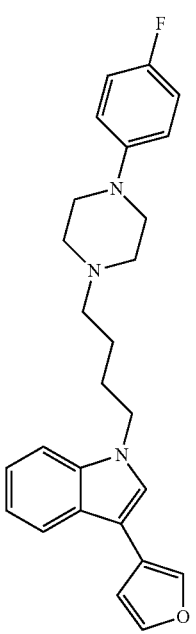 [SMILES: Fc1ccc(N2CCN(CCCCn3cc(-c4ccoc4)c4ccccc43)CC2)cc1] | | |
| EA21 | 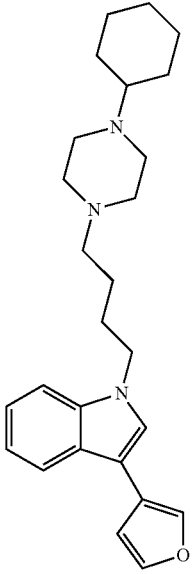 [SMILES: c1ccc2c(c1)c(-c1ccoc1)cn2CCCCN1CCN(C2CCCCC2)CC1] | | |
| SN-228 | 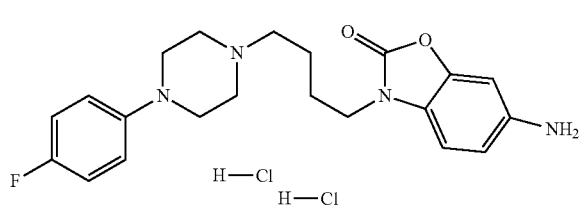 | >10000 | 177.47 ± 10.16 |

| CMPD | STRUCTURE | Ki (nm) $\sigma_1$ | Ki (nm) $\sigma_2$ |
|---|---|---|---|
| SN-248 | 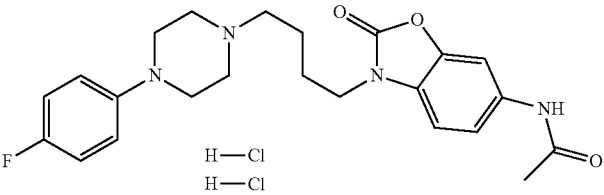 | 88.43 ± 12.72 | 48.13 ± 5.68 |
| SN-249 | 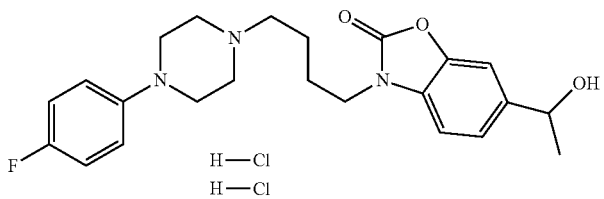 | 608.9 ± 39.75 | 8.68 ± 0.57 |
| SN-250 | 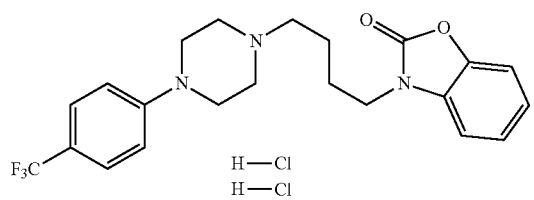 | 87.58 ± 8.77 | 98.81 ± 1.08 |
| SN-251 | 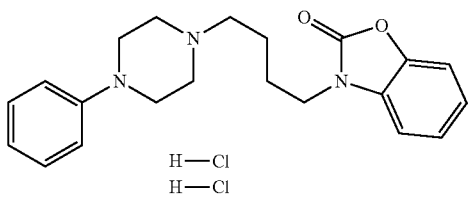 | 18.35 ± 1.46 | 11.44 ± 1.15 |
| SN-252 | 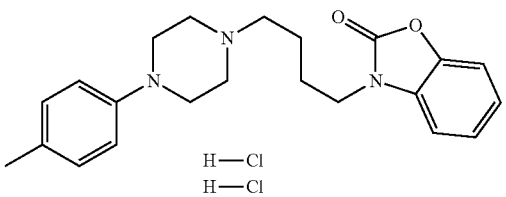 | 212.8 ± 22.24 | 107.02 ± 8.21 |
| SN-253 | 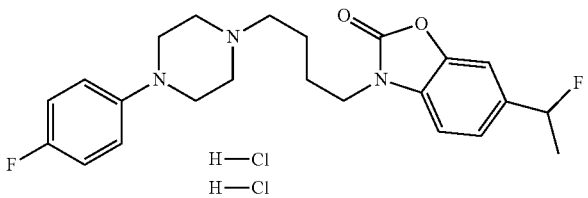 | 162.3 ± 11.45 | 6.12 ± 0.37 |

-continued
| CMPD | STRUCTURE | Ki (nm) $\sigma_1$ | Ki (nm) $\sigma_2$ |
|---|---|---|---|
| SC-5 | 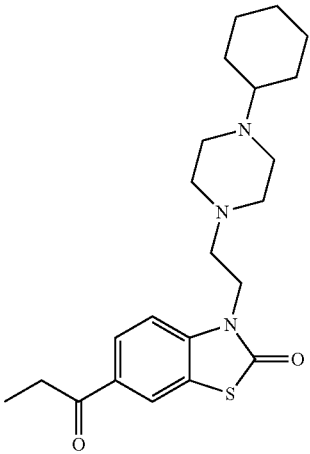 [SMILES: CCC(=O)c1ccc2c(c1)sc(=O)n2CCN1CCN(C2CCCCC2)CC1] | 6.75 ± 0.6 | 3.73 ± 0.43 |
| SC-6 | 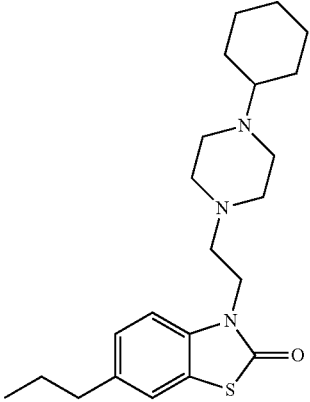 | 2.15 ± 0.25 | 2.43 ± 0.09 |
| SC-10 | 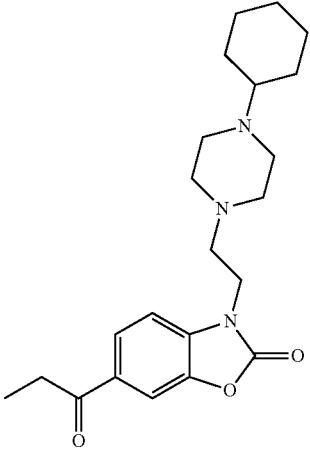 [SMILES: CCC(=O)c1ccc2c(c1)oc(=O)n2CCN1CCN(C2CCCCC2)CC1] | 14.3 ± 0.34 | 4.85 ± 0.31 |

-continued
| CMPD | STRUCTURE | Ki (nm) $\sigma_1$ | Ki (nm) $\sigma_2$ |
|---|---|---|---|
| SC-12 | 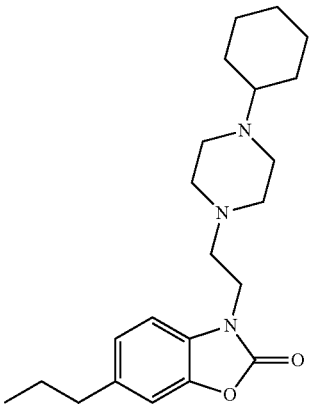 [SMILES: CCCc1ccc2c(c1)oc(=O)n2CCN1CCN(C2CCCCC2)CC1] | 7.50 ± 0.59 | 4.02 ± 0.23 |
| CMPD | STRUCTURE | Ki (nm) $\sigma_1$ | Ki (nm) $\sigma_2$ |
|---|---|---|---|
| AZ-57 | 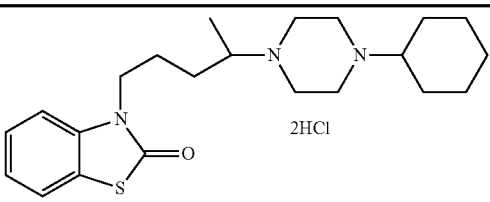<br>Chemical Formula: $C_{22}H_{35}Cl_2N_3OS$<br>Exact Mass: 459.19 | 8.73 ± 1.32 | 3.15 ± 0.19 |
| AZ-59 | 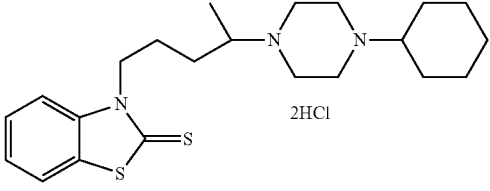<br>Chemical Formula: $C_{22}H_{35}Cl_2N_3S_2$<br>Exact Mass: 475.16 | 8.94 ± 1.64 | 0.99 ± 0.178 |
| AZ-60 | 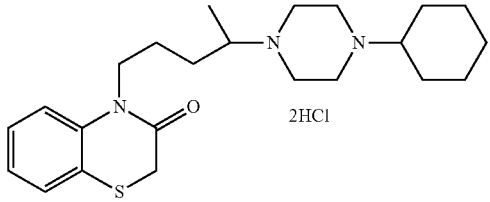<br>Chemical Formula: $C_{23}H_{37}Cl_2N_3OS$<br>Exact Mass: 473.20 | 92.36 ± 9.76 | 5.49 ± 1.10 |
| AZ-66 | 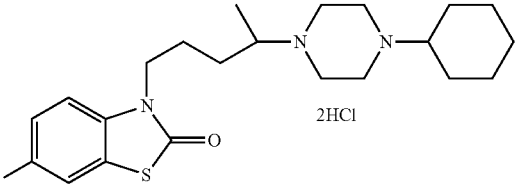<br>Chemical Formula: $C_{22}H_{34}Cl_2FN_3OS$<br>Exact Mass: 477.18 | 0.31 ± 0.09 | 1.76 ± 0.34 |

-continued
AZ-68 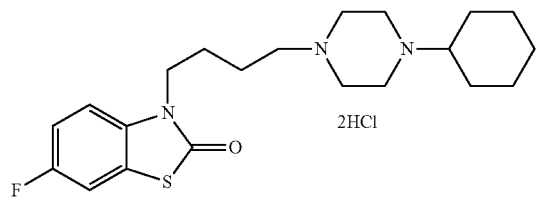 2.01 ± 0.44   0.22 ± 0.09
2HCl
Chemical Formula: $C_{21}H_{32}Cl_2FN_3OS$
Exact Mass: 463.16
AZ-70 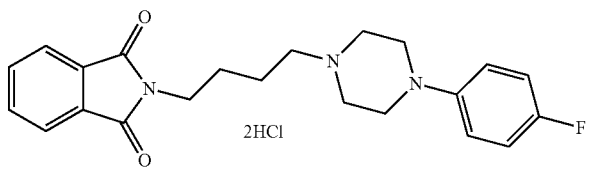
2HCl
Chemical Formula: $C_{22}H_{26}Cl_2FN_3O_2$
Exact Mass: 453.14
AZ-71 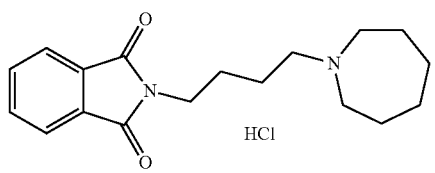
HCl
Chemical Formula: $C_{18}H_{25}ClN_2O_2$
Exact Mass: 336.16
AZ-72 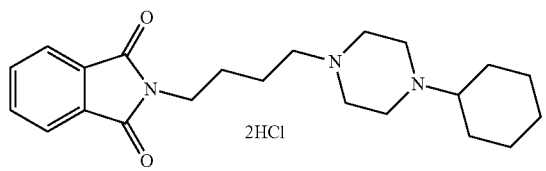
2HCl
Chemical Formula: $C_{22}H_{33}Cl_2N_3O_2$
Exact Mass: 441.19
AZ-73 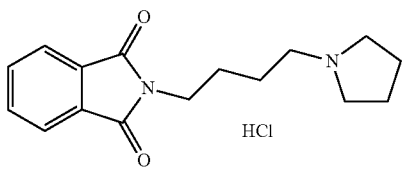
HCl
Chemical Formula: $C_{16}H_{21}ClN_2O_2$
Exact Mass: 308.13
AZ-74 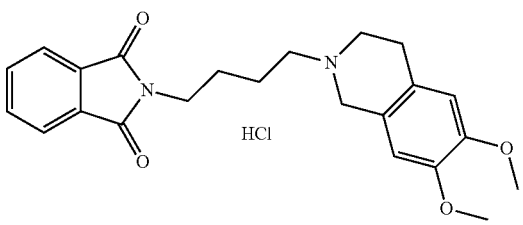
HCl
Chemical Formula: $C_{23}H_{27}ClN_2O_4$
Exact Mass: 430.17

-continued
AZ-77
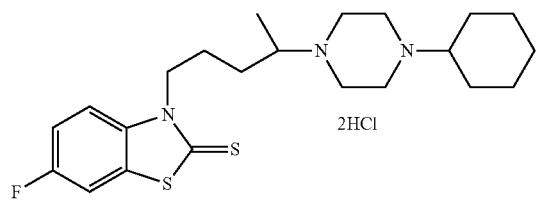
Chemical Formula: $C_{22}H_{34}Cl_2FN_3S_2$
Exact Mass: 493.16
AZ-78
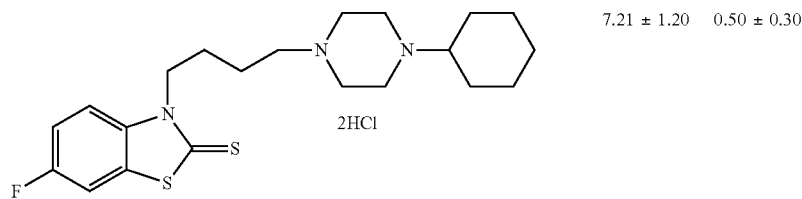
Chemical Formula: $C_{21}H_{32}Cl_2FN_3S_2$
Exact Mass: 479.14
7.21 ± 1.20   0.50 ± 0.30
AZ-81
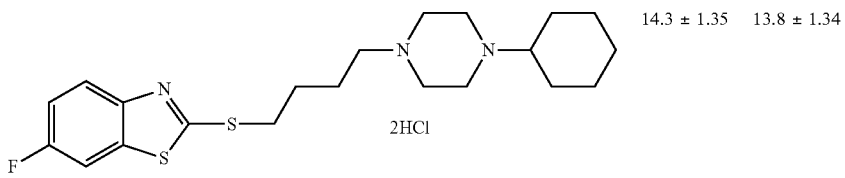
Chemical Formula: $C_{21}H_{32}Cl_2FN_3S_2$
Exact Mass: 479.14
14.3 ± 1.35   13.8 ± 1.34
AZ-87
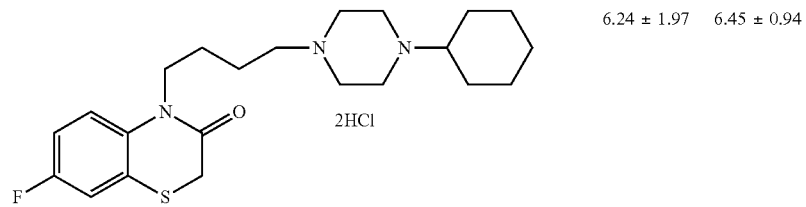
Chemical Formula: $C_{22}H_{34}Cl_2FN_3OS$
Exact Mass: 477.18
6.24 ± 1.97   6.45 ± 0.94
AZ-93
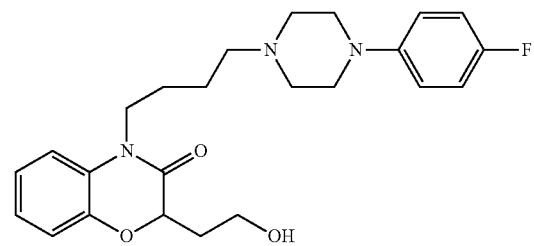
Chemical Formula: $C_{24}H_{30}FN_3O_3$
Exact Mass: 427.23

AZ-94
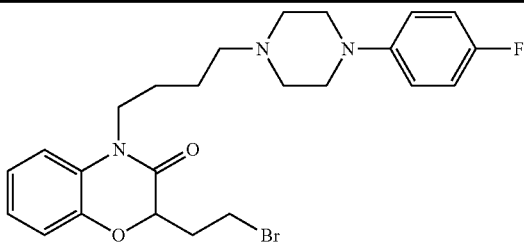
Chemical Formula: $C_{24}H_{39}BrFN_3O_2$
Exact Mass: 489.14
AZ-95
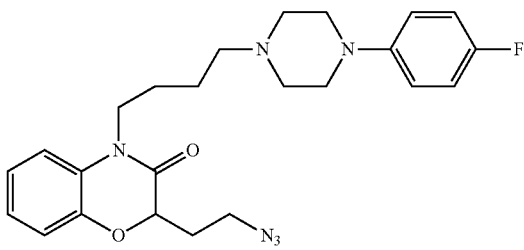
Chemical Formula: $C_{24}H_{29}FN_6O_2$
Exact Mass: 452.23
AZ-96
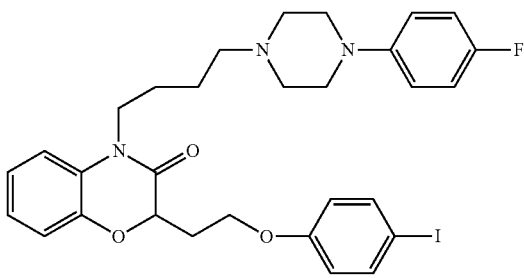
Chemical Formula: $C_{30}H_{33}FIN_3O_3$
Exact Mass: 629.16
AZ-97
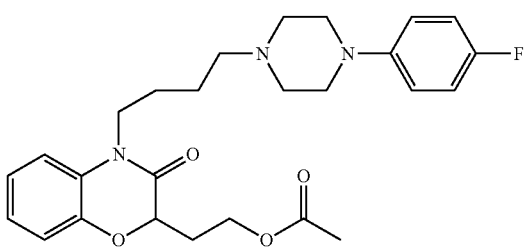
Chemical Formula: $C_{26}H_{32}FN_3O_4$
Exact Mass: 469.24
AZ-98
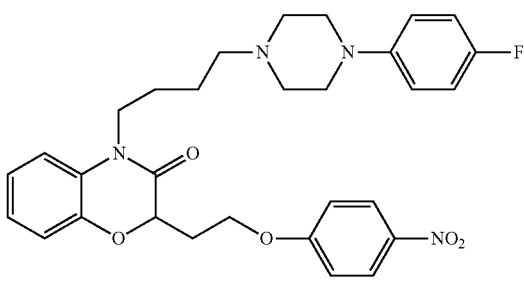
Chemical Formula: $C_{30}H_{33}FN_4O_5$
Exact Mass: 548.24

-continued
AZ-99
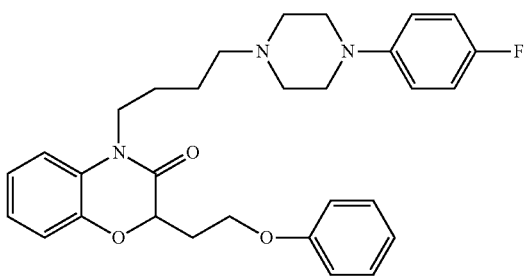
Chemical Formula: $C_{30}H_{34}FN_3O_3$
Exact Mass: 503.26
AZ-100
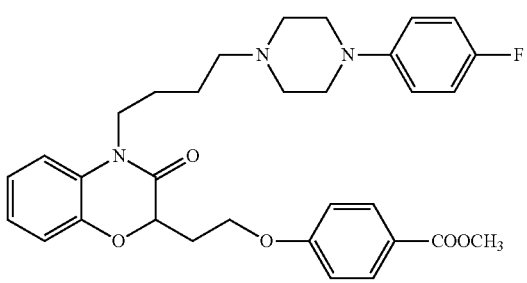
Chemical Formula: $C_{32}H_{36}FN_3O_5$
Exact Mass: 561.26
AZ-101
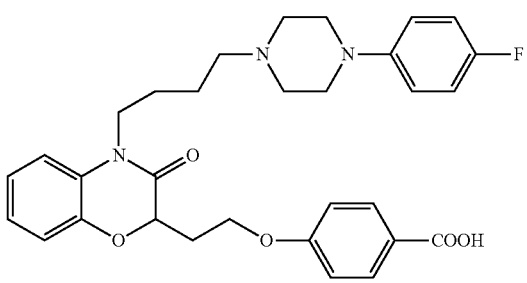
Chemical Formula: $C_{31}H_{34}FN_3O_5$
Exact Mass: 547.25
AZ-102
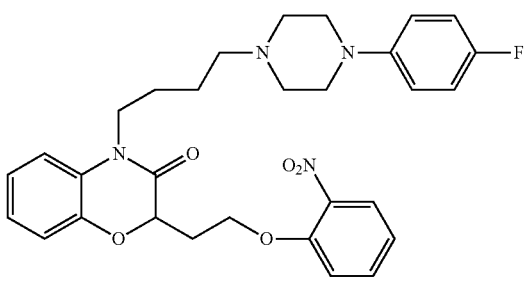
Chemical Formula: $C_{30}H_{33}FN_4O_5$
Exact Mass: 548.24

AZ-103
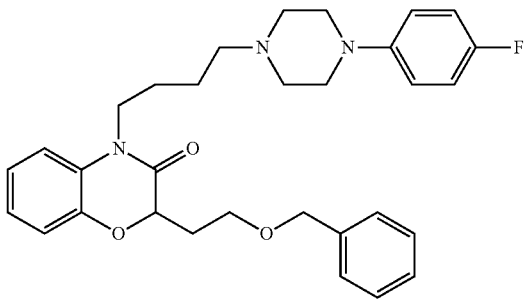
Chemical Formula: C$_{31}$H$_{36}$FN$_3$O$_3$
Exact Mass: 517.27
AZ-104
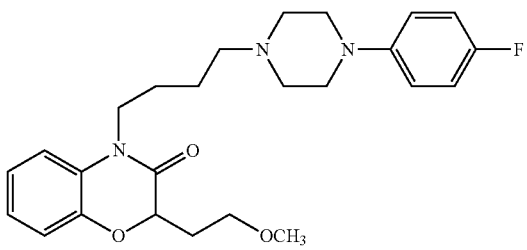
Chemical Formula: C$_{25}$H$_{32}$FN$_3$O$_3$
Exact Mass: 441.24
AZ-105
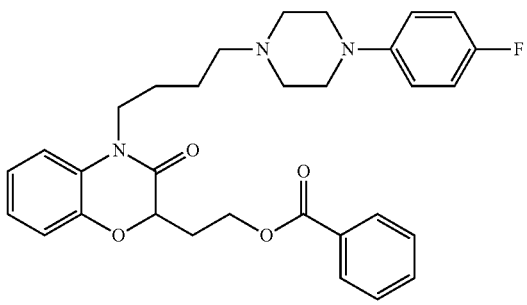
Chemical Formula: C$_{31}$H$_{34}$FN$_3$O$_4$
Exact Mass: 531.25
AZ-106
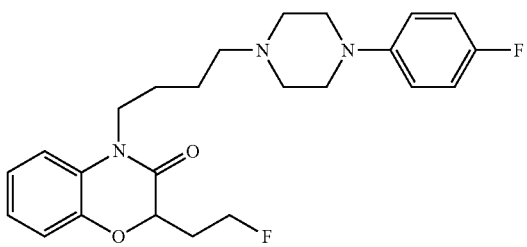
Chemical Formula: C$_{24}$H$_{29}$F$_2$N$_3$O$_2$
Exact Mass: 429.22

AZ-107
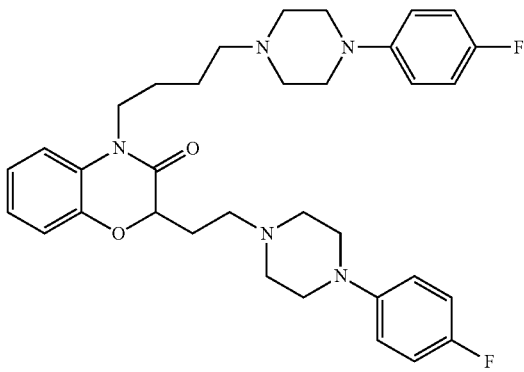
Chemical Formula: $C_{34}H_{41}F_2N_5O_2$
Exact Mass: 589.32
AZ-108
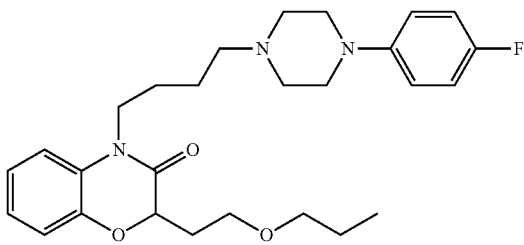
Chemical Formula: $C_{27}H_{36}FN_3O_3$
Exact Mass: 469.27
AZ-109
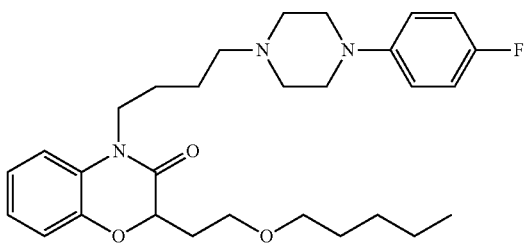
Chemical Formula: $C_{29}H_{40}FN_3O_3$
Exact Mass: 497.31
AZ-110
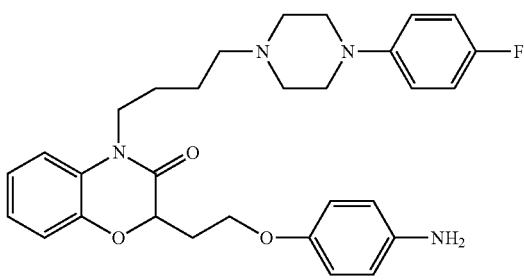
Chemical Formula: $C_{30}H_{35}FN_4O_3$
Exact Mass: 518.27

AZ-112
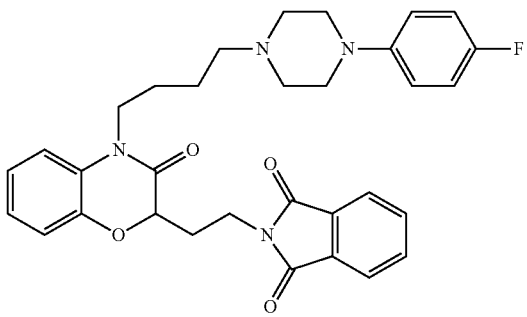
Chemical Formula: $C_{32}H_{33}FN_4O_4$
Exact Mass: 556.25
AZ-113
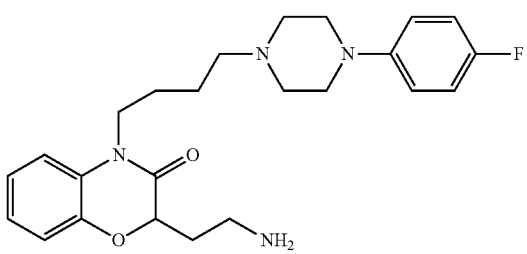
Chemical Formula: $C_{24}H_{31}FN_4O_2$
Exact Mass: 426.24
AZ-114
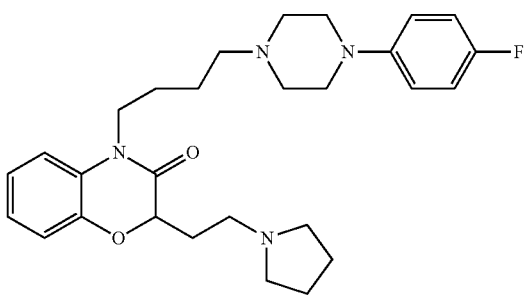
Chemical Formula: $C_{28}H_{37}FN_4O_2$
Exact Mass: 480.29
AZ-115
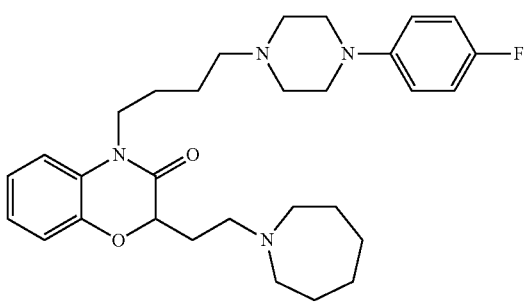
Chemical Formula: $C_{30}H_{41}FN_4O_2$
Exact Mass: 508.32

AZ-116
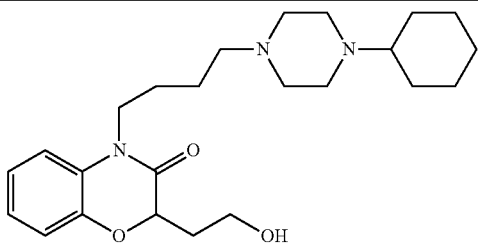
Chemical Formula: $C_{24}H_{37}N_3O_3$
Exact Mass: 415.28
AZ-117
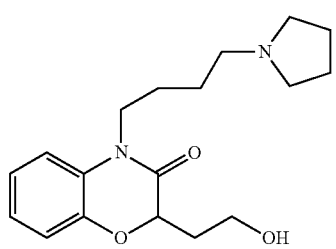
Chemical Formula: $C_{18}H_{26}N_2O_3$
Exact Mass: 318.19
AZ-118
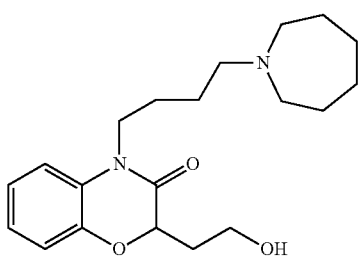
Chemical Formula: $C_{20}H_{30}N_2O_3$
Exact Mass: 346.23
AZ-119
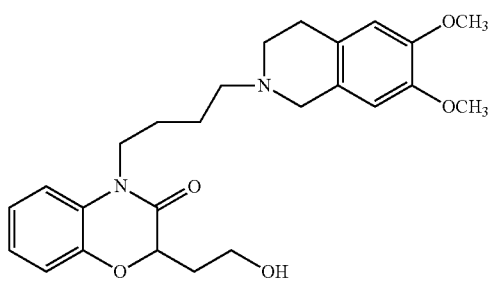
Chemical Formula: $C_{25}H_{32}N_2O_5$
Exact Mass: 440.23
AZ-120
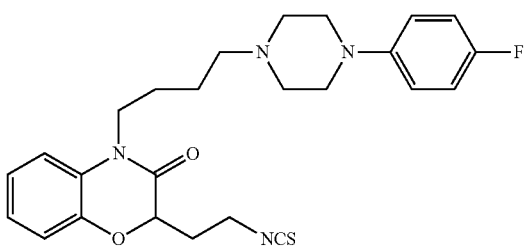
Chemical Formula: $C_{25}H_{29}FN_4O_2S$
Exact Mass: 468.20

AZ-121
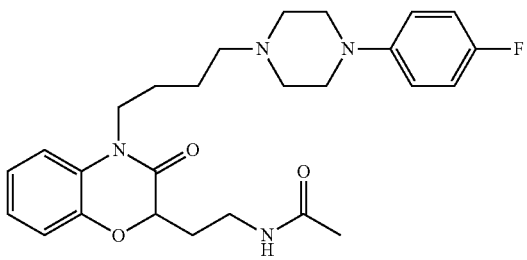
Chemical Formula: $C_{26}H_{33}FN_4O_3$
Exact Mass: 468.25
AZ-122
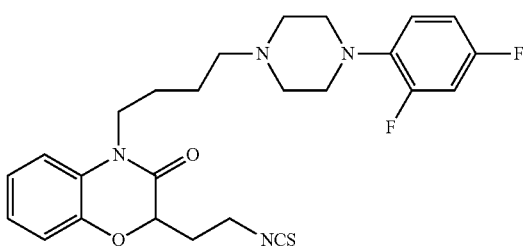
Chemical Formula: $C_{24}H_{29}F_2N_3O_3$
Exact Mass: 445.22
| CMPD | STRUCTURE |
|---|---|
| AZ-9 | 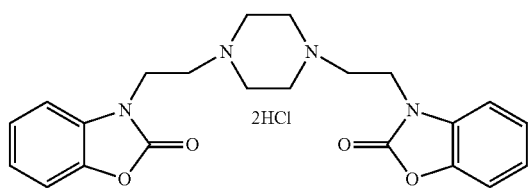<br>Chemical Formula: $C_{22}H_{26}Cl_2N_4O_4$<br>Exact Mass: 480.13 |
| AZ-10 | 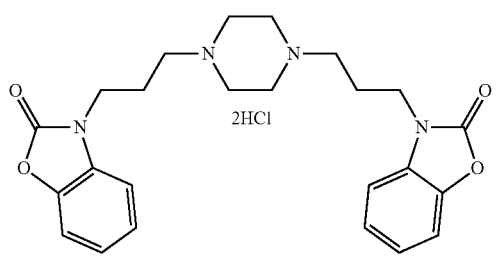<br>Chemical Formula: $C_{24}H_{30}Cl_2N_4O_4$<br>Exact Mass: 508.16 |
| AZ-2 | 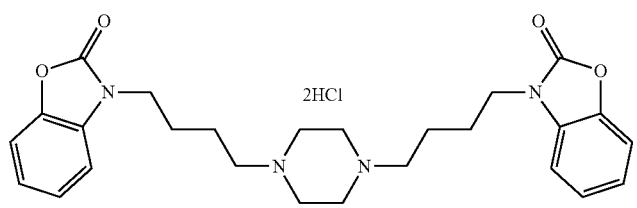<br>Chemical Formula: $C_{26}H_{34}Cl_2N_4O_4$<br>Exact Mass: 536.20 |

AZ-7
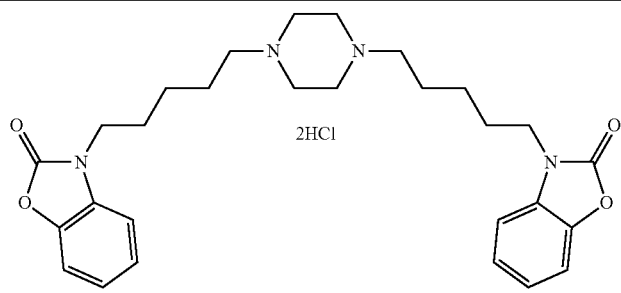
Chemical Formula: $C_{28}H_{38}Cl_2N_4O_4$
Exact Mass: 564.23
AZ-8
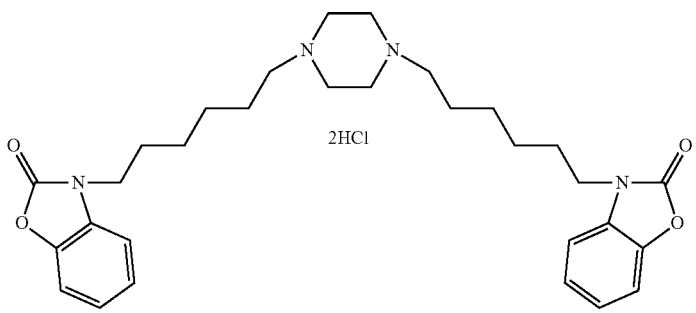
Chemical Formula: $C_{30}H_{42}Cl_2N_4O_4$
Exact Mass: 592.26
AZ-16
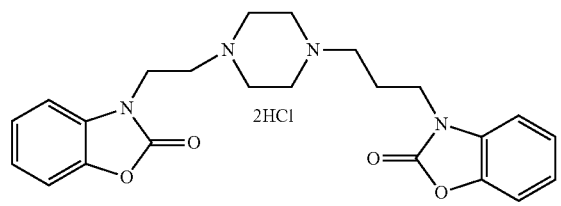
Chemical Formula: $C_{23}H_{28}Cl_2N_4O_4$
Exact Mass: 494.15
AZ-17
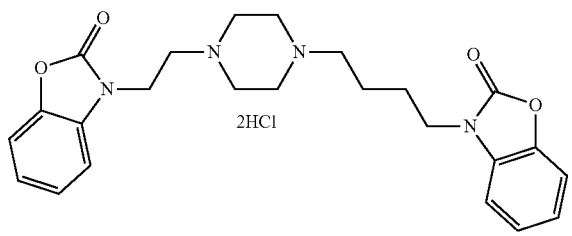
Chemical Formula: $C_{24}H_{30}Cl_2N_4O_4$
Exact Mass: 508.16
AZ-18
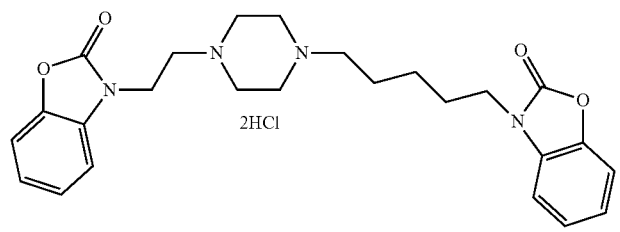
Chemical Formula: $C_{25}H_{32}Cl_2N_4O_4$
Exact Mass: 522.18

The present invention comprises a method of treating a subject for alleviation of affects in the subject resulting from drug intake or drug abuse by the subject comprising administering to the subject a therapeutically effective amount of at least one compound according to the invention.

The drug abuse or drug intake can result from methamphetamine intake or methamphetamine abuse by the subject or from cocaine abuse or cocaine intake by the subject.

The present invention further comprises a method of treating a subject having a need for therapy involving sigma receptors comprising administering to the subject an effective amount of at least one compound of the present invention and additionally comprises treating a subject to prevent neurotoxic effects resulting from drug abuse or drug intake by the subject comprising administering to the subject a therapeutically effective amount of at least one compound according to the invention.

The invention further comprises radioligand compositions comprising at least one compound according to the invention wherein at least one compound contains a radioactive element.

Pharmaceutical compositions according to the invention are those which are suitable for enteral, such as oral, administration and for parenteral, such as subcutaneous, administration to warm-blooded animals, especially humans, and which contain the pharmacologically active substance on its own or together with a pharmaceutically acceptable carrier. The dosage of the active substance depends on the species of warm-blooded animal and on the age and individual condition, the illness to be treated and also on the mode of administration. Such dosage can be readily determined by those practicing in the relevant art area.

The novel pharmaceutical preparations contain from approximately 10% to approximately 95%, and preferably from approximately 20% to approximately 90%, of the active substance. Pharmaceutical compositions according to the invention can, for example, be in unit dose form, such as dragees, tablets, capsules, suppositories or ampoules.

The pharmaceutical compositions of the present invention are manufactured in a manner known per se, for example, by means of conventional mixing, granulating, confectioning, dissolving or lyophilizing processes. Pharmaceutical compositions for oral use can be obtained by combining the active substance with one or more solid carriers, if desired, granulating a resulting mixture and processing the mixture or granulate, if desired or necessary after the addition of suitable adjuncts, to form tablets or dragee cores. In so doing, they can also be incorporated into plastics carriers which release the active substances or allow them to diffuse in controlled amounts.

Suitable carriers are especially fillers such as sugars, for example, lactose, saccharose, mannitol or sorbitol, cellulose preparations and/or calcium phosphates, for example, tricalcium phosphate or calcium hydrogen phosphate, also binders such as starches, for example, corn, wheat, rice or potato starch, gelatine, tragacanth, methylcellulose, hydroxypropylmethylcellulose, sodium carboxymethylcellulose and/or polyvinylpyrrolidone, and/or, if desired, disintegrators such as the above-mentioned starches, also carboxymethyl starch, cross-linked polyvinylpyrrolidone, agar, alginic acid or a salt thereof such as sodium alginate. Adjuncts are especially flow-regulating and lubricating agents, for example, silica, talc, stearic acid or salts thereof such as magnesium or calcium stearate, and/or polyethylene glycol. Dragee cores are provided with suitable coatings that are, if desired, resistant to gastric juice, there being used, inter alia, concentrated sugar solutions which optionally contain gum arabic, talc, polyvinylpyrrolidone, polyethylene glycol and/or titanium dioxide, lacquer solutions in suitable organic solvents or solvent mixtures or, for the manufacture of coatings that are resistant to gastric juice, solutions of suitable cellulose preparations such as acetylcellulose phthalate or hydroxypropylmethylcellulose phthalate. Coloring substances or pigments can be added to the tablets or dragee coatings, for example for the purpose of identification or for indicating different doses of active substance.

Other orally administrable pharmaceutical compositions are dry-filled capsules made of gelatin and also soft, sealed capsules made of gelatin and a plasticizer such as glycerol or sorbitol. The dry-filled capsules may contain the active ingredient in the form of a granulate, for example, in admixture with fillers such as corn starch, binders and/or glidants such as talc or magnesium stearate and optionally stabilizers. In soft capsules, the active ingredient is preferably dissolved or suspended in suitable liquids or wax-like substances such as fatty oils, paraffin oil or polyethylene glycols, it being possible also for stabilizers to be added.

Other forms of oral administration are, for example, syrups prepared in a customary manner that contain the active ingredient in, for example, suspended form in a concentration that provides a suitable single dose when administered.

Further suitable dosage forms for parenteral administration are sterile aqueous solutions of an active ingredient in water-soluble form, for example, a water-soluble salt, or sterile aqueous injection suspensions which contain substances increasing the viscosity, for example, sodium, carboxymethyl cellulose, sorbitol and/or dextran, and optionally stabilizers. In addition, the active ingredient, with or without adjuvants, can also be in lyophilized form and brought into solution prior to parenteral administration by the addition of suitable solvents.

The invention also relates to a method of treatment of pathological conditions in a mammal, especially human, which as has been described hereinabove, which method comprises administering, a therapeutically effective amount of a compound of the formula I or of a pharmaceutically acceptable salt thereof.

DETAILED DESCRIPTION OF THE RADIOLIGAND INVENTION

The present invention relates to radioligands selective for sigma-1 receptors (σ-1 receptors) compounds useful as sigma receptors of the following formula III':

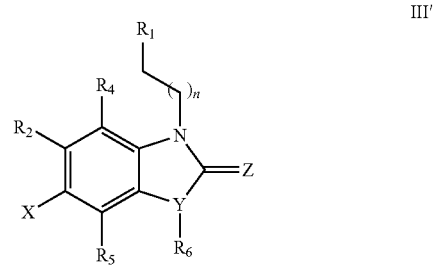

III'

Wherein $R_1$ can be an optionally substituted nitrogen-containing heterocycle radical, such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,4,5,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be S, Z can be either H, O, S, S—R or NR. R groups can be either H, aryls, alkyls, or cycloalkyls, "n" can be 1 to 5 carbons in length and stereoisomers, analogs, and pharmaceutically acceptable salts thereof as well as compositions comprising said compounds. The moiety bridging $R_1$ and N in the formula II can be a substituted $C_1$-$C_6$ alkylene, $C_1$-$C_6$ alkenylene wherein the alkylene group can have inserted into its chain a $C_3$-$C_5$ cycloalkyl group, aromatic, and heterocyclic group and wherein X is $C_1$-$C_4$ radiohaloalkyl.

The present invention relates to a still yet further series of compounds useful as sigma receptors of the following formula IV':

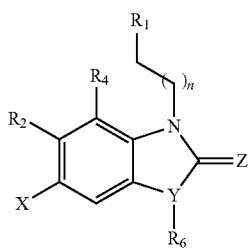

Wherein $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,4,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y is S. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula IV can be a substituted $C_1$-$C_6$ alkylene having the formula —(CHRx-(CH$_2$)—CH$_2$)— wherein the —CHRx-moiety is attached to $R_1$ and the alkylene group can have inserted into its chain a $C_3$-$C_5$ cycloalkyl group, aromatic, and heterocyclic group and wherein the Rx is a $C_1$-$C_5$ straight chain or branched chain alkyl or a $C_1$-$C_4$ straight chain or branched chain haloalkyl; X is $C_1$-$C_4$ radiohaloalkyl.

Additionally the present invention further comprises a method of preparing a compound according to formulas III', IV', V', VI', VII', XII' or XIII' comprising radio-halogenating a compound according to formulas III', IV', V', VI', VII', XII' or XIII' wherein X is an alkyl tosylate in the presence of a polar aprotic solvent.

The present invention further relates to compounds useful as sigma receptors of the following formula V':

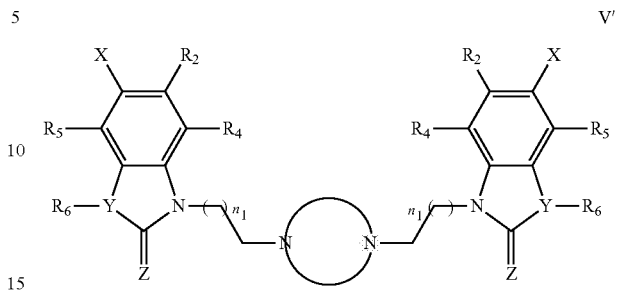

Wherein $R_{2,4,5,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y is S. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The $R_1$ bridging moiety in the formula V can be an optionally substituted $C_1$-$C_6$ alkylene, $C_1$-$C_6$ alkenylene or $C_1$-$C_6$ alkynylene group wherein the alkylene group can have inserted into its chain a $C_3$-$C_5$ cycloalkyl group, aromatic, and heterocyclic group. X is $C_1$-$C_4$ radiohaloalkyl.

DETAILED DESCRIPTION

Synthesis and In Vitro Binding of CM304

The cold ligand was prepared according to Scheme 6. Compounds 10 and 11 were synthesized using known procedures.[50] The fluoro compound was then successfully prepared from 11 via a halogen exchange using t-butylammonium fluoride and potassium fluoride. The fluorinated intermediate 12 was finally alkylated with 2-(hexamethyleneimino)ethylchloride in the presence of potassium carbonate in DMF to give 3-(2-(azepan-1-yl)ethyl)-6-(3-fluoropropyl)benzo[d]thiazol-2(3H)-one (13, CM304).

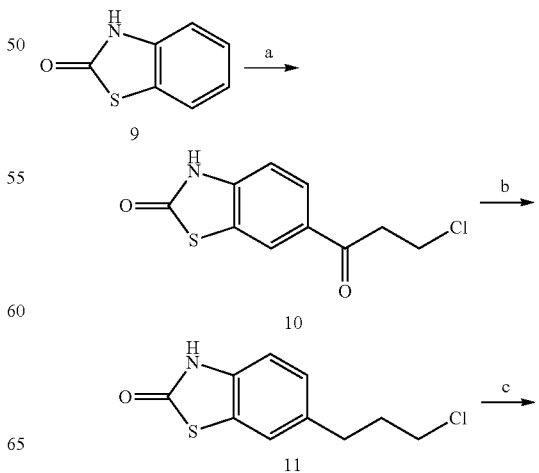

-continued

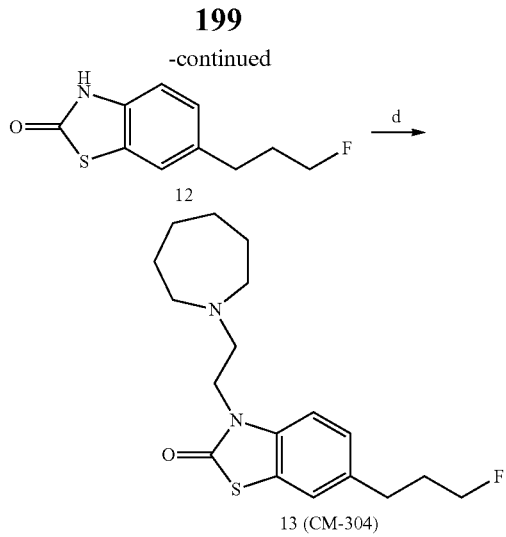

Scheme 6. Reagents and conditions: (a) 3-Chloropropionyl chloride, AlCl$_3$, DMF, 85° C.; (b) Et$_3$SiH, CF$_3$COOH, rt; (c) KF, TBAF, reflux; (d) 2-(hexamethyleneimino)ethylchloride, K$_2$CO$_3$, DMF, 55° C.

The experimental pKa (10.4) of CM304 was determined to be slightly higher than the calculated pKa value (9.36) while the experimental Log P O/W±SD–0.15±0.05 was significantly lower than the calculated Log P value (5.02). The experimental Log D PBS, pH 7.4±SD was measured to be 1.45±0.04 (n=6). CM304 was subjected to radioligand binding assays, as previously described,[50] and found to demonstrate high affinity (Ki=2.5 pM) and superior selectivity for σ-1 receptors (>145.000-fold selectivity for sigma-1 compared to sigma-2 receptors). Moreover, in a NovaScreen and in-house profile of 59 targets, CM304 displayed >100.000-fold selectivity for σ-1 receptor compared to other tested targets. CM304 exhibited >50% displacement of the radioligand at a 10,000 nM screening concentration and <20% displacement at a 100 nM screening concentration for nine targets, including: σ2-adrenoceptors; histamine H2 receptors; muscarinic M2 receptors; peripheral muscarinic receptors; neuronal (α-bungarotoxin insensitive) nicotinic receptors; nor epinephrine transporters; calcium L type channels; sodium, site 2 channels; acetylcholine esterase, suggesting it had 10,000-fold greater selectivity for sigma-1 compared to these targets.

Radiochemistry

The design strategy for generating [$^{18}$F]FTC-146 involved the preparation of a tosylate precursor 17 and its subsequent radiolabeling with fluorine-18 (Scheme 2). Compound II was reacted with benzoic acid to give 14 which was then alkylated with 2-(hexamethyleneimino) ethylchloride. Hydrolysis of the intermediate 15 yielded the corresponding alcohol 16. The tosylate precursor was then prepared by reacting the alcohol with p-toluenesulfonyl chloride in the presence of triethylamine. [$^{18}$F]FTC-146 was successfully synthesized via nucleophilic substitution using an automated GE TRACERlab FX-FN radiosynthesis module. Fluorine-18 (half life=109.8 min) radiolabeling was accomplished by reaction of tosylate precursor (17) with cyclotron-produced $^{18}$F-fluoride as an $^{18}$F-labeled Kryptofix-222/K$^+$/[$^{18}$F]F$^-$ complex in dimethylsulfoxide at 150° C. for 15 min. Semi-preparative reverse-phase HPLC of the crude reaction mixture afforded [$^{18}$F]FTC-146 in 3.7±1.9% yield (n=13) at end of bombardment (EOB), in >99% radiochemical purity (RCP), with a specific activity (SA) of 3.9±1.9 Ci/μmol (EOB) in a total synthesis time of 75 min. The formulated version of [$^{18}$F]FTC-146 in saline/ethanol (9:1, total 10 mL) was shown to be stable for at least 5.5 hours via analytical reverse-phase HPLC.

Cell Uptake Studies

Figure 15:
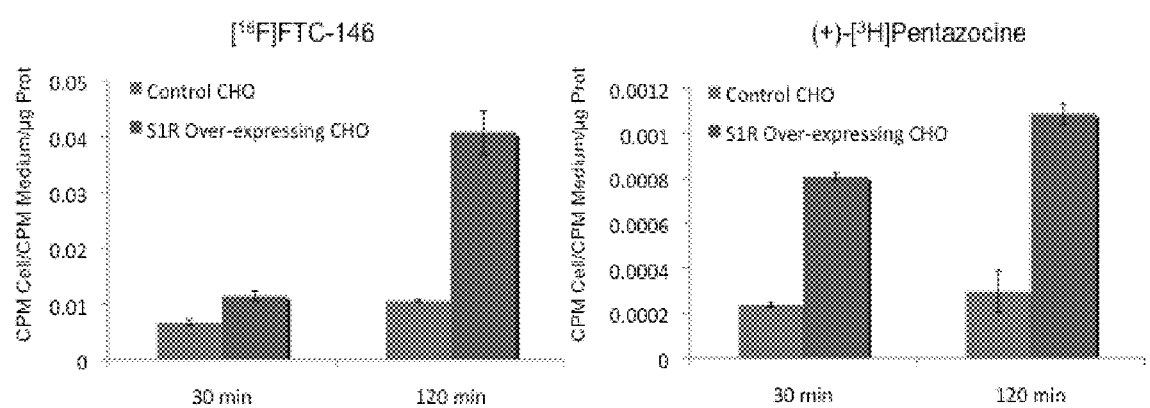
FIG. 15—[¹⁸F]FTC-146 uptake in CHO cells. Uptake of either [¹⁸F]FTC-146 (left) or (+)-[³H]pentazocine (right) in control CHO cells and CHO cells transfected with sigma-1 receptor (σ-1 receptor) cDNA following incubation for either 30 or 120 minutes. Results are expressed as counts per minute (CPM) recorded in a sample from a particular well/CPM recorded in medium/amount of protein (μg) present in a sample from that well.
Figure 16:
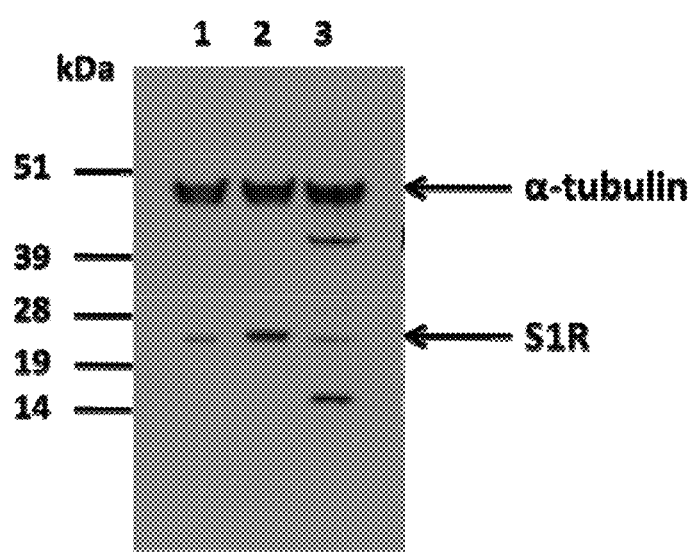
FIG. 16—Western blot analysis of σ-1 receptor expression in CHO cells. Western blot analysis of Sigma-1 receptor (σ-1 receptor) expression in control CHO cells, CHO cells transfected with σ-1 receptor cDNA, and a positive control cell line (JAR cells) known to contain σ-1 receptor protein. Cell lysates (50 ug of protein) were subjected to gel electrophoresis followed by immunoblot analysis with σ-1 receptor specific antibody S-18 (400:1). Lane 1: control CHO cells (transfected with empty σ-1 receptor vector); lane 2: CHO cells over-expressing σ-1 receptor (transfected with vector containing σ-1 receptor cDNA); and lane 3: positive control cell lysate for σ-1 receptor as su lied b Santa Cruz Biotech JAR cells Blot was also stained for σ-tubulin as a protein loading control.

Uptake of [$^{18}$F]FTC-146 in Chinese hamster ovarian (CHO) cells was compared to the uptake of the known σ-1 receptor ligand (+)-[$^3$H] pentazocine. Control CHO cells (transfected with a vector not containing the σ-1 receptor gene—to serve as a negative control) and CHO cells transfected with a vector containing σ-1 receptor cDNA (to serve as a positive control for σ-1 receptor expression in cells) were used for the uptake assays. Cells were exposed to [$^{18}$F]FTC-146 or (+)-[$^3$H] pentazocine for 30 and 120 min (triplicate for each time point). The incubated cells were subsequently washed, lysed and counted for radioactivity. All collected data were normalized for amount of protein present in each well. Data for both uptake assays (FIG. 15) showed there was a small increase in uptake for both radioligands between 30 and 120 min in control CHO cells. This increase was more pronounced in CHO cells transfected with σ-1 receptor cDNA, and numerically higher at both 30 and 120 min compared with negative control CHO cells. The uptake of [$^{18}$F]FTC-146 in cells transfected with σ-1 receptor cDNA was 4-fold higher than uptake in control CHO cells at 120 min. This difference was 3.6-fold for (+)-[$^3$H] pentazocine uptake studies (FIG. 16).

Western Blot

Figure 2:
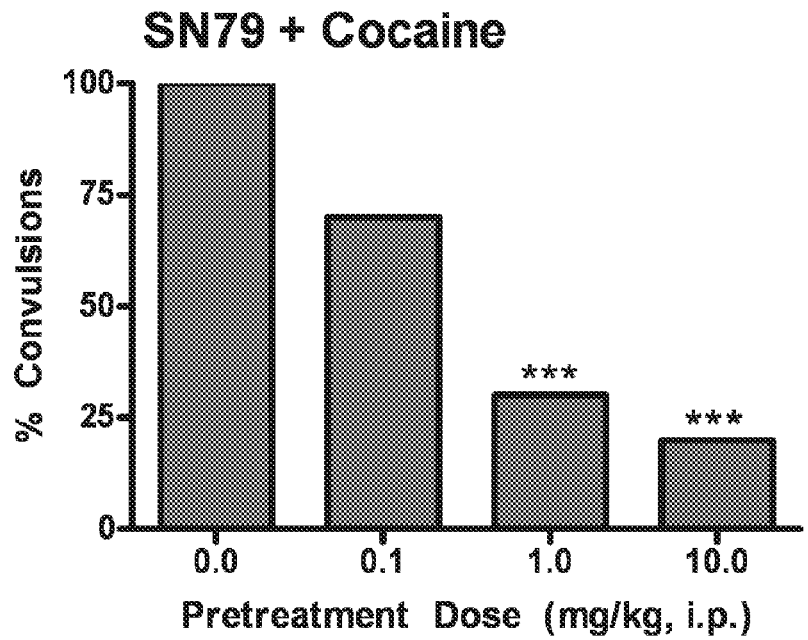
FIG. 2—SN79 attenuates the convulsive effects of cocaine (***P<0.005)
Figure 3:
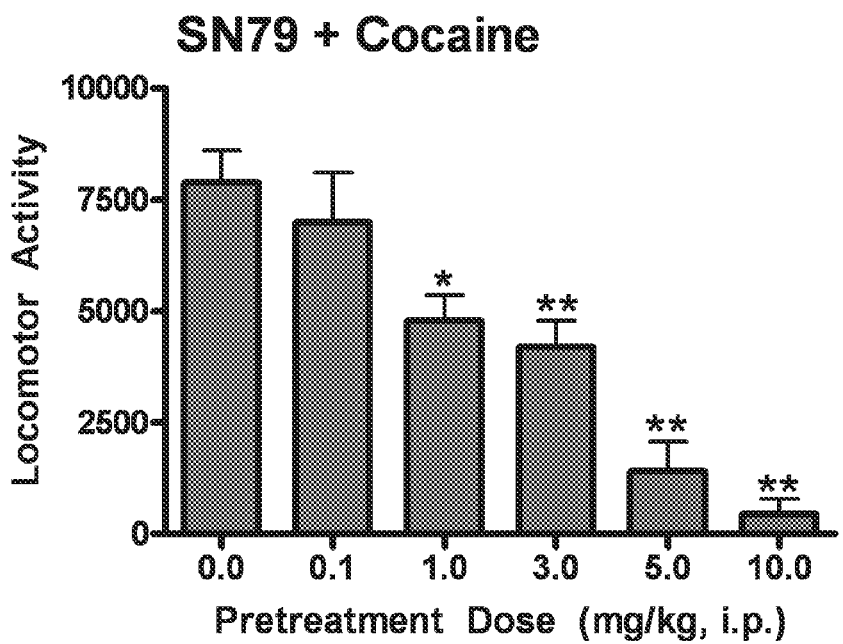
FIG. 3—SN79 pretreatment attenuates cocaine-induced locomotor activity (*P<0.05, **P<0.01)
Figure 4:
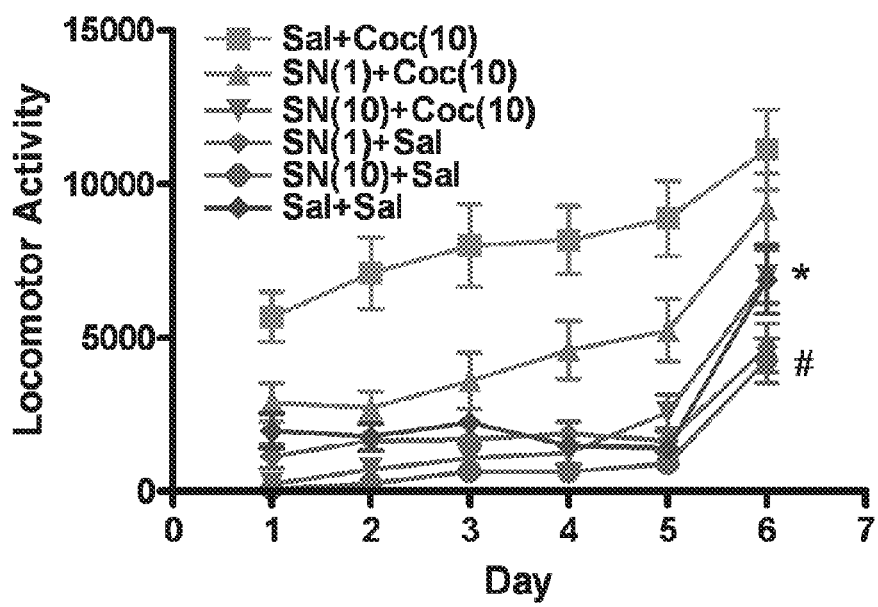
FIG. 4—SN79 pretreatment attenuates the development of cocaine-induced sensitization (*P<0.05, #P<0.05)

Western blot analysis was performed using the computer program Image J (image processing and analysis software in java) and showed that the level of σ-1 receptor expression in the CHO cells transfected with the σ-1 receptor cDNA was approximately 4.3 times greater than that found in the control CHO cells that had been transfected with an empty vector (FIG. 3).

In Vitro Metabolite Studies in Mouse Serum

The percentage of intact [$^{18}$F]FTC-146 in mouse serum was assessed over time via HPLC. It was found that the percentage of intact [$^{18}$F]FTC-146 remained at 100% throughout the entire time course of the study (5-120 min).

PET Imaging in Mice

The in vivo kinetics of [$^{18}$F]FTC-146 in normal mice were assessed using small animal PET. Dynamic brain PET scanning was commenced one minute prior to administration of [$^{18}$F]FTC-146 and terminated 62 minutes later. FIG. 17 shows the same coronal and sagittal PET slices from one of the baseline mouse studies summed over 0-5 minutes, 20-25 minutes and 52-62 minutes. These images provide visual evidence that [$^{18}$F]FTC-146 rapidly crossed the blood brain barrier and began to slowly wash out over the course of the imaging study. There was also accumulation in the snout and spine that increased over time.

Figure 5:
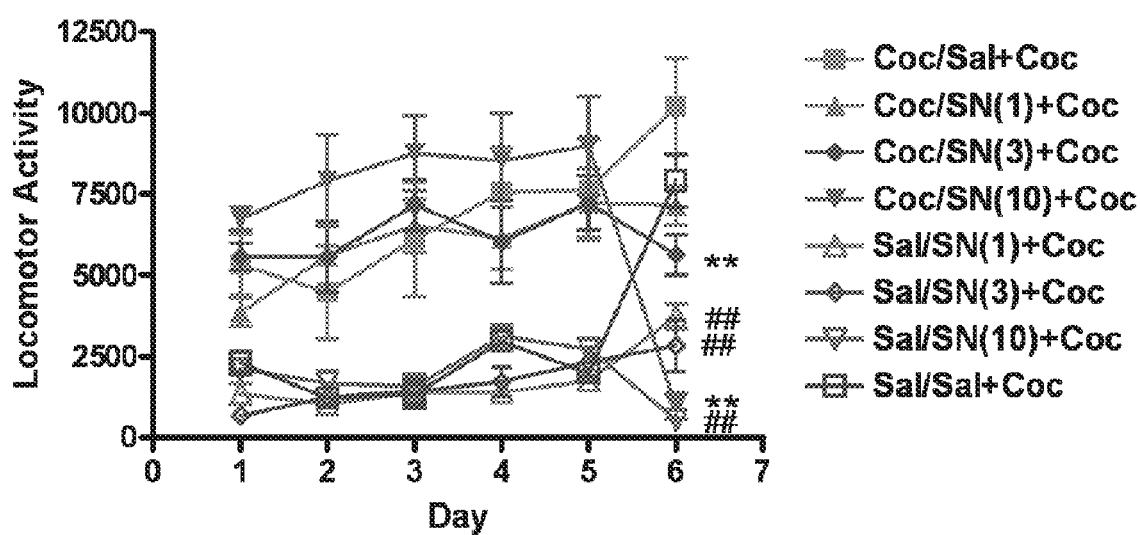
FIG. 5—SN79 pretreatment attenuates the expression of cocaine-induced sensitization (**P<0.05 vs sensitized, ##P<0.05 vs acute cocaine)

Graphs depicting uptake of [$^{18}$F]FTC-146 in whole mouse brain as a function of time for baseline and blocking studies are displayed in FIG. 5. The baseline time activity curve (TAC) (FIG. 18) demonstrated that [$^{18}$F]FTC-146 entered the brain rapidly, peaked within the first few minutes and then gradually decreased over the remaining time of the scan; however, it did not completely wash out of the brain over the duration of scanning Pre-treatment with CM304 (1 mg/kg) 10 minutes prior to radioligand administration reduced the binding of [$^{18}$F]FTC-146 in the brain at 60 min by 83% (FIG. 18).

In Vitro Half-Life Studies in Mouse and Rat Liver Microsomes

The metabolic stability of CM304 was evaluated in mouse and rat liver microsomes. First, CM304 was incubated in the presence of an NADPH-generating system at 37° C. for 60 min in test tubes. The reaction was initiated by adding cofactors and quenched at designated time points (0, 5, 10, 15, 30, 45, 60 min) by addition of an equal volume of ice-cold acetonitrile (ACN). CM304 was found to have a half-life of 4.2 min with a clearance of 0.55 mL/min/g in mouse and a half-life of 12.6 minutes with a clearance of 0.18 mL/min/g in rat.

Pharmacological Challenge in Mice

CM304 was evaluated for its ability to inhibit/attenuate cocaine-induced convulsions (associated with cocaine overdose) by pre-treating normal mice with either saline or CM304 (0.001, 0.01, 0.1, 1.0 or 10 mg/kg i.p.) 15 minutes prior to administering cocaine (70 mg/kg, i.p.). Subjects were continuously monitored for the onset of convulsions up to 30 min following administration of cocaine. Fisher's exact tests indicated that the following doses of CM304 significantly attenuated cocaine-induced convulsions: 0.001 mg/kg (p<0.005), 0.01 mg/kg (p<0.005), 0.1 mg/kg (p<0.05), 1 mg/kg (p<0.05), 10 mg/kg (p<0.005).

The present invention further comprises a method of differentiating between sigma-1 and sigma-2 receptors in a subject comprising using PET and an imaging agent wherein the imaging agent comprises at least one sigma 1 receptor ligand according to formulas III', IV', V', VI', VII', XII' or XIII'.

Since σ-1 receptors are intimately associated with numerous human cancers, neurodegenerative diseases, and psychiatric conditions, 10 radioligands specific for σ-1 receptors have the potential to serve as novel diagnostic tools and may be useful in assessing treatment effectiveness. The present study describes the synthesis and radiolabeling of a new σ-1 receptor PET radioligand together with its preliminary in vitro and in vivo characterization using cell uptake studies, metabolic stability tests and PET imaging of mice.

CM304 (13) was successfully synthesized (Scheme 6) and found to demonstrate high affinity (Ki=2.5 pM) and superior selectivity for σ-1 receptors (>145,000-fold selectivity for σ-1 receptors compared to σ-2 receptors) when compared to its parent, SN56. These results demonstrated that the small structural modification made to SN56 in order to form CM304 led to an improvement in affinity and selectivity for σ-1 receptors. In fact, both the affinity and selectivity of CM304 are higher than values reported for other known σ-1 receptor ligands reported in. The results from the NovaScreen profile further confirm the ultra selective nature of CM304.

Radiosynthesis of [$^{18}$F]FTC-146 was achieved by nucleophilic aliphatic radiofluorination of compound 17 (Scheme 7). In this type of reaction the use of a polar aprotic solvent is mandatory in order to take advantage of the nucleophilicity of the $^{18}$F anion. In addition, factors such as precursor concentration, reaction temperature and time can be crucial in influencing the final radiochemical yield (RCY), and thus need to be considered. In the present study, DMSO (a commonly used solvent in this type of labeling reactions) was chosen as the polar aprotic solvent. Since heating the reaction (precursor concentration 1 mg/mL) at 150° C. for 15 minutes afforded high purity product in sufficient yields/quantities (2-5%, 1-5 mCi/mL) for preliminary in vitro and in vivo investigations no further optimizations were pursued at this stage.

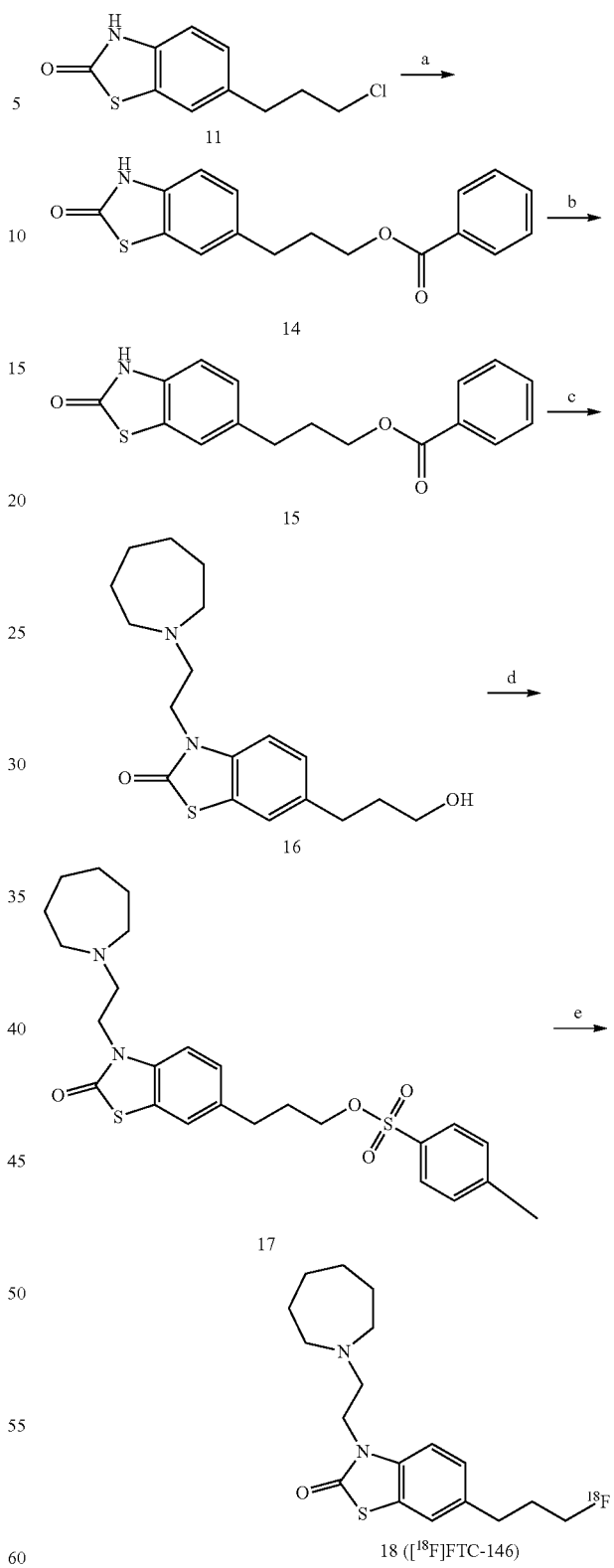

Scheme 7. Reagents and conditions: (a) Benzoic acid, K$_2$CO$_3$, DMF, 110° C.; (b) (2-(hexamethyleneimino)ethyl-chloride, K$_2$CO$_3$, DMF, 65° C.; (c) NaOH, H$_2$O, MeOH, reflux; (d) p-toluenesulfonyl chloride, Et$_3$N, DCM, rt; (e) Kryptofix-222/K$^+$/[$^{18}$F]F$^-$, DMSO, 150° C.

It is typical to differentiate between sigma-1 and sigma-2 receptors using benzomorphan-type opiates such as the well known selective σ-1 receptor ligand [$^3$H](+)-pentazocine.[51] For this reason we selected [$^3$H](+)-pentazocine as the "gold standard" σ-1 receptor ligand to compare with our new σ-1 receptor ligand [$^{18}$F]FTC-146 in cell uptake studies using transfected CHO cells. Results obtained from our cell uptake studies demonstrated the ability of [$^{18}$F]FTC-146 to bind σ-1 receptors in CHO cells in a comparable fashion to that of [$^3$H] (+)-pentazocine. The small increase in [$^{18}$F]FTC-146 and [$^3$H](+)-pentazocine uptake in control CHO cells between 30 and 120 minutes (FIG. 15) is supported by the Western blot results (FIG. 16) which confirmed the presence of low levels of σ-1 receptor in CHO cells prior to introducing σ-1 receptor cDNA. Uptake of [$^{18}$F]FTC-146 in CHO cells transfected with σ-1 receptor cDNA compared to control CHO cells at 120 min (FIG. 15) was 4-fold higher. This was comparable to the 3.6 fold greater uptake of [$^3$H](+)-pentazocine in CHO cells transfected with σ-1 receptor cDNA compared to control CHO cells at 120 min, indicating that [$^{18}$F]FTC-146 behaves similarly to [$^3$H](+)-pentazocine and that it may be a more sensitive marker of σ-1 receptor levels. Western blot results verified the level of [$^{18}$F]FTC-146 uptake in cell assays (at 120 min) correlated to the level of σ-1 receptor protein levels and therefore highlight its potential as a radioligand for accurately identifying and visualizing σ-1 receptors.

Through stability studies in mouse serum we found that [$^{18}$F]FTC-146 remained 100% intact over a 120 minute period. This demonstrated that [$^{18}$F]FTC-146 was stable in mouse serum in vitro, and although did not account for the possibility of liver metabolism, implied that it should be stable in mice in vivo.

Following these encouraging in vitro cell uptake and serum stability results, the in vivo kinetics and binding of this radio fluorinated ligand were evaluated in living, normal mice using small animal PET. The brain of each mouse was positioned in the center field of view (FOV) for each study as σ-1 receptors are known to be abundantly present in various parts of the brain[7] (predominantly in cortical regions, thalamus, striatum and cerebellum),[43] and thus was thought to be a suitable region of interest for evaluating the kinetics and binding profile of our new radioligand.

PET images of [$^{18}$F]FTC-146 in anaesthetized mice show high uptake of the radioligand in brain and also spine (FIG. 17). Baseline TACs (FIG. 18) showed that [$^{18}$F]FTC-146 rapidly crossed the blood brain barrier (BBB), reaching a maximum uptake of ~17% ID/g within the first few minutes, followed by a slow decline in uptake levels throughout the remainder of the scan to a level of 6% ID/g at 60 min. Pre-treating mice with CM304 (1 mg/kg) 10 minutes prior to radioligand administration led to a marked reduction of [$^{18}$F]FTC-146 binding in the brain (83% reduction at 60 min) (FIG. 5). These results indicated that [$^{18}$F]FTC-146 accumulation in mouse brain most likely represents specific σ-1 receptor binding. The initial spike in radioligand uptake shown in the blocking TAC data is typical of blocking studies and is due to the unlabeled compound (in this case CM304) occupying the peripheral σ-1 receptor sites thus creating a situation whereby an additional bolus of the radioligand from the periphery is available to cross the BBB, only to discover it has no free receptors to bind to, and subsequently washes out of the brain in a rapid manner.

Although [$^{18}$F]FTC-146 is yet to be evaluated alongside other fluorinated σ-1 receptor radioligands, its initial kinetics (i.e., rapid uptake in mouse brain within the first few minutes) appear similar to that reported for [$^{18}$F]FM-SA4503 and [$^{18}$F]fluspidine in normal mice.[44, 49] However the binding profile of [$^{18}$F]FTC-146 in mouse brain at later time points is quite different from the reported uptake levels for other known σ-1 receptor radioligands at corresponding times. For example [$^{18}$F]FTC-146 reached its maximum uptake in mouse brain within the first few minutes of imaging and then gradually began to wash out of the brain to a level 65% of its maximum at 60 minutes post injection, whereas [$^{18}$F]FM-SA4503 and reached its maximum uptake in the brain at 30 minutes post injection and did not experience significant washout over the remainder of the study (120 minutes post injection). Biodistribution studies with [$^{18}$F]fluspidine demonstrated that it reached maximum uptake in the mouse brain at 30 minutes post injection and then washed out to a level 81% of its maximum at 60 minutes post injection. Uptake levels of [$^{18}$F]SFE and [$^{18}$F]FPS in living mice have not been reported in the literature and thus we were unable to visually compare the kinetics of [$^{18}$F]FTC-146 with them at present, however the fact that [$^{18}$F]FTC-146 displayed relatively fast in vivo binding kinetics suggests it might not have the same irreversible binding problems as [$^{18}$F]FM-SA4503 and [$^{18}$F]SFE.

Although there was some observed bone uptake in the mouse [$^{18}$F]CM304 PET studies (likely due to defluorination), bone uptake has also been reported in studies using [$^{18}$F]FM-SA4503[44] and [$^{18}$F] fluspidine,[49] the former of which was postulated to be due to high levels of σ-1 receptors in highly proliferative tissues (e.g. bone marrow), and the latter of which was shown through biodistribution studies to be present in both mouse bone and bone marrow.

Currently there are no suitable treatments for cocaine overdose and none of the routinely used anti-convulsants are capable of attenuating cocaine-induced seizures. Since it has been shown that σ-1 receptor antagonists can block the affects of cocaine,[33] we evaluated our non-radioactive compound, CM304, for its ability to prevent cocaine-induced convulsions. In vivo cocaine studies were pursued with male, Swiss Webster mice. The pretreated animals were cocaine-challenged (70 mg/kg, i.p.) 15 min after intraperotineal administration of saline or CM304 (0.001 mg/kg-10 mg/kg). The subjects were continuously monitored for the next 30 min for the onset of convulsions. Similar to other putative σ-1 receptors antagonists, CM304 significantly attenuated cocaine-induced convulsions at all doses examined ($P<0.05$, data not shown). This data is consistent with other reported sigma-1 antagonists.

In conclusion, applicants successfully prepared a new, ultra selective $^{18}$F-labeled σ-1 receptor ligand, [$^{18}$F]FTC-146 that demonstrates specific binding to σ-1 receptors in cells and mice making it a promising new candidate for visualizing σ-1 receptors in living subjects. The unlabeled compound, CM304 might also be useful in treating cocaine overdose.

Experimental Section

General

For the reported radiochemistry, semi-preparative HPLC separations were performed on Dionex 680 pump with KANUR UV detector K-2001 (for purification of [$^{18}$F]FTC-146). Analytical HPLC was performed on Lab Alliance with Model 500 UV detector. Radioactivity in HPLC eluates was detected with a model 1055 single-channel radiation detector (Carroll & Ramsey Associates). (+)-[$^3$H]Pentazocine was purchased from NEN Life Science Products (Boston, Mass.). If not otherwise stated, chemicals were purchased from commercial sources and were used without further purification. All PET imaging was performed on a microPET R4 model scanner (Siemens) fitted with a computer-controlled bed, 10.8 cm transaxial and 8 cm axial field of view (FOV), no septa and operated exclusively in 3-dimensional list mode. MicroPET images were reconstructed with 2-dimensional OSEM (Ordered Subsets Expectation Maximization) and analyzed using AMIDE (A Medical Image Data Examiner) software.[52] For metabolite studies an Agilent 1200 HPLC system with autosampler and Gabi radioactivity detector (Raytest) was used.

The UPLC system, consisted of Water's Acquity UPLC (Milford, Mass., USA) equipped with a binary solvent manager, vacuum degasser, thermostatted column compartment, and an autosampler. Chromatographic separations were performed on a Waters Acquity UPLC™ BEH C18 column (1.7 µm, 2.1×50 mm). For the metabolism studies an isocratic method was developed using the mobile phase consisted of 0.1% formic acid in water: 0.1% formic acid in methanol (50:50, v/v). For the metabolite separation, a linear gradient method was developed with a mobile phase containing 0.1% formic acid in water (A) and 0.1% formic acid in ACN (B). The linear gradient elution program was as follows: 0-80% B over 6 min, followed by an isocratic hold at 80% B for another 4 min. At 10 min, B was returned to 0% in 2 min and the column was equilibrated for 3 min before the next injection. The total run time for each injection was 15 min. The flow rate was 0.2 mL/min. The column temperature was maintained at 25° C. and the injection volume was 10 µL.

The mass spectrophotometer consisted of a Waters Micromass Quattro Micro™ triple-quadrupole system (Manchester, UK). The system was controlled by MassLynx software version 4.0. Ionization was performed in the positive electrospray mode. The MS/MS parameters for the analysis were as follows: capillary voltage 4.95 kV, cone voltage 31V, extractor voltage 5V, RF lens voltage 0.5V. The source and desolvation temperatures were 110° C. and 400° C., respectively, and the desolvation and cone gas flows were 252 and 76 L/hr, respectively. The selected mass-to-charge (m/z) ratio transition of CM304 ion [M+H]+ used in the single ion recording (SIR) was m/z 337.03 The dwell time was set at 500 ms.

Animals

All experimental procedures involving animals were performed under humane conditions following approval from the Stanford University or University of Mississippi animal research internal review board. Animals had access to food and $H_2O$ ad libitum and were kept under a 12 h light/dark cycle.

Materials. Reagents and starting materials were obtained from commercial suppliers and were used without purification. Precoated silica gel GF Uniplates from Analtech were used for thin-layer chromatography (TLC). Column chromatography was performed on silica gel 60 (Sorbent Technologies). $^1H$ and $^{13}C$ NMR spectra were obtained on a Bruker APX400 at 400 and 100 MHz, respectively. The high resolution mass spectra (HRMS) were recorded on a Waters Micromass Q-Tof Micro mass spectrometer with a lock spray source. The mass spectra (MS) were recorded on a WATERS ACQUITY Ultra Performance LC with ZQ detector in ESI mode. Chemical names were generated using ChemDraw Ultra (CambridgeSoft, version 10.0). The calculated pKa and log P were determined using PALLAS 3.1.2.4 Software from CompuDrug Chemistry, Ltd (Sedona, Ariz. USA).

6-(3-chloropropanoyl)benzo[d]thiazol-2(3H)-one (10). Dimethylformamide (8.6 mL, 115 mmol) was slowly added to aluminum chloride (53.3 g, 400 mmol) under vigorous stirring. After 15 min. of stirring, 2-hydroxybenzothiazole (6.04 g, 40 mmol) was added, and the mixture was brought to 45° C. After 15 min, 3-chloropropionyl chloride (5.8 mL, 60 mmol) was added and the reaction mixture was heated at 85° C. for 3 h. The hot mixture was then carefully poured onto ice, and the crude product was collected by filtration. The solid was dissolved in ethyl acetate and water was added. The layers were then separated and, the organic layer was washed with brine and dried. The solvent was removed in vacuo, and the residue was recrystallized from toluene/dioxane to give 5.15 g (54%) of 6-(3-chloropropanoyl)benzo[d]thiazol-2(3H)-one as a orange solid. $^1H$ NMR (DMSO-d6): δ 12.26 (br s, 1H), 8.24 (d, J=1.4 Hz, 1H), 7.90 (dd, J=8.4, 1.7 Hz, 1H), 7.19 (d, J=8.4 Hz, 1H), 3.91 (t, J=6.4 Hz, 2H), 3.50 (d, J=6.3 Hz, 2H). $^{13}C$ NMR (DMSO-d6): δ 195.07, 170.37, 140.49, 130.94, 126.89, 123.77, 123.25, 111.19, 40.38, 39.52. MS (EI) m/z 242 (M+−1).

6-(3-chloropropyl)benzo[d]thiazol-2(3H)-one (11). Triethylsilane (4.2 mL, 26 mmol) was added to a stirred solution of 10 (2.73 g, 11.3 mmol) in trifluoroacetic acid (15 mL) and the reaction mixture was stirred for 4 h at room temperature. The solvent was removed in vacuo, and the residue was purified by chromatography on a silica gel column using a gradient of petroleum ether/ether (7:3 to 5:5) as the eluent and recrystallized from toluene/hexanes to give 3 g (72%) of 6-(3-chloropropyl)benzo[d]thiazol-2(3H)-one as a white solid. $^1H$ NMR (DMSO-d6): δ 11.76 (br s, 1H), 7.38 (s, 1H), 7.10 (d, J=8.0 Hz, 1H), 7.03 (d, J=8.0 Hz, 1H), 3.59 (t, J=6.4 Hz, 2H), 2.68 (t, J=7.4 Hz, 2H), 1.99 (qu, J=7.2 Hz, 2H). $^{13}C$ NMR (DMSO-d6): δ 169.89, 135.12, 134.45, 126.53, 123.40, 122.13, 111.31, 44.52, 33.75, 31.79. MS (EI) m/z 226 (M+−1).

6-(3-fluoropropyl)benzo[d]thiazol-2(3H)-one (12). A mixture of 11 (0.3 g, 1.32 mmoles), KF (0.23 g, 3.95 mmoles) and TBAF (1M in THF, 3.95 mL, 3.95 mmoles) in THF (10 mL) was heated at reflux for 4 h. After completion of the reaction, the reaction mixture was partitioned between ethyl acetate and water, and the organic layer was washed with brine and dried. The solvent was removed in vacuo, and the residue was purified by chromatography on a silica gel column using petroleum ether/ether (8:2) as the eluent to give 0.096 g (35%) of 6-(3-fluoropropyl)benzo[d]thiazol-2(3H)-one as a white solid. $^1H$ NMR (CDCl$_3$): δ 10.33 (br s, 1H), 7.23 (s, 1H), 7.10 (s, 2H), 4.45 (dt, J=47.2, 5.8 Hz, 2H), 2.76 (t, J=7.6 Hz, 2H), 2.00 (dquint, J=25.2, 6.8 Hz, 2H). $^{13}C$ NMR (CDCl$_3$): δ 173.26, 136.39, 133.69, 126.83, 124.09, 122.13, 111.79, 82.77 (d, J=164.2 Hz), 32.13 (d, J=19.7 Hz), 31.01 (d, J=5.2 Hz). MS (EI) m/z 210 (M+−1).

3-(2-(azepan-1-yl)ethyl)-6-(3-fluoropropyl)benzo[d]thiazol-2(3H)-one hydrochloride (13, CM304). $K_2CO_3$ (0.18 g, 1.28 mmol) and 2-(hexamethyleneimino)ethylchloride hydrochloride (0.08 g, 0.40 mmol) were added, under mechanical stirring, to a solution of 12 (0.09 g, 0.42 mmol) in anhydrous DMF (2 mL). The reaction mixture was heated at 55° C. for 2 h. After cooling, the mixture was poured into 10 mL of water, extracted with ethyl acetate (3×20 mL), washed with saturated aqueous NaCl and dried. The solvent was removed in vacuo, and the residue was purified by chromatography on a silica gel column using methylene chloride/methanol (9.5:0.5) as the eluent. 3-(2-(azepan-1-yl)ethyl)-6-(3-fluoropropyl)benzo[d]thiazol-2(3H)-one was isolated as a hydrochloride salt (white solid, 0.12 g, 80%) by addition of HCl/dioxane. $^1H$ NMR ($D_2O$): δ 7.34 (br s, 1H), 7.26-7.24 (m, 1H), 7.16-7.14 (m, 1H), 4.46 (dt, J=47.2, 4.5 Hz, 1H), 4.28 (t, J=4.8 Hz, 2H), 3.49-3.37 (m, 6H), 2.70-2.66 (m, 2H), 1.97-1.66 (m, 11H). $^{13}C$ NMR ($D_2O$): δ 173.02 (C=O), 137.92 (Cq), 133.68 (Cq), 127.31 (CHar), 122.67 (CHar), 122.09 (Cq), 110.90 (CHar), 84.33 (d, J=157.6 Hz, CH2), 55.23 (CH2), 53.46 (CH2), 37.47 (CH2), 31.34 (d, J=18.8 Hz, CH2), 30.30 (d, J=5.5 Hz, CH2), 25.61 (CH2), 23.37 (CH2). HRMS (EI) calcd for $C_{18}H_{26}N_2OFS$ [M+H]+ 337.1750. found 337.1764.

3-(2-oxo-2,3-dihydrobenzo[d]thiazol-6-yl)propyl benzoate (14). $K_2CO_3$ (5.31 g, 38.4 mmol) and benzoic acid (9.38 g, 76.8 mmol) were added, under mechanical stirring, to a solution of 11 (3.5 g, 15.4 mmol) in anhydrous DMF (250 mL). The reaction mixture was heated at 110° C. for 6 h. After cooling, the mixture was poured into 100 mL of a 2.5 N HCl solution in water, extracted with ethyl acetate (3×70 mL), and the organic phase was washed with brine. The solvent was dried and removed in vacuo and the residue was chromatographed on a silica gel column using a gradient of petroleum ether/ethyl ether (4:6 to 6:4) as the eluent. The product was then recrystallized in toluene to give 2.97 g (62%) of 3-(2-oxo-2,3-dihydrobenzo[d]thiazol-6-yl)propyl benzoate as a white solid. $^1$H NMR (DMSO-d6): δ 11.70 (br s, 1H), 7.91 (d, J=7.6 Hz, 2H), 7.63 (t, J=7.5 Hz, 1H), 7.49 (t, J=7.6 Hz, 2H), 7.41 (s, 1H), 7.12 (d, J=8.1 Hz, 1H), 7.02 (d, J=8.1 Hz, 1H), 4.25 (t, J=6.3 Hz, 2H), 2.71 (t, J=7.4 Hz, 2H), 2.03-1.97 (m, 2H). $^{13}$C NMR (DMSO-d6): δ 170.00, 165.70, 135.77, 134.42, 133.22, 129.76, 129.10, 128.64, 126.58, 123.44, 122.18, 111.34, 64.02, 31.34, 29.93. MS (EI) m/z 312 (M+−1).

3-(3-(2-(azepan-1-yl)ethyl)-2-oxo-2,3-dihydrobenzo[d]thiazol-6-yl)propyl benzoate (15). $K_2CO_3$ (0.75 g, 5.47 mmol) and 2-(hexamethyleneimino)ethylchloride hydrochloride (0.47 g, 2.37 mmol) were added, under mechanical stirring, to a solution of 14 (0.57 g, 1.82 mmol) in anhydrous DMF (10 mL). The reaction mixture was heated at 65° C. for 2 h. After cooling, the mixture was poured into 80 mL of water, extracted with ethyl acetate (3×60 mL), and the combined organic layers were washed with brine and dried. The solvent was removed in vacuo, and the residue was chromatographed on a silica gel column using diethyl ether as the eluent to give 0.72 g (90%) of 3-(3-(2-(azepan-1-yl)ethyl)-2-oxo-2,3-dihydrobenzo[d]thiazol-6-yl)propyl benzoate as a colorless oil. A sample was isolated as a hydrochloride salt for analysis. $^1$H NMR (DMSO-d6): δ 11.29 (br s, 1H), 7.92 (d, J=8.4 Hz, 2H), 7.66-7.57 (m, 3H), 7.50 (t, J=7.6 Hz, 2H), 7.28 (d, J=8.0 Hz, 1H), 4.43-4.40 (m, 2H), 4.27 (t, J=6.0 Hz, 2H), 3.44-3.18 (m, 6H), 2.77 (t, J=7.2 Hz, 2H), 2.06-1.56 (m, 10H). $^{13}$C NMR (DMSO-d6): δ 168.74 (CO), 165.52 (CO), 136.68 (Cq), 134.23 (Cq), 133.07 (CHar), 129.59 (Cq), 128.92 (CHar), 128.50 (CHar), 126.78 (CHar), 122.45 (CHar), 121.44 (Cq), 111.36 (CHar), 63.83 (CH2), 53.62 (CH2), 52.05 (CH2), 37.02 (CH2), 31.10 (CH2), 29.72 (CH2), 25.58 (CH2), 22.88 (CH2). HRMS (EI) calcd for $C_{25}H_{31}N_2O_3S$ [M+H]+ 439.2055. found 439.2056.

3-(2-(azepan-1-yl)ethyl)-6-(3-hydroxypropyl)benzo[d]thiazol-2(3H)-one (16). To a solution of 15 (0.67 g, 1.53 mmol) in methanol (10 mL) was added a solution of sodium hydroxide (0.15 g, 3.84 mmol) in water (10 mL). The mixture was heated at 90° C. for 1 h, concentrated in vacuo, poured into 1N HCl (20 mL) and extracted with ethyl acetate (10 mL). The pH of the aqueous layer was adjusted to 10 with potassium carbonate and the mixture was extracted with ethyl acetate (3×20 mL). The combined organic layers were washed with brine, dried and evaporated. The residue was chromatographed on a silica gel column using methylene chloride/methanol (9.7:0.3) as the eluent to give 0.47 g (92%) of 3-(2-(azepan-1-yl)ethyl)-6-(3-hydroxypropyl)benzo[d]thiazol-2(3H)-one as a white solid. A sample was isolated as a hydrochloride salt for analysis. $^1$H NMR (DMSO-d6): δ 11.35 (br s, 1H), 7.46 (d, J=1.2 Hz, 1H), 7.36 (d, J=8.4 Hz, 1H), 7.50 (dd, J=8.0, 1.2 Hz, 1H), 4.31 (t, J=6.8 Hz, 2H), 3.80 (br s, 2H), 3.53 (s, 1H), 3.39-3.29 (m, 6H), 2.60 (t, J=7.6 Hz, 2H), 1.79 (br s, 4H), 1.68 (qu, J=8.0 Hz, 2H), 1.58 (br s, 4H). $^{13}$C NMR (DMSO-d6): δ 170.04 (CO), 138.34 (Cq), 134.45 (Cq), 127.41 (CHar), 122.92 (CHar), 121.91 (Cq), 111.58 (CHar), 60.26 (CH2), 54.60 (CH2), 53.07 (CH2), 37.70 (CH2), 34.50 (CH2), 31.47 (CH2), 25.99 (CH2), 23.58 (CH2). HRMS (EI) calcd for $C_{28}H_{27}N_2O_2S$ [M+H]+ 335.1793. found 335.1786.

3-(3-(2-(azepan-1-yl)ethyl)-2-oxo-2,3-dihydrobenzo[d]thiazol-6-yl)propyl 4-methyl benzenesulfonate (17). A solution of p-toluenesulfonyl chloride (0.24 g, 1.26 mmol) in methylene chloride (10 mL) was slowly added to a solution of 16 (0.38 g, 1.15 mmol) and triethylamine (0.16 mL, 2.42 mmol) in methylene chloride (20 mL). The mixture was stirred for 3 days at room temperature and the solvent was evaporated. The residue was purified by chromatography on a silica gel column using a gradient of methylene chloride/methanol (10:0 to 9.7:0.3) as the eluent to give 0.5 g (89%) of 3-(3-(2-(azepan-1-yl)ethyl)-2-oxo-2,3-dihydrobenzo[d]thiazol-6-yl)propyl 4-methyl benzenesulfonate as a pale yellow oil. $^1$H NMR (DMSO-d6): δ 7.78 (d, J=8.4 Hz, 2H), 7.46 (d, J=8.4 Hz, 2H), 7.30 (s, 1H), 7.20 (d, J=8.4 Hz, 1H), 7.08 (d, J=8.0 Hz, 1H), 4.00-3.93 (m, 4H), 2.71 (t, J=6.8 Hz, 2H), 2.59-2.55 (m, 6H), 2.41 (s, 3H), 1.88-1.85 (m, 2H), 1.45 (br s, 8H). $^{13}$C NMR (DMSO-d6): δ 168.36, 144.68, 135.24, 135.11, 132.32, 129.98, 127.41, 126.45, 122.10, 121.25, 111.11, 69.77, 54.84, 54.21, 40.64, 30.13, 29.80, 27.93, 26.27, 20.95. MS (EI) m/z 489 (M++1).

Radiosynthesis of [$^{18}$F]FTC-146 (18). No carrier added-aqueous [$^{18}$F]fluoride ion was produced on a PETtrace cyclotron (GE Healthcare, Sweden) by irradiation of a 1.6 mL water target using a 16 MeV proton beam on 95% enriched [$^{18}$O]H$_2$O by the [$^{18}$O(p,n)18F] nuclear reaction. [$^{18}$F]Fluoride in [$^{18}$O]H$_2$O was transferred to a GE TRACERlab FX-FN synthesizer and passed through an anion exchange resin (QMA cartridge in carbonate form, prepared by washing with 1 mL EtOH and 1 mL of water) under vacuum. Trapped [$^{18}$F]fluoride ions were then eluted from the QMA cartridge and transferred to the reactor using an eluent solution containing 3.5 mg of $K_2CO_3$ and 15 mg of Kryptofix 222 (K222: 4,7,13,16,21,24-hexaoxa-1,10-diazabicyclo[8.8.8]hexacosan) in acetonitrile (0.9 mL) and water (0.1 mL) mixture. The solution was then evaporated at 65° C. under helium flow and vacuum, followed by heating at 88° C. under vacuum. Tosylate precursor 8, 3-(2-oxo-3-(2-(piperidin-1-yl)ethyl)-2,3-dihydrobenzo[d]thiazol-6-yl) propyl 4-methylbenzenesulfonate (1 mg) was dissolved in dimethylsulfoxide (0.5 mL) and added to the dry Kryptofix-222/K$^+$[$^{18}$F]F$^-$ complex. The mixture was allowed to react at 150° C. for 15 minutes. Upon completion, the reaction mixture was diluted with sterile water (8 mL) and passed through a C18 Sep-Pak cartridge. The C18-trapped-radiolabelled-product was then eluted from the C18 Sep-Pak with ACN (1.5 mL) and sterile water (1.5 mL). The resulting crude mixture was then injected onto two serial HPLC Phenomenex Gemini C-18, 5 μm (10×250 mm) semi-preparative reversed-phase column. Using a mobile phase of H$_2$O (0.1% TEA):ACN (0.1% TEA), (pH=8):(20/80, v:v), and with a flow rate of 5.0 mL/min, the retention time (tR) of [$^{18}$F]FTC-146 was 13 min. The radioactive fraction corresponding to [$^{18}$F]FTC-146 was collected in a round bottom flask containing sterile water (15 mL) and then passed through a C18 Sep-Pak. A further 10 mL of sterile water was passed through the C18 Sep-Pak. The trapped, purified radiolabelled product was eluted from the C18 Sep-Pak using ethanol (1 mL) and saline (9 mL). The formulated solution was then filtered through a sterile 13 mm Millipore GV 0.22 μm filter into a sterile pyrogen free evacuated 30 mL vial. Solutions in saline containing no more than 10% ethanol by volume were used for the studies described in this article.

Quality Control of [$^{18}$F]FTC-146

For determination of specific activity and radiochemical and chemical purity, an aliquot of the final solution of known volume and radioactivity was injected onto an analytical reversed-phase HPLC column (Phenomenex Gemini C18 5 μm (4.6×250 mm). A mobile phase of H$_2$O (0.1% TEA): ACN (0.1% TEA): (20:80; v:v) at a flow rate of 1.0 mL/min was used to elute [$^{18}$F]FTC-146 with a retention time (tR) of 8.33 min. The area of the UV absorbance peak measured at 254 nm corresponding to the carrier product was measured (integrated) on the HPLC chromatogram and compared to a standard curve relating mass to UV absorbance.

Determination of pKA for CM304

The pKa of CM304 was determined using the potentiometric titration method. A solution of 0.01M sodium hydroxide was prepared and the pH measured as 11.9. Similarly, 0.01M hydrochloric acid solution was prepared and the pH measured as 2.07. To 50 mL of a 1 mM CM304 solution, 0.1 mL volumes of sodium hydroxide were added and pH recorded (Mettler Toledo SevenEasy™ pH meter S20) until the pH of the solution became constant. To the same sample, 0.1 mL portions of hydrochloric acid were added and pH recorded until it became constant. A titration curve was then plotted as pH versus volume of base/acid added. The intersection point of these two curves was noted as the pKa value of CM304.

Determination of Partition Coefficient (Log P) for CM304

Using the Shake-flask method, 47 n-Octanol and water/PBS, pH 7.4 (equal quantity) were added to a glass vial (25 ml). The contents were sealed and stirred continuously for 24 h at 25° C. to achieve mutual saturation of the phases. Water/PBS, pH 7.4 phase was brought into a vessel together with a Teflon-coated magnetic stirring bar. The n-octanol phase containing the known quantity of test substance was poured very carefully on top of the aqueous phase in order to avoid emulsion formation as far as possible. The vessel was not shaken; instead the system was stirred for an extended period of time (at least 36 h) allowing equilibrium to be reached. The contents were allowed to separate on standing and then centrifuged. An aliquot of aqueous layer was taken and diluted (1000 times) for quantitative analysis by UPLC/MS/MS.

In Vitro Radioligand Binding Assays

Competition binding assays were performed as previously described. Briefly, radioligands were used to tag the targeted sites under standard conditions. CM304 was evaluated at a screening concentration of 10,000 nM. If <50% displacement was observed, then the results are reported as Ki>10,000 nM. For assays run by NovaScreen, a single additional screening concentration of CM304 was tested at 100 nM. For full competition binding assays which were run in-house, 10 concentrations of CM304 were tested to generated IC50 values, which were converted to Ki values using the Cheng Prusoff equation.

Cell Uptake Studies Using Transfected

Cells CHO cells were grown in Ham's F-12 medium. For uptake studies CHO cells were transfected using Lipofectamine 2000 (Invitrogen, Carlsbad, Calif., USA) and either pcDNA (empty vector, negative control) or σ-1 receptor gene (OPRS1, accession number NM_005866.2, OriGene, Rockville, Md., USA) following manufacturers directions. The cells were harvested and 2×105 cells were seeded per well in 24 well plates. Twenty-four hours later, CHO cells were transfected with either 0.8 μg pcDNA (empty vector, control), or 0.8 μg sigma-1 DNA. Media was refreshed 12 hours later. Twenty-four hours after initial transfection, Ham's F-12 medium was prepared containing enough [$^{18}$F]FTC-146 for 2 μCi per well. After 30 and 120 minutes uptake, medium from each of the triplicate wells was aspirated and cells were washed twice with cold PBS (500 μL). Following this, cells were lysed with 1 N NaOH (500 μL). A portion of each lysate (250 μL) was transferred to a glass tube and activity was measured with a Cobra II γ counter (Packard-Perkin Elmer, Waltham, Mass., USA). Protein content from each well was measured by Bradford assay. The same protocol was followed for (+)-[$^3$H]pentazocine, except the activity was measured with a liquid scintillation counter (Beckman Coulter LS 6500, Brea, Calif., USA).

Western Blot

Cell lysates from 1×10$^6$ cells were prepared by scraping cells into ice-cold harvesting buffer (Lysis Buffer). The lysates were boiled for 5 min and supernatants were collected after centrifugation in an Eppendorf microcentrifuge (14,000 rpm, 5 min) at 4° C. The protein concentration of the supernatant was determined by Bradford assay. Equal amounts of protein (50 μg) were loaded onto 10% SDS-polyacrylamide mini-gels and after gel electrophoresis proteins were transferred to a nitrocellulose membrane and blocked at room temperature using 5% non-fat milk blocking buffer (15 mL 1×TBST, 0.01% Tween 20 and 0.75 g milk powder). Following this, membrane was incubated overnight at 4° C. with goat polyclonal anti-σ-1 receptor ((S-18): sc-22948, Santa Cruz Biotechnology, Inc., Santa Cruz, Calif.) primary antibody. The primary antibody was diluted 1:400 in 5% non-fat milk blocking buffer. After washing three times with TBST (TBS with 0.01% Tween 20), bovine anti-goat-IgG horseradish peroxidase-conjugated antibody (Santa Cruz Biotechnology, Inc., Santa Cruz, Calif.) diluted 1:5000 in TBST, was added and incubated for 1 h at room temperature. After washing three times with TBST, σ-1 receptor protein was visualized using ECL reagent (Pierce, Rockford, Ill., USA) and images were obtained using film. Blot was also stained for alpha-tubulin as a protein loading control. Image J (image processing and analysis software in java) was used for western blot analysis.

In Vitro Metabolite Studies in Mouse Serum

Stability of [$^{18}$F]FTC-146 in mouse serum was assessed using a similar technique to that described by Kronauge and colleagues in 1992.[53] To 1 mL mouse serum (previously equilibrated in a 37° C. water bath) we added 100 μL of [$^{18}$F]FTC-146 (from a 3-5 mCi/mL formulated solution), vortexed the mixture, and then incubated at 37° C. Aliquots (100 μL) of the radioactive serum mixtures were removed at 5, 15, 30, 60 and 120 minutes and treated with ice cold ACN (200 μL) to stop enzymatic hydrolysis. The samples were cooled on ice and then centrifuged at 2,500 g for 10 min. The supernatant from each sample was separated from the pelleted cells and 100 μL was assessed via analytical HPLC. The percentage ratio of [$^{18}$F]FTC-146 (tR=6.7 min) to the total radioactivity (corrected for decay) on the HPLC chromatogram was calculated as %=(peak area for [$^{18}$F]FTC-146/total peak area)×100. A small volume (50 μL) from each supernatant was removed for activity measurement in a gamma-counter. Pelleted cells were washed once with 0.5 mL ACN and then counted, and the activity in the supernatant was compared to that in the pellet to afford the percentage of the tracer bound to serum proteins.

Small-Animal PET Imaging in Mice

Normal Balb C mice (25-35 g) were anaesthetized using isoflurane gas (3% for induction and 2% for maintenance). Acquisition of the PET data in list mode was commenced just prior to iv administration of [$^{18}$F]FTC-146 (95-125 µCi in 100 uL 0.9% saline) via the tail vein, and was continued for a period of 62 min. Following dynamic scanning, two subsequent 5 minute static scans were performed. Blocking studies involved pre-treatment of mice with different doses of CM304 (0.1 mg/kg, 1 mg/kg, 2 mg/kg) ten minutes prior to tracer administration.

In Vitro Half-Life Studies in Mouse and Rat Liver Microsomes

CM304 was incubated in the presence of an NADPH-generating system at 37° C. for 60 min in test tubes. The basic incubation mixture consisted of 5 mM substrate, 1 mg/mL microsomal protein, 3 mM $MgCl_2$, 1 mM NADP, 5 mM glucose-6-phosphate, 1 IU/mL glucose-6-phosphate dehydrogenase, 100 mM Tris HCl buffer (pH 7.4) in a final volume of 1 mL. The reaction was initiated by adding cofactors and quenched at designated time points (0, 5, 10, 15, 30, 45, 60 min) by addition of an equal volume of ice-cold ACN. The mixture was centrifuged at 3000 rpm for 10 min, and the supernatant was analysed by UPLC/MS/MS.

In Vivo Cocaine Studies

Male Swiss Webster mice were pretreated (i.p.) with saline or CM304 (0.001, 0.01, 0.1, 1.0, or 10 mg/kg) and challenged 15 min later with a convulsive dose of cocaine (70 mg/kg, i.p.). The mice were continuously monitored for the next 30 min for the onset of convulsions, which were operationally defined as the loss of righting reflexes for at least 5 sec combined with the presence of clonic or tonic limb movements. Fisher's exact tests were used to determine whether there was a significant difference between the ratios of mice exhibiting convulsions and not, at each tested dose.

The examples provided in the present application serve to illustrate the invention, but should not be construed as a limitation thereof.

The present radioligands can be used for radioligand binding assays and PET imaging. The present sigma-1 receptors and radioligands can be applied to both imaging and therapeutics in the following areas related to sigma-1 receptors:

1) Drug addiction (e.g., Cocaine & Methamphetamine) & therapy;[54, 55]

2) Sigma-1R as a molecular chaperone to direct specificity of Sigma-1R-related pharmacotherapy;[56]

3) Chronic pain;[57, 58, 59, 60]

4) Cancer;[61, 62]

5) Neuroinflammation (especially in cocaine-HIV-related CNS inflammation or pain);

6) Alzheimer's;[63, 64]

7) Parkinson's;[65]

8) Schizophrenia;[66, 67, 68, 69]

9) Major Depression & Anxiety;[70, 71, 72]

10) Multiple Sclerosis;[73] and

11) Obsessive Compulsive Disorder.[74, 75, 76]

The radioligands can be used in an injectable form and can be formulated using sterile injectable formulating media such as, for example, saline or ethanolic saline. Such formulation and the dosage used for imaging can be readily determined by those skilled in the art.

REFERENCES CITED (1) Matsumoto, R. R.; McCracken, K. A.; Pouw, B.; Miller, J.; Bowen, W. D.; Williams, W.; De Costa, B. R. N-alkyl substitute analogs of the σ receptor ligand BD1008 and traditional σ receptor ligands affect cocaine-induced convulsions and lethality in mice. *Eur. J. Pharmacol.* 2001, 411, 261-273.

(2) Maurice, T.; Lockhart, B. P. Neuroprotective and anti-amnesic prtentials of sigma (σ) receptor ligands. *Prog. Neuropsychopharmacol. Biol. Psychiatry* 1997, 21, 69-102.

(3) Matsumoto, R. R.; Bowen, W. D.; Su, T. P., eds. *Sigma receptors: chemistry, cell biology and clinical implications*. New York: Springer, 2007.

(4) Hanner, M.; Moebus, F. F.; Flandorfer, A.; Knaus, H-G.; Striessing, J.; Kempner, E.; Glossmann, H. Purification, molecular cloning, and expression of the mammalian $sigma_1$-binding site. *Proc. Natl. Acad. Sci. USA,* 1996, 93, 8072-8077.

(5) Kekuda, R.; Prasad, P. D.; Fei, Y-J.; Leibach, F. H.; Ganapathy, V. Cloning and functional expression of the human type 1 sigma receptor (hSigmaR1). *Biochem. Biophys. Res. Commun.* 1996, 229, 553-558.

(6) Seth, P.; Leibach, F. H.; Ganapathy, V. Cloning and structural analysis of the cDNA and the gene encoding the murine type 1 sigma receptor. *Biochem. Biophys. Res. Commun.* 1997, 241, 535-540.

(7) Seth, P.; Fei, Y-J.; Li, H. W.; Huang, W.; Leibach, F. H.; Ganapathy, V. Cloning and functional characterization of a σ receptor from rat brain. *J. Neurochem.* 1998, 70, 922-931.

(8) Mei, J.; Pasternak, G. W. Molecular cloning and pharmaceutical characterization of the rat $sigma_1$ receptor. *Biochem. Pharmacol.* 2001, 62, 349-355.

(9) Perrine, D. M. *The Chemistry of Mind-Altering Drugs*. Washington, D.C.: American Chemical Society, 1996.

(10) Wohler, V. Fortsetzung der Untersuchungen uber die Coca and das Cocain. *Justus Liebigs Annalen der Chemie* 1862, 121, 372, 372.

(11) National Survey on Drug Use and Health—http://www.sambsa.gov

(12) Carroll, F. I.; Howell, L. L.; Kuhar, M. J. Pharmacotherapies for treatment of cocaine abuse: preclinical aspects. *J. Med. Chem.* 1999, 42, 2721-2736.

(13) Sharkey, J.; Glen, K. A.; Wolfe, S.; Kuhar, M. J. Cocaine binding at sigma receptors. *Eur. J. Pharmacol.* 1988, 149, 171-174.

(14) Mittleman, R.; Wetli, C. V. Death caused by recreational cocaine use: an update. *JAMA* 1984, 252, 1889-1893.

(15) Martin, W. R.; Eades, C. G.; Thompson, J. A.; Huppler, R. E.; Gilbert, P. E. The effects of morphine- and nalorphine-like drugs in the nondependent and morphine-dependent chronic spinal dog. *J Pharmacol Exp Ther.* 1976, 197, 517-32.

(16) Martin, W. R. A steric theory of opioid agonists, antagonists, agonist-antagonists, and partial agonists. *NIDA Res Monogr.* 1984, 49, 16-23.

(17) Hellewell, S. B.; Bruce, A.; Feinstein, G.; Orringer, J.; Williams, W.; Bowen, W. D. Rat liver and kidney contain high densities of sigma 1 and sigma 2 receptors: characterization by ligand binding and photoaffinity labeling. *Eur J Pharmacol.* 1994, 268, 9-18.

(18) Maurice, T.; Su, T. P. The pharmacology of sigma-1 receptors. *Pharmacol Ther.* 2009, 124, 195-206.

(19) Quirion, R.; Bowen, W. D.; Itzhak, Y.; Junien, J. L.; Musacchio, J. M.; Rothman, R. B.; Su, T. P.; Tam, S. W.; Taylor, D. P. A proposal for the classification of sigma binding sites. *Trends Pharmacol Sci.* 1992, 13, 85-6.

(20) Guitart, X.; Codony, X.; Monroy, X. Sigma receptors: biology and therapeutic potential. *Psychopharmacology (Berl)*. 2004, 174, 301-19.

(21) Walker, J. M.; Bowen, W. D.; Walker, F. O.; Matsumoto, R. R.; De Costa, B.; Rice, K. C. Sigma receptors: biology and function. *Pharmacol Rev.* 1990, 42, 355-402.

(22) Maurice, T.; Phan, V. L.; Privat, A. The anti-amnesic effects of sigma1 (sigma1) receptor agonists confirmed by in vivo antisense strategy in the mouse. *Brain Res.* 2001, 898, 113-21.

(23) Su, T. P. Delineating biochemical and functional properties of sigma receptors: emerging concepts. *Crit Rev Neurobiol.* 1993, 7, 187-203.

(24) Vilner, B. J.; John, C. S.; Bowen, W. D. Sigma-1 and sigma-2 receptors are expressed in a wide variety of human and rodent tumor cell lines. *Cancer Res.* 1995, 55, 408-13.

(25) Wang, B.; Rouzier, R.; Albarracin, C. T.; Sahin, A.; Wagner, P.; Yang, Y.; Smith, T. L.; Meric-Bernstam, F.; Marcelo Aldaz, C.; Hortobagyi, G. N.; Pusztai, L. Expression of sigma 1 receptor in human breast cancer. *Breast Cancer Res Treat.* 2004, 87, 205-14.

(26) Gonzalez, G. M.; Werling, L. L. Release of [3H] dopamine from guinea pig striatal slices is modulated by sigma1 receptor agonists. *Naunyn Schmiedebergs Arch Pharmacol.* 1997, 356, 455-61.

(27) Kobayashi, T.; Matsuno, K.; Nakata, K.; Mita, S. Enhancement of acetylcholine release by SA4503, a novel sigma 1 receptor agonist, in the rat brain. *J Pharmacol Exp Ther.* 1996, 279, 106-13.

(28) Collier, T. L.; Waterhouse, R. N.; Kassiou, M. Imaging sigma receptors: applications in drug development. *Curr Pharm Des.* 2007, 13, 51-72.

(29) Maurice, T. Improving Alzheimer's Disease-Related Cognitive Deficits with sigma1 Receptor Agonists. *Drug News Perspect.* 2002, 15, 617-625.

(30) Senda, T.; Matsuno, K.; Kobayashi, T.; Nakazawa, M.; Nakata, K.; Mita, S. Ameliorative effect of SA4503, a novel cognitive enhancer, on the basal forebrain lesion-induced impairment of the spatial learning performance in rats. *Pharmacol Biochem Behav.* 1998, 59, 129-34.

(31) Harukuni, I.; Bhardwaj, A.; Shaivitz, A. B.; DeVries, A. C.; London, E. D.; Hurn, P. D.; Traystman, R. J.; Kirsch, J. R.; Faraci, F. M. sigma(1)-receptor ligand 4-phenyl-1-(4-phenylbutyl)-piperidine affords neuroprotection from focal ischemia with prolonged reperfusion. *Stroke.* 2000, 31, 976-82.

(32) Volz, H. P.; Stoll, K. D. Clinical trials with sigma ligands. *Pharmacopsychiatry.* 2004, 37 Suppl 3, S214-20.

(33) Xu, Y. T.; Kaushal, N.; Shaikh, J.; Wilson, L. L.; Mesangeau, C.; McCurdy, C. R.; Matsumoto, R. R. A novel substituted piperazine, CM156, attenuates the stimulant and toxic effects of cocaine in mice. *J Pharmacol Exp Ther.* 2010, 333, 491-500.

(34) Ucar, H.; Cacciaguerra, S.; Spampinato, S.; Van derpoorten, K.; Isa, M.; Kanyonyo, M.; Poupaert, J. H. 2(3H)-benzoxazolone and 2(3H)-benzothiazolone derivatives: novel, potent and selective sigma1 receptor ligands. *Eur J Pharmacol.* 1997, 335, 267-73.

(35) Berardi, F.; Ferorelli, S.; Abate, C.; Pedone, M. P.; Colabufo, N. A.; Contino, M.; Perrone, R. Methyl substitution on the piperidine ring of N-[omega-(6-methoxynaphthalen-1-yl)alkyl] derivatives as a probe for selective binding and activity at the sigma(1) receptor. *J Med Chem.* 2005, 48, 8237-44.

(36) Hudkins, R. L.; Mailman, R. B.; DeHaven-Hudkins, D. L. RLH-033, a novel, potent and selective ligand for the sigma 1 recognition site. *Eur J Pharmacol.* 1994, 271, 235-6.

(37) Maestrup, E. G.; Fischer, S.; Wiese, C.; Schepmann, D.; Hiller, A.; Deuther-Conrad, W.; Steinbach, J.; Wunsch, B.; Brust, P. Evaluation of spirocyclic 3-(3-fluoropropyl)-2-benzofurans as sigma1 receptor ligands for neuroimaging with positron emission tomography. *J Med Chem.* 2009, 52, 6062-72.

(38) Matsuno, K.; Nakazawa, M.; Okamoto, K.; Kawashima, Y.; Mita, S. Binding properties of SA4503, a novel and selective sigma 1 receptor agonist. *Eur J Pharmacol.* 1996, 306, 271-9.

(39) Moussa, I. A.; Banister, S. D.; Beinat, C.; Giboureau, N.; Reynolds, A. J.; Kassiou, M. Design, synthesis, and structure-affinity relationships of regioisomeric N-benzyl alkyl ether piperazine derivatives as sigma-1 receptor ligands. *J Med Chem.* 2010, 53, 6228-39.

(40) Piergentili, A.; Amantini, C.; Del Bello, F.; Giannella, M.; Mattioli, L.; Palmery, M.; Perfumi, M.; Pigini, M.; Santoni, G.; Tucci, P.; Zotti, M.; Quaglia, W. Novel highly potent and selective sigma 1 receptor antagonists related to spipethiane. *J Med Chem.* 2010, 53, 1261-9.

(41) Quaglia, W.; Giannella, M.; Piergentili, A.; Pigini, M.; Brasili, L.; Di Toro, R.; Rossetti, L.; Spampinato, S.; Melchiorre, C. 1'-Benzyl-3,4-dihydrospiro[2H-1-benzothiopyran-2,4'-piperidine] (spipethiane), a potent and highly selective sigma1 ligand. *J Med Chem.* 1998, 41, 1557-60.

(42) Yous, S.; Wallez, V.; Belloir, M.; Caignard, D. H.; McCurdy, C. R. Novel 2(3H)-Benzothiazolones as Highly Potent and Selective Sigma-1 Receptor Ligands. *Med Chem Res.* 2005, 14, 158-168.

(43) Kawamura, K.; Ishiwata, K.; Tajima, H.; Ishii, S.; Matsuno, K.; Homma, Y.; Senda, M. In vivo evaluation of [$^{11}$C]SA4503 as a PET ligand for mapping CNS sigma(1) receptors. *Nucl Med Biol.* 2000, 27, 255-61.

(44) Kawamura, K.; Tsukada, H.; Shiba, K.; Tsuji, C.; Harada, N.; Kimura, Y.; Ishiwata, K. Synthesis and evaluation of fluorine-18-labeled SA4503 as a selective sigma1 receptor ligand for positron emission tomography. *Nucl Med Biol.* 2007, 34, 571-7.

(45) Waterhouse, R. N.; Collier, T. L. In vivo evaluation of [$^{18}$F]1-(3-fluoropropyl)-4-(4-cyanophenoxymethyl)piperidine: a selective sigma-1 receptor radioligand for PET. *Nucl Med Biol.* 1997, 24, 127-34.

(46) Waterhouse, R. N.; Chang, R. C.; Zhao, J.; Carambot, P. E. In vivo evaluation in rats of [$^{18}$F]1-(2-fluoroethyl)-4-[(4-cyanophenoxy)methyl]piperidine as a potential radiotracer for PET assessment of CNS sigma-1 receptors. *Nucl Med Biol.* 2006, 33, 211-5.

(47) Waterhouse, R. N.; Zhao, J.; Stabin, M. G.; Ng, H.; Schindler-Horvat, J.; Chang, R. C.; Mirsalis, J. C. Preclinical acute toxicity studies and dosimetry estimates of the novel sigma-1 receptor radiotracer, [$^{18}$F]SFE. *Mol Imaging Biol.* 2006, 8, 284-91.

(48) Mach, R. H.; Gage, H. D.; Buchheimer, N.; Huang, Y.; Kuhner, R.; Wu, L.; Morton, T. E.; Ehrenkaufer, R. L. N-[$^{18}$F]4'-fluorobenzylpiperidin-4yl-(2-fluorophenyl) acetamide ([18F]FBFPA): a potential fluorine-18 labeled PET radiotracer for imaging sigma-1 receptors in the CNS. *Synapse.* 2005, 58, 267-74.

(49) Fischer, S.; Wiese, C.; Grosse Maestrup, E.; Hiller, A.; Deuther-Conrad, W.; Scheunemann, M.; Schepmann, D.; Steinbach, J.; Wunsch, B.; Brust, P. Molecular imaging of sigma receptors: synthesis and evaluation of the potent sigma(1) selective radioligand [$^{18}$F]fluspidine. *Eur J Nucl Med Mol Imaging.* 2010.
(50) Fishback, J. A.; Mesangeau, C.; Poupaert, J. H.; McCurdy, C. R.; Matsumoto, R. R. Synthesis and characterization of [$^3$H]—SN56, a novel radioligand for the al receptor. *European Journal of Pharmacology.* In Press.
(51) Bowen, W. D.; Tolentino, P. J.; Kirschner, B. N.; Varghese, P.; de Costa, B. R.; Rice, K. C. Sigma receptors and signal transduction: negative modulation of signaling through phosphoinositide-linked receptor systems. *NIDA Res Monogr.* 1993, 133, 69-93.
(52) Loening, A. M.; Gambhir, S. S. AMIDE: a free software tool for multimodality medical image analysis. *Mol Imaging.* 2003, 2, 131-7.
(53) Kronauge, J. F.; Noska, M. A.; Davison, A.; Holman, B. L.; Jones, A. G. Interspecies variation in biodistribution of technetium (2-carbomethoxy-2-isocyanopropane)6+. *J Nucl Med.* 1992, 33, 1357-65.
(54) Rodvelt, K. R.; Lever, S. Z.; Lever, J. R.; Blount, L. R.; Fan, K.-H.; Miller, D. K. SA 4503 attenuates cocaine-induced hyperactivity and enhances methamphetamine substitution for a cocaine discriminative stimulus. *Pharmacology, Biochemistry and Behavior.* 2011, 97, 676-682.
(55) Matsumoto, R. R.; Liu, Y.; Lerner, M.; Howard, E. W.; Brackett, D. J. Sigma receptors: potential medications development target for anti-cocaine agents. *Eur. J. Pharmacol.,* 2003, 469, 1-12.
(56) Su, T.-P.; Hayashi, T.; Maurice, T.; Buch, S.; Ruoho, A. E. The sigma-1 receptor chaperone as an inter-organelle signaling modulator. *Trends in Pharmacological Sciences.* 2010, 31,557-566
(57) Roh, D.-H.; Kim, H.-W.; Yoon, S.-Y.; Seo, H.-S.; Kwon, Y.-B.; Kim, K.-W.; Han, H.-J.; Beitz, A. J.; Lee, J.-H. Intrathecal Administration of Sigma-1 Receptor Agonists Facilitates Nociception: Involvement of a Protein Kinase C-development Pathway. *Journal of Neuroscience Research.* 2008, 86, 3644-3654.
(58) Roh, D.-H.; Kim, H.-W.; Yoon, S.-Y.; Seo, H.-S.; Kwon, Y.-B.; Kim, K.-W.; Han, H.-J.; Beitz, A. J.; Na, H.-S.; Lee, J.-H. Intrathecal injection of the al receptor antagonist BD1047 blocks both mechanical allodynia and increases in spinal NR1 expression during the induction phase of rodent neuropathic pain. *Anesthesiology.* 2008, 109, 879-889.
(59) Kibaly, C.; Meyer, L.; Patte-Mensah, C.; Mensah-Nyagan, A. G. Biochemical and functional evidence for the control of pain mechanisms by dehydroepiandrosterone endogenously synthesized in the spinal cord. *The FASEB Journal.* 2008, 22, 93-104.
(60) de la Puente, B.; Nadal, X.; Portillo-Salido, E.; Sanchez-Arroyos, R.; Ovalle, S.; Palacios, G.; Nuro, A.; Romero, L.; Entrena, J. M.; Baeyens, J. M.; Lopez-Garcia, J. A.; Maldonado, R.; Zamanillo, D.; Vela, J. M. Sigma-1 receptors regulate activity-induced spinal sensitization and neuropathic pain after peripheral nerve injury. *Pain.* 2009, 145, 294-303.
(61) Rybczynska, A. A.; Elisinga, P. H.; Sijbesma, J. W.; Ishiwata, K.; de Jong, J. R.; de Vries, E. F.; Dierckx, R. A.; van Waarde, A. Steroid hormones affect binding of the sigma ligand $^{11}$C-5A4503 in tumour cells and tumour-bearing rats. *Eur. J. Nucl Med Mol Imaging.* 2009, 36, 1167-1175.
(62) van Waarde, A.; Rybczynska, A. A.; Ramakrishnan, N.; Ishiwata, K.; Elsinga, P. H.; Dierckx, R. A. Sigma receptors in oncology: therapeutic and diagnostic applications of sigma ligands. *Curr Pharm Des.* 2010, 16, 3519-1537.
(63) Jansen, K. L. R.; Faull, R. L. M.; Storey, P.; Leslie, R. A. Loss of sigma binding sites in the CA1 area of the anterior hippocampus in Alzheimer's disease correlates with CA1 pyramidal cell loss. *Brain Research.* 1993, 623, 299-302.
(64) Mishina, M.; Ohyama, M.; Ishii, K.; Kitamura, S.; Kimura, Y.; Oda, K.-i.; Kawamura, K.; Sasaki, T.; Kobayashi, S.; Katayama, Y.; Ishiwata, K. Low density of sigma$_1$ receptors in early Alzheimer's disease. *Ann. Nucl. Med.* 2008, 22, 151-156.
(65) Mishina, M.; Ishiwata, K.; Ishii, K.; Kitamura, S.; Kimura, Y.; Kawamura, K.; Oda, K.; Sasaki, T.; Sakayori, O.; Hamamoto, M.; Kobayashi, S.; Katayama, Y. Function of sigma$_1$ receptors in Parkinsons's disease. *Acta Neurol Scand.* 2005, 112, 103-107.
(66) Weissman, A. D.; Casanova, M. F.; Kleinman, J. E.; London, E. D.; de Souza, E. B. Selective loss of cerebral cortical Sigma, but not PCP binding sites in schizophrenia. *Biol Psychiatry.* 1991, 29, 41-54.
(67) Shibuya, H.; Mori, H.; Toni, M. Sigma receptors in schizophrenic cerebral cortices. *Neurochem Res.* 1992, 17, 983-990.
(68) Silver, H.; Barash, I.; Aharon, N.; Kaplan, A.; Poyurovsky, M. Fluvoxamine augmentation of antipsychotics improves negative symptoms in psychotic chronic schizophrenic patients: a placebo-controlled study. *Int. Clin. Psychopharmacol.* 2000, 15, 257-261.
(69) Iyo, M.; Shirayama, Y.; Watanabe, H.; Fujisaki, M.; Miyatake, R.; Fukami, G.; Shiina, A.; Nakazato, M.; Shiraishi, T. Letter to the Editor (Case Report): Fluvoxamine as a sigma-1 receptor agonist improved cognitive impairments in a patient with schizophrenia. *Prog. Neuropsych. Biol. Psych.* 2008, 32, 1072-1073.
(70) Gatti, F.; Bellini, L.; Gasperini, M.; Perez, J.; Zanardi, R.; Smeraldi, E. Fluvoxamine alone in the treatment of delusional depression. *Am. J. Psychiatry,* 1996, 153, 414-416.
(71) Narita, N.; Hashimoto, K.; Tomitaka, S.-i.; Minabe, Y. Interactions of selective serotonin reuptake inhibitors with subtypes of σ receptors in rat brain. *Eur. J. Pharmacol.* 1996, 307, 117-119.
(72) Zanardi, R.; Franchini, L.; Gasperini, M.; Lucca, A.; Smeraldi, E.; Perez, J. Faster Onset of Action of Fluvoxamine in Combination with Pindolol in the Treatment of Delusional Depression: A controlled study. *J. Clin. Psychopharmacol.* 1998, 18, 441-446.
(73) Haiman, G.; Pratt, H.; Miller, A. Effects of dextromethorphan/quinidine on auditory event-related potentials in multiple sclerosis patients with pseudobulbar affect. *J. Clin. Psychopharmacol.* 2009, 29, 444-452.
(74) Cottraux, J.; Mollard, E.; Bouvard, M.; Marks, I. Exposure therapy, fluvoxamine, or combination treatment in obsessive-compulsive disorder: one-year follow up. *Psychiatry Research.* 1993, 49, 63-75.
(75) Hohagen, F.; Berger, M. New perspectives in research and treatment of obsessive-compulsive disorder. *Br. J. Psychiatry* Suppl. 1998, 35, 1.
(76) Dell'Osso, B.; Allen, A.; Hollander, E. Fluvoxamine: a selective serotonin re-uptake inhibitor for the treatment of obsessive-compulsive disorder. *Expert Opinion on Pharmacotherapy.* 2005, 6, 2727-2740.

We claim:

1. Compounds having the general formula III', or IV'

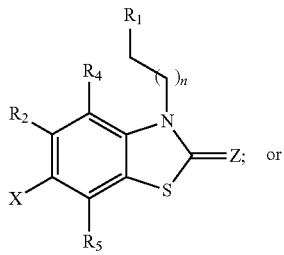

III'

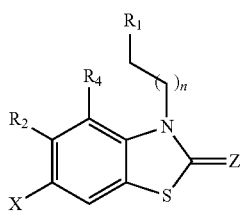

IV' wherein R₁ is a radical of an optionally substituted piperazine, an optionally substituted tetrahydropyridine, an optionally substituted azepane or an optionally substituted tetrahydroisoquinoline in which the optional substituents are on the aromatic moiety or isoindoline-1,3-dione; $R_{2,4,5}$ are each independently any one or combinations of the following moieties, hydrogen, cyano, nitro, acyl, alkyl, amido, azido, isothiocyanate, isocyanate, optionally substituted anilino, halogens, ethers, sulfonamides, thioacyl, nitro, aromatic, heterocyclic, olefinic, acetylene, deuterium, or tritium; Z is O, "n" is 1 to 5 carbons in length; wherein the moiety bridging $R_1$ and N is a substituted alkylene; and wherein X is $C_1$-$C_4$ haloalkyl or $C_1$-$C_4$ radiohaloalkyl; and stereoisomers, or pharmaceutically acceptable salts thereof.

2. The compounds according to claim 1, wherein the optionally substituted N-containing heterocyclic radical is an optionally substituted azepane.

3. The compounds of claim 1, having the formula XII'

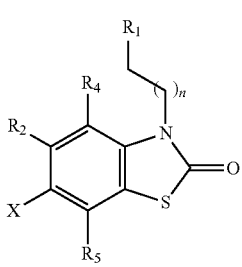

XII' wherein n=1-5.

4. The compounds of claim 1, where R1 is optionally substituted

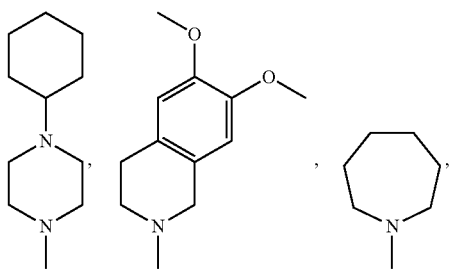

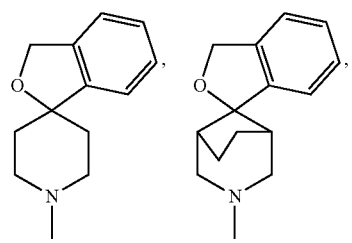

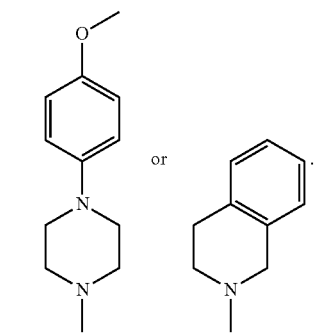

5. The compounds of claim 1, wherein X is $F^{18}$ $C_1$-$C_4$ alkyl.

6. A radioligand composition comprising at least one compound according to claim 1 wherein at least one compound contains a radioactive fluorine 18.

7. A method of preparing a $C_1$-$C_4$ radiohaloalkyl compound according to claim 1 comprising radio-halogenating a compound according to claim 1 wherein X is an alkyl substituted with a leaving group in the presence of a polar aprotic solvent.

8. A radioligand composition comprising at least one compound according to claim 1 wherein at least one compound contains a radioactive carbon 11.

* * * * *